US006541647B2

(12) United States Patent
Chorghade et al.

(10) Patent No.: US 6,541,647 B2
(45) Date of Patent: Apr. 1, 2003

(54) METHODS OF SYNTHESIS OF SUBSTITUTED TETRAHYDROFURAN COMPOUND

(75) Inventors: Mukund Shankar Chorghade, Natick, MA (US); Mukund Keshao Gurjar, Pune (IN); Palakodety Radha Krishna, Hyderabad (IN); Sista Venkata Sai Lalitha, Sunnyvale, CA (US); Kashinath Sadalapure, Dt. Gulbarga (IN); Susanta Sekhar Adhikari, West Bengal (IN); Andappan Murugaiah Subbaiah Murugaiah, Tamilnadu (IN); Sunil Vyankatesh Mhaskar, Natick, MA (US); Gangavaram Vasantha Madhava Sharma, Hyderabad (IN); Tangallapally Rajendra Prasad, Warangal (IN); Punna Sreenivas, Nalgonda (IN); Vavilala Goverdhan Reddy, Mahabubnagar (IN); Aminul Islam, Hyderabad (IN); Chittineni Hari Prasad, Hyderabad (IN); Alla Venkata Rama Rao, Hyderabad (IN)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/969,799

(22) Filed: Oct. 2, 2001

(65) Prior Publication Data

US 2002/0035278 A1 Mar. 21, 2002

Related U.S. Application Data

(63) Continuation of application No. 09/347,087, filed on Jul. 2, 1999, now Pat. No. 6,310,221.
(60) Provisional application No. 60/091,709, filed on Jul. 3, 1998.

(51) Int. Cl.[7] ..................... C07D 307/33; C07D 307/12

(52) U.S. Cl. ........................ 549/323; 549/497
(58) Field of Search ................... 549/323, 497

(56) References Cited

U.S. PATENT DOCUMENTS

| | | | |
|---|---|---|---|
| 5,037,853 A | 8/1991 | Brooks et al. | 514/595 |
| 5,112,848 A | 5/1992 | Brooks et al. | 514/424 |
| 5,169,854 A | 12/1992 | Brooks et al. | 514/314 |
| 5,175,183 A | 12/1992 | Brooks et al. | 514/438 |
| 5,183,818 A | 2/1993 | Brooks et al. | 514/231.5 |
| 5,187,192 A | 2/1993 | Brooks et al. | 514/445 |
| 5,288,751 A | 2/1994 | Brooks et al. | 514/438 |
| 5,326,787 A | 7/1994 | Brooks et al. | 514/507 |
| 5,358,938 A | 10/1994 | Cai et al. | 514/231.5 |
| 5,434,151 A | 7/1995 | Cai et al. | 514/231.5 |
| 5,463,083 A | 10/1995 | Biftu et al. | 549/71 |
| 5,530,141 A | 6/1996 | Shen et al. | 549/39 |
| 5,543,531 A | 8/1996 | Funfschilling et al. | |
| 5,639,782 A | 6/1997 | Shen et al. | 574/440 |
| 5,681,966 A | 10/1997 | Cai et al. | 549/65 |
| 5,703,093 A | 12/1997 | Cai et al. | 514/473 |
| 5,741,809 A | 4/1998 | Biftu et al. | 514/428 |
| 5,750,565 A | 5/1998 | Cai et al. | 514/473 |
| 5,756,768 A | 5/1998 | Kanou et al. | |
| 5,780,503 A | 7/1998 | Biftu et al. | 514/471 |
| 5,792,776 A | 8/1998 | Biftu et al. | 514/303 |
| 5,856,323 A | 1/1999 | Cai et al. | 514/231.5 |

FOREIGN PATENT DOCUMENTS

| | | |
|---|---|---|
| WO | WO 92/15294 | 9/1992 |
| WO | WO 94/01430 | 1/1994 |
| WO | WO 94/06790 | 3/1994 |
| WO | WO 95/18610 | 7/1995 |
| WO | WO 96/00212 | 1/1996 |

*Primary Examiner*—Bernard Dentz
(74) *Attorney, Agent, or Firm*—Hamilton, Brook, Smith & Reynolds, P.C.

(57) ABSTRACT

The invention includes inter alia new methods for preparation of the pharmaceutically active compound 2-(4-fluorophenoxymethyl)-5-(4-N-hydroxyureidyl-1-butynyl)-tetrahydrofuran and precursors thereof.

18 Claims, No Drawings

METHODS OF SYNTHESIS OF SUBSTITUTED TETRAHYDROFURAN COMPOUND

The present application is a continuation of U.S. application Ser. No. 09/347,087, filed on Jul. 2, 1999, now U.S. Pat. No. 6,310,221.

BACKGROUND

1. Field of the Invention

The present invention provides new methods for preparation of 2-(4-fluorophenoxymethyl)-5-(4-N-hydroxyureidyl-1-butynyl)-tetrahydrofuran ("compound 1") and synthetic precursors thereof.

2. Background

Leukotrienes are recognized potent local mediators, playing a significant role in inflammatory and allegeric responses, including arthritis, asthma, psoriasis and thrombotic disease. Leukotrienes are produced by the oxidation of arachidonic acid by lipoxygenase. More particularly, arachidonic acid is oxidized by 5-lipooxygenase to the hydroperoxide 5-hydroperoxy-eicosatetraenoic acid (5-HPETE), that is converted to leukotriene $A_4$, that in turn can be converted to leukotriene $B_4$, $C_4$, or $D_4$. The slow-reacting substance of anaphylaxis is now known to be a mixture of leukotrienes $C_4$, $D_4$ and $E_4$, all of which are potent bronchoconstrictors.

Efforts have been made to identify receptor antagonists or inhibitors of leukotriene biosynthesis, to prevent or minimize pathogenic inflammatory responses mediated by leukotrienes.

For example, European Patent Application Nos. 901171171.0 and 901170171.0 report indole, benzofuran, and benzothiophene lipoxygenase inhibiting compounds.

Various 2,5-disubstituted tetrahydrofurans have exhibited significant biological activity, including as lipoxygenase inhibitors. See U.S. Pat. Nos. 5,703,093; 5,681,966; 5,648,486; 5,434,151; and 5,358,938.

While such compounds are highly useful therapeutic agents, current methods for synthesis of least some of the compounds require lengthy routes, and reagents and protocols that are less preferred in larger scale operations, such as to produce kilogram quantities.

SUMMARY OF THE INVENTION

We have now found new methods for preparation of 2-(4-fluorophenoxymethyl)-5-(4-N-hydroxyureidyl-1-butynyl)-tetrahydrofaran and precursor compounds thereof. 2-(4-Fluorophenoxymethyl)-5-(4-N-hydroxyureidyl-1-butynyl)-tetrahydrofuran is sometimes referred to herein as "compound 1". Preferred methods of the invention provide compound 1 in optically active form, particularly as an enantiomerically enriched mixture of the following stereoisomer (i.e. 2S,5S-trans-2-(4-fluorophenoxymethyl)-5-(4-N-hydroxyureidyl-1-butynyl)-tetrahydrofuran):

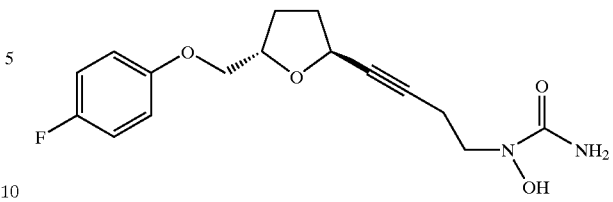

The methods of the invention utilize reagents and synthetic protocols that facilitate large scale manufacture, and provide increased yields relative to prior approaches.

In a first aspect of the invention, compound 1 and precursors thereof are provided by reacting 4-fluorophenol with an epoxide having a reactive C3 carbon, e.g. a glycidyl compound substituted at the C3 position with an electron-withdrawing group such as halo (e.g. epichlorohydrin, epibromohydrin), mesyl or tosyl (glycidyl mesylate and glycidyl tosylate), etc., to form an epoxyphenylether ((glycidyl-4-fluorophenyl ether) in the presence of base and preferably at or above about 0° C. The reacted epoxide can be optically active if desired. The formed epoxyphenylether is then reacted with an active methylene compound to form a lactone, preferably a γ-lactone, with 5 ring members. The active methylene compound can be a variety of agents. Diethyl and dimethyl malonate are generally preferred, which provide an ethyl or methyl ester as a lactone ring substituent, i.e. 2-carboalkoxy-(4-fluoro-phenoxy-methyl)-γ-butyrolactone, where the alkoxy group suitably has from 1 to about 12 carbon atoms, more preferably 1 to about 6 carbon atoms, still more preferably 1 to about 3 carbons with methoxy and ethoxy particularly preferred. That ester group is then removed (e.g. via hydrolysis and decarboxylation), and the lactone suitably reduced to a hydroxy-substituted tetrahydrofuran, specifically 4-fluorophenoxymethyl-hydroxytetrahydrofuran.

The hydroxy tetrahydrofuran is further functionalized by activating the hydroxyl substituent of the hydroxytetrahydrofuran-phenyl ether followed by substitution of the corresponding position of the tetrahydrofuran ring with by a 1-alkyne reagent. Also, rather than directly activating the hydroxyl moiety, that group can be replaced with a halide, and the halide-substituted tetrahydrofuran reacted with a benzylsulfonic acid reagent.

It also has been found that methods of the invention enable such substitution of the tetrahydrofuran to proceed with extremely high stereoselectivity, e.g. at least greater than about 60 mole percent of one stereoisomer than the other, more typically greater than about 70 or 75 mole percent of one stereoisomer than the other isomer. Recrystallization has provided very high optical purities, e.g. about 95 mole %, 97 mole % or even 99 mole % or more of the single stereoisomer.

In another aspect, methods are provided that involve cleavage of a bis-compound to provide high yields of compound 1. These methods preferably involve condensation of mannitol with an alkanoyl particularly an aldehyde such as formaldehyde to form a trialkylene mannitol such as a tri($C_{1-10}$alkylene) mannitol e.g. trimethylene mannitol when using formaldehyde, which is then cleaved to form 2,5,-O-methylene-mannitol, which has two primary hydroxyl groups and two secondary hydroxyl groups. The primary hydroxyl groups are protected (e.g. as esters) and the secondary hydroxyl groups then are suitably cyclized, e.g. with a trialkylorthoformate reagent, to provide a cyclic ether. The protected primary alcohols are then converted to aryl ethers, followed by cleavage of the cyclic ether to provide again the secondary hydroxyl groups. The mannitol compound then undergoes oxidative cleavage to provide the corresponding alicyclic dialdehyde, which aldehyde groups are functionalized to bis-$\alpha,\beta$-unsaturated esters. The carbon-carbon double bonds of that compound are suitably saturated, and the bis-compound cleaved and the cleavage products cyclized to provide two molar equivalents of 4-fluorophenoxy-methyl-$\gamma$-butyrolactone which can be further functionalized as described above.

In yet another aspect of the invention, preparative methods are provided that include multiple reactions that surprisingly proceed as a single step without isolation of intermediates to provide compound 1.

Moreover, it has been surprisingly found that the one step procedure is enantioselective. Hence, if the starting reagent (a 2,3-epoxide) is optically active, the resulting compound 1 also will be optically active.

More particularly, in this aspect of the invention, a compound is reacted that has at least a six-carbon alkyl or alkylene chain that is activated at the 1- and 6-carbon positions such as by substitution by suitable leaving groups, and 2- and 3-carbon positions of the chain form an epoxide ring. The compound suitably has about 6–12 carbons in the chain. The leaving groups of the 1- and 6-positions may be e.g. halo, such as chloro or bromo, or an ester, such as an alkyl or aryl sulfonic ester, e.g. mesylate or other $C_{1-10}$ alkyl sulfonic ester, or a phenyl sulfonic ester such as tosylate and the like, or an arylalkyl ester such as benzylsulfonic ester. Preferably, the 1-position is halo-substituted, particularly bromo-, iodo- or chloro-substituted, and the 6-position is substituted by an ester such as by a benzylsulfonyl group. That compound is reacted with a molar excess of a strong base such as an alkyllithium reagent that affords compound 1 in a single step.

In another aspect of the invention, a chiral synthon is preferably employed such as glyceraldehyde, mannitol, ascorbic acid, and the like, to provide a stereoselective route to desired stereoisomers of compound 1. This route includes formation of a substituted dioxolane, typically a 1,3-dioxolane (particularly (2,2-dimethyl)- 1,3-dioxolane), which preferably is optically active. A side chain of the dioxolane, preferably at the 4-position, is suitably extended e.g. by one or more Wittig reactions, typically one or two Wittig reactions that provide B-unsaturated moieties such as an $\alpha,\beta$-unsaturated alkyl ester. Such an $\alpha,\beta$-unsaturated moiety provided then can be epoxidized, preferably by asymmetric oxidation of the conjugated alkene to provide an optically active epoxide, which then participates in an elimination reaction to yield a propargyl alcohol as the dioxolane ring substituent. The dioxolane ring then can be opened, typically in the presence of acid and the acyclic intermediate cyclized to provide an optically active tetrahydrofuran that is 1-alkyne-4-hydroxyalkyl-substituted, preferably 1-ethynyl4-hydroxymethyl-substituted. See generally Schemes VIII through X and the discussion related thereto below. The substituted tetrahydrofuran can be further functionalized as outlined above to provide compound 1. For instance, the primary hydroxy of the alkylhydroxy substituent can be esterified (e.g., sulfonate such as a tosylate) and the activated carbon reacted to provide an aryl substituent, particularly para-fluorophenyl. The alkynyl substituent can be extended to provided the hydroxy urea as discussed above.

In an alternative method of the invention, a substituted dioxolane reagent is employed, again typically a 1,3-dioxolane (particularly (2,2-dimethyl)- 1,3-dioxolane), which preferably is optically active. The dioxolane has an alkanoyl side chain, more particularly a propionaldehyde (—$CH_2CH_2C(=O)H$) substituent that is reacted suitably in the presence of base (e.g. an alkyllithium) with a 1-alkyne to provide a proparyl alcohol. The alkyne reagent is preferably a butynyl compound with terminal ether group, preferably a terminal aryl or alkaryl ether such as optionally substituted 1-(4-phenylmethylether)-butynyl. The resulting substituted dioxolane can be opened suitably in the presence of acid to an acyclic intermediate, followed by cyclization under basic conditions to provide a substituted tetrahydrofuran which can be further functionalized as discussed above with respect to Schemes VIII through X to provide compound 1. See generally Scheme XI and the discussion related thereto below.

In a further synthetic route of the invention, a substituted dioxolane reagent is employed, again typically a 1,3-dioxolane (particularly (2,2-dimethyl)- 1,3-dioxolane), which preferably is optically active. The dioloxane has a keto alkyne side chain, preferably —$CH_2CH_2C(=O)$ $C\equiv CR$ where R is optionally substituted alkyl, particularly C1–6 alkyl, or an alkylether or alkaryl ether such as a $C_{1-6}$ ether, preferably an ethyl aryl or other (C)alkylaryl ether such as —$CH_2CH_2OCH_2$(phenyl or substituted phenyl). The keto group is then reduced, preferably asymmetrically such as by use of a chiral catalyst, to provide a propargyl alcohol that can be further functionalized to compound 1 as generally discussed above. See Scheme XII and the related discussion below.

In yet a further aspect of the invention, an alkyne-substituted tetrahydrofuran is prepared directly (e.g., without a dioxolane intermediate) from an acyclic keto alkyne compound. More specifically, a keto alkynyl reagent with terminal alkenyl group is suitably employed, e.g. —$CH_2=CHCH_2CH_2C(=O)C\equiv CR$ where R is the same as defined immediately above. The terminal alkene is then epoxidized, e.g. by ozonolysis or other suitable oxidant. The epoxidized keto alkyne then can be reduced and internally cyclized, e.g. in the presence of a suitable reducing agent such as diborone methyl sulfide, and then functionalized to compound 1 as generally discussed above.

As mentioned above, compound 1 will be useful for therapeutic applications, and may be employed to treat disorders or diseases mediated by 5-lipoxygenase such as immune, allegeric and cardiovascular disorders and diseases, e.g. general inflammation, hypertension, skeletal-muscular disorders, osteoarthritis, gout, asthma, lung edema, adult respiratory distress syndrome, pain, aggregation of platelets, shock, rheumatoid arthritis, psoriatic arthritis, psoriasis, autoimmune uveitis, allergic encephalomyelitis, systemic lupus erythematosis, acute necrotizing hemmorrhagic encephalopathy, idiopathic thrombocytopenia, polychondritis, chronic active hepatitis, idiopathic sprue, Crohn's disease, Graves ophthalmopathy, primary biliary cirrhosis, uveitis posterior, interstitial lung fibrosis, allergic asthma and inappropriate allergic responses to environmental stimuli.

Compound 1 produced by the methods of the invention will be useful as a synthetic intermediate to prepare other compounds that will be useful for therapeutic applications. Other aspects of the invention are disclosed infra.

DETAILED DESCRIPTION OF THE INVENTION

Particularly preferred preparative methods of the invention are exemplified in the following Schemes I through XIV. For purposes of exemplification only, particularly preferred compounds are depicted in the Schemes, and it will be understood that a variety of other compounds can be employed in similar manner as described below with respect to the exemplified compounds.

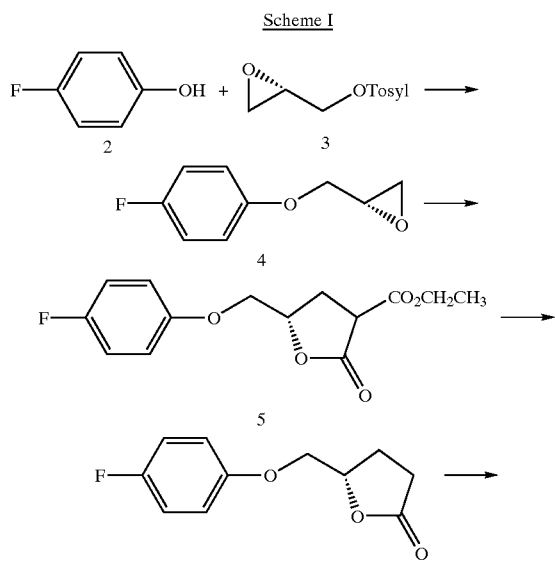

Scheme I

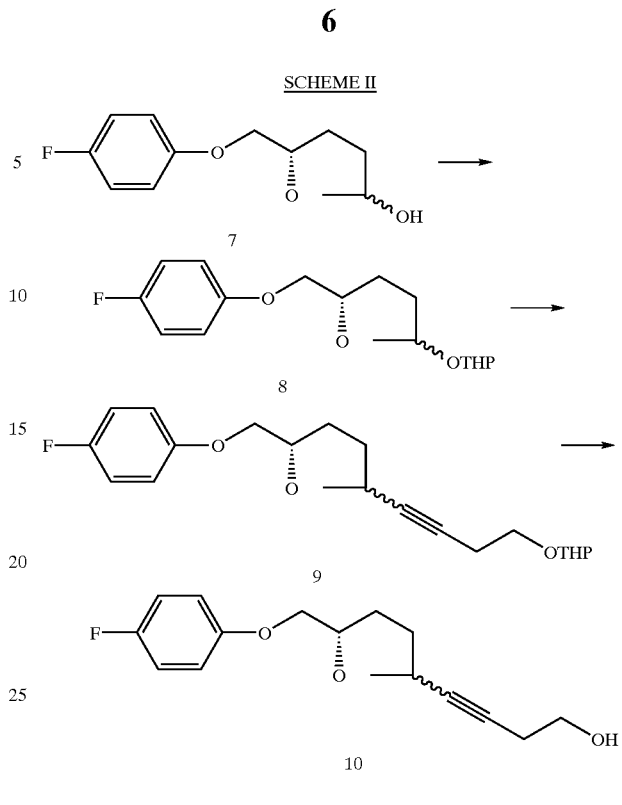

Scheme I exemplifies a preferred preparative method of the invention wherein arylhydroxide 2 is reacted with epoxide 3 having a reactive C3 carbon. Preferred epoxides are those that are enantiomerically enriched, such as the glycidyl tosylate 3 shown above that is condensed with phenol 2 for a time and temperature sufficient for reaction completion to provide epoxyaryl ether 4. See Example 1, Part 1 below for exemplary reaction conditions. The reagents 2 and 3 are typically reacted in a suitable solvent, e.g. dimethyl formamide, N-methyl pyrrolidinone and the like. Enantiomerically enriched epoxides suitable for condensation with an arylhydroxide are commercially available or can be readily prepared by known procedures. See, for instance, U.S. Pat. Nos. 4,946,974 and 5,332,843 to Sharpless et al. for preparation of optically active derivatives of glycidol.

The epoxyaryl ether 4 then is reacted with an active methylene group, such a diethyl or dimethyl malonate to provide butyrolactone 5. The exocyclic ester of 5 is then suitably cleaved, e.g. with reaction with magnesium chloride hexahydrate, to provide the aryllactone ether 6. See Example 1, Part 3 which follows for an exemplary reaction conditions. That lactone 6 is then reduced to the hydroxytetrahydrofuran 7. Suitable reducing agents include e.g. DIBAL-H and the like. See Example 1, Part 4, which follows.

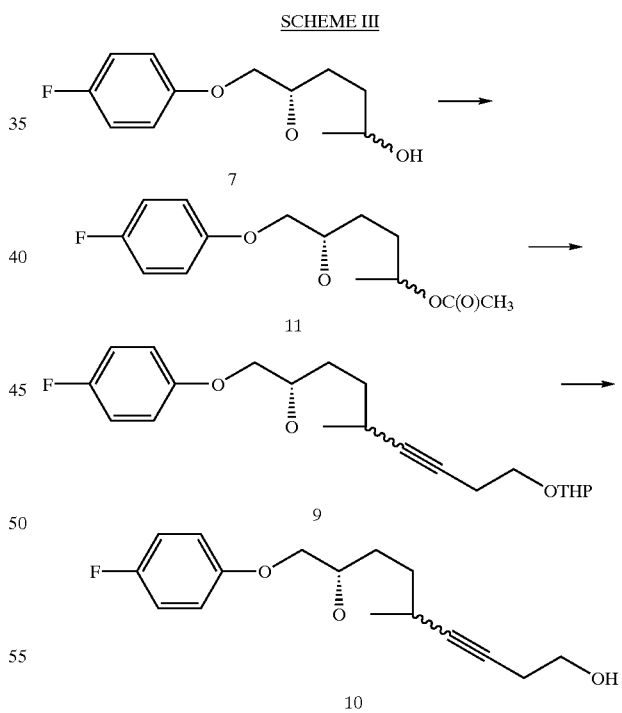

Schemes II and III exemplify further preferred methods of the invention for synthesis of compound 1 and precursors thereof. More specifically, the hydroxy substituent of tetrahydrofuran 7 is preferably protected, e.g. as an ether or ester. Thus, as depicted in Schemes II and III, the hydroxy moiety of 7 can be reacted with a suitable silyl reagent, e.g. to form the t-butyldimethylsilyl ether 8, or with reagent for esterification, e.g. an anhydride such as acetic anhydride to acetyl ester 11. See Example 1, Part 5 and Example 2, Part 1 for suitable reaction conditions for exemplary conditions.

The protected phenyltetrahydrofuran ether 8 or 11 then can reacted to provide the alkynyl-substituted tetrahydrofuran 9 by treatment with a 1-alkyne in the presence of a strong base such an alkyllithium. Preferably the alkyne reagent contains a protected hydroxy moiety such as a silyl ether, e.g. a tetrahydropyranyl ether as depicted in the above Schemes. The hydroxy group can be readily deprotected after coupling of the alkynyl reagent to the tetrahydrofuran ring, e.g. by treatment with dilute acid. Typically, the alkyne reagent will contain a primary or secondary hydroxy moiety.

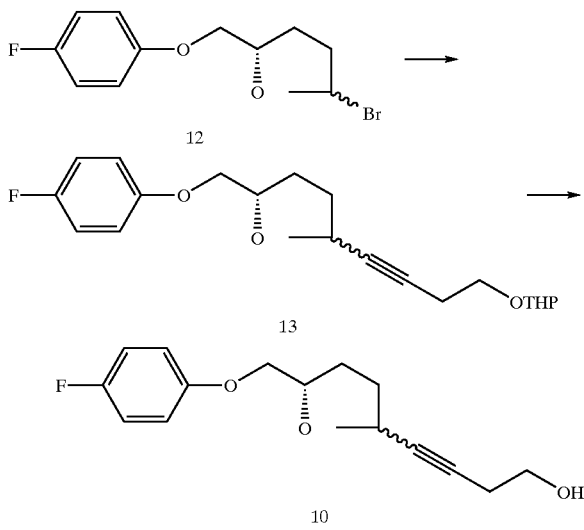

Thus, in Scheme IV, halo-substituted compound 12 can be reacted with an alkyne reagent as generally described above with respect to Schemes II and III to provide 9, which can be readily deprotected to provide the primary alcohol of compound 10. See generally Example 3 which follows for exemplary reaction conditions.

In Scheme V, hydroxytetrahydrofuran 7 is condensed with a sulfinic acid reagent to provide the phenylsulfinic acid ester 8 which can be reacted with an alkyne reagent as generally described above to provide 9. Compound 10 is readily provided by treatment of the protected alcohol 9 with treatment with dilute acid. See Example 4 below.

It also has been found that enhanced yields can be obtained by use of a phenylsulfinic acid reagent that is substituted at one or more positions on the phenyl ring, rather than the unsubstituted phenylsulfinic reagent. Methylphenylsulfinic acid, including p-methylphenylsulfinic acid is particularly preferred, although phenyl ring substituents will be suitable in addition to methyl, including both electron-withdrawing and electron-donating phenyl ring substituents such as one or more $C_{1-12}$alkyl groups more typically one or more $C_{1-8}$alkyl or $C_{1-6}$alkyl groups, $C_{1-12}$ alkoxy or more typically $C_{1-6}$alkoxy, cyano, nitro and the like. Para substitution of the phenyl reagent is generally preferred, although other phenyl ring positions also may be suitably substituted.

Scheme VI below exemplifies a further preferred method of the invention that can provide compound 1 and precursors thereof in high yields and involves cleavage of a bis-compound.

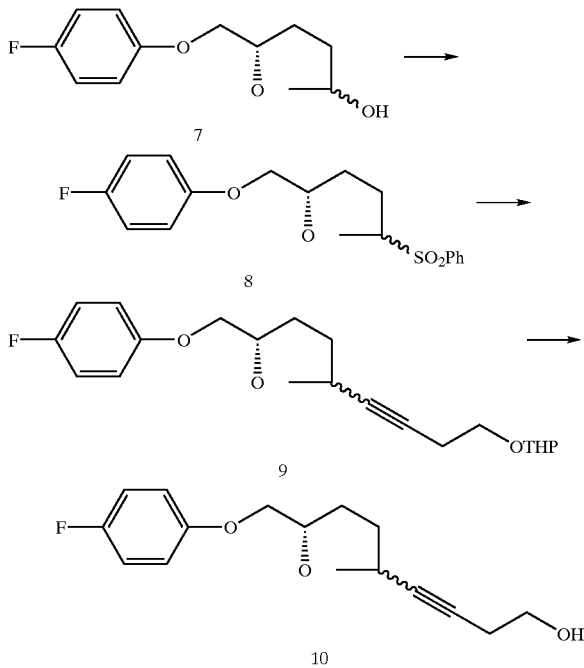

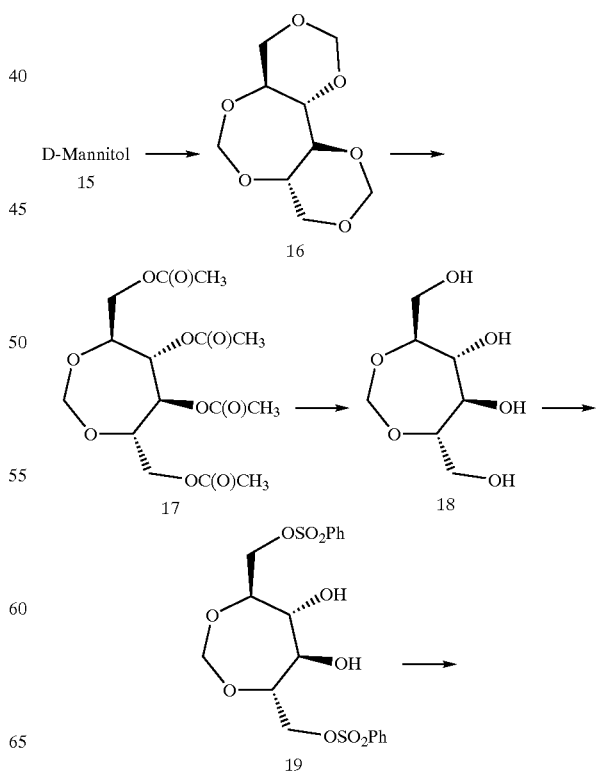

Schemes IV and V above exemplify further convenient routes that can provide compound 1 and precursors thereof.

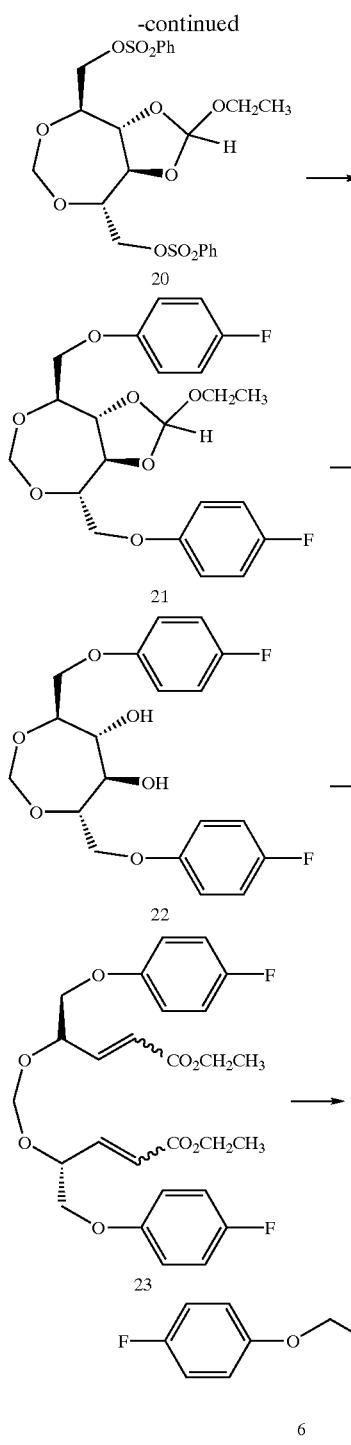

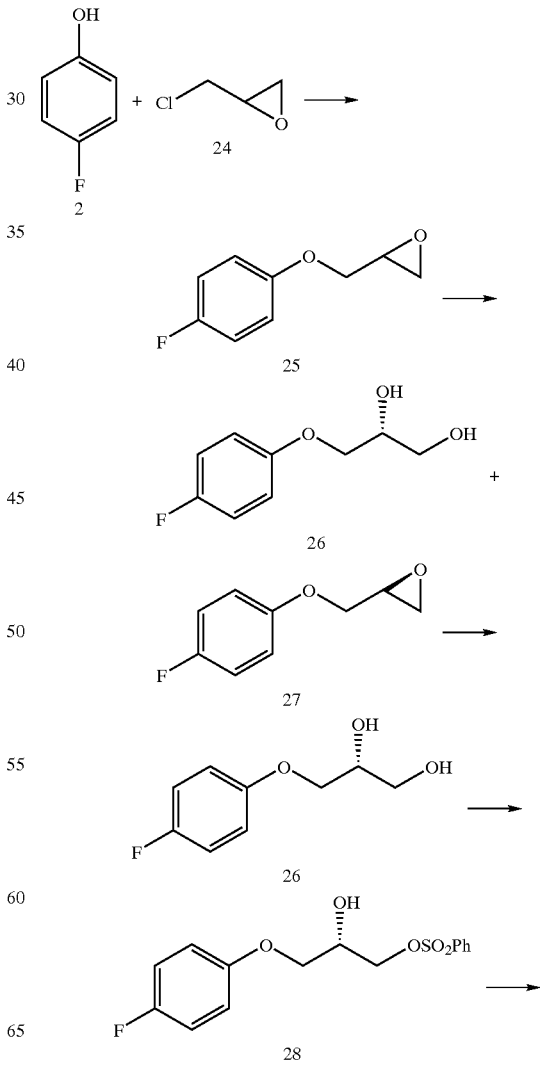

4-fluorophenol to provide di-(4-fluorophenyl)ether 21. That phenyl ether is then reacted in the presence of acid to cleave the methylene ethers to provide secondary hydroxyl groups of compound 22.

Compound 22 then undergoes oxidative cleavage by treatment with a suitable reagent such as Pb(OAc)$_4$, and the resulting dialdehyde is functionalized to the acyclic bis-(α, β-unsaturated) compound, preferably bis-α,β-unsaturated ester 23 such as by reaction with carboethoxymethylenetriphenyl phosphorane. Other α,β-unsaturated groups will be suitable for the alicyclic compound, e.g. α,β-unsaturated esters having 1 to about 12 carbon atoms, α,β-unsaturated acids, and other Michael-type acceptors. The carbon-carbon double bonds of 23 then are saturated, preferably by hydrogenation, and the resulting compound is cleaved and cyclized in the presence of acid to form the aryl ether 6. In one system, the saturated compound is refluxed in a suitable solvent such as an alcohol, ethanol, for a time sufficient to provide 6. See Example 5 which follows for exemplary reagents and reaction conditions. Compound 6 then can be further functionalized, e.g. as discussed above with respect to Schemes II and III.

SCHEME VII

More specifically, as depicted above, trimethylene mannitol 16 is suitably prepared by condensation of mannitol 15 with formaldehyde in the presence of acid. The labile rings are cleaved and the resulting esters of 17 reduced to the primary and secondary alcohols of 18. The primary alcohols are protected, e.g. as an allyl or aryl sulfonic ester, to provide intermediate 19. The secondary hydroxyl groups of 19 then are functionalized by reaction with a trialkylorthoformate, e.g. a tri(C$_{1-10}$alkyl)orthoformate such as triethylorthoformate, to provide 20. The protected primary alcohols of 20 are then converted to 4-fluorophenyl ethers, preferably under basic conditions by reaction with

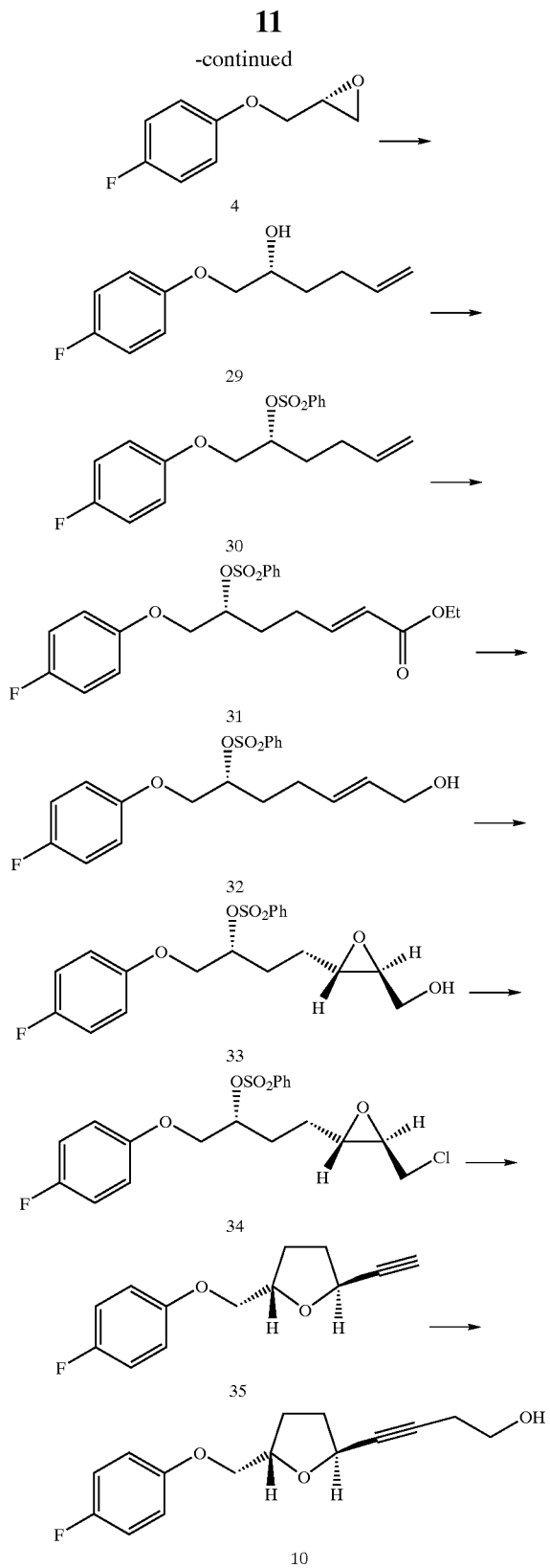

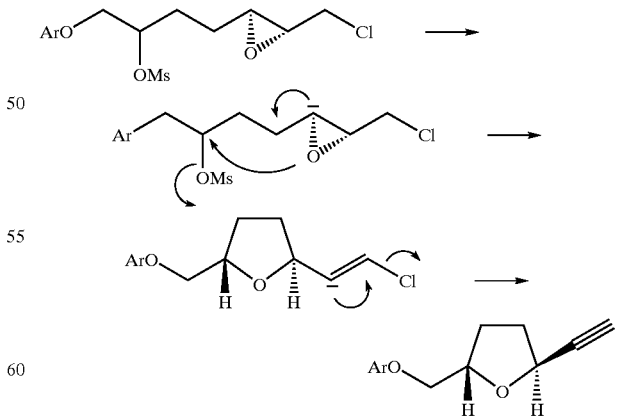

fluorophenylepoxy ether 25. If the epoxide 24 is not enantiomerically enriched such as 3, the fluorophenylepoxy ether 25 may be resolved if desired such as by procedures generally depicted in Scheme VI above to provide optically active epoxide ethers 27 and 4. See Example 6, Parts 2–4 below for exemplary reagents and reaction conditions. That procedure generally entails formation of optically active fluorophenyldiol ether and fluorophenylepoxide ether 26 and 27 from the racemic fluorophenylepoxide 25 with an optically active reagent, preferably an optically active catalyst such as Jacobsen's catalyst. See E. Jacobsen, *Science*, 277:936–938 (1997). The optically active diol 26 can be readily cyclized to the epoxide 4, for example by esterification (e.g. a sulfonic ester as shown exemplified by 28 above) of the primary hydroxyl group of the diol followed by epoxide formation under basic conditions (e.g. NaH).

An allyl halide is suitably reacted with the phenylepoxide ether, suitably in the presence of Mg, catalytic amount of iodine and cuprous cyanide to provide arylalkene ether 29. The secondary hydroxy is suitably protected, e.g. as an ester, preferably as a sulfonic ester, to provide 30. An ester group is then suitably grafted to terminal carbon-carbon double bond to the α,β-unsaturated ester 31, and the ester reduced to the alcohol, typically by treatment with strong base such as DIBAL-H.

The alkene is then suitably oxidized to provide epoxy group of 33. The oxidation may be conducted to provide optically active epoxy carbons as generally shown in Scheme VI (compound 33) and conducted using suitable optically active reagent(s) such as an optically active catalyst or other reagent. See Example 6, Part 9 for an exemplary procedure. The racemic epoxides also may be resolved, e.g. by chromatography using an optically active packing material. The glycidyl compound 33 is then converted to the epihalohydrin 34.

The epihalohydrin 34, in a single step, is converted to the alkynyltetrahydrofuran ether 35 upon treatment with a molar excess, preferably at least about a three molar excess of a strong base such as an alkyllithium reagent or sodium amide. BuLi is generally preferred, particularly n-BuLi.

While not being bound by theory, it is believed the single step reaction proceeds through the mechanism shown immediately below, where Ar is 4-fluorophenyl and Ms is mesyl (—S(O)$_2$CH$_3$):

The alkynyl group of compound 35 can be further functionalized as desired, e.g. by reaction with ethylene oxide in the presence of base to afford the single enantiomer 10. Compound 10 is further functionalized to produce com- Scheme VII above exemplifies a further preferred method of the invention that provides compound 1 and precursors thereof and features multiple reactions that proceed as a single step without isolation of intermediates.

More specifically, as shown above compound 2 is reacted with epoxide 24 that has a reactive C3 carbon to provide the pound 1 suitably by reacting compound 10 with N,O-bisphenoxycarbonyl hydroxylamine and triphenylphosphine and diisopropylazo-dicarboxylate, followed by treatment of resulting intermediate with NH₃.

More preferably, compound 1 is generated from 10 via a protected hydroxyurea (e.g., a compound of the formula NH₂C(O)NHOR, where R is a hydroxy protecting group such as para-methoxybenzyl-) is reacted with a substituted alcohol compound such as 10 of Scheme II, preferably in the presence of suitable dehydrating agent(s) such as triphenyl phosphine and diethylazodicarboxylate (DEAD), to provide an amino ester, i.e. a moiety of the formula —NRC(O)OR¹R where R is as defined immediately above and R¹ is a non-hydrogen group such as aryl, particularly phenyl, alkyl, e.g. C$_{1-10}$ alkyl, etc. That amino ester is then treated with ammonia and a Lewis acid such as boron trifluoride etherate and the like to provide compound 1.

Scheme VIII shows another preferred preparative method of the invention that employs a polyol reagent. As depicted in the below Scheme, the entire reaction is stereoselective (i.e. no separate resolution step or procedure required), beginning with the optically active mannitol 1, which is commercially available. Other glyceraldehyde steroisomers can be employed in the same manner as depicted in Scheme VIII to provide the corresponding distinct stereoisomer as the reaction scheme product.

In the following Schemes VIII through XIV, the compound numerals in the discussions of those Schemes are made in reference to the compound depicted in the particular Scheme, with the exception of compound 1, i.e. 2-(4-fluorophenoxymethyl)-5-(4N-hydroxyureidyl-1-butynyl)-tetrahydrofuran.

As generally exemplified in Scheme VIII below, the chiral synthon (mannitol) is cyclized in the presence of base to the bis-dioxolane compound 2 which is then oxidized to the keto dioxolane 3 and reacted with an appropriate Wittig reagent to provide the α,β-unsaturated ester 4. As referred to herein, unless specified otherwise, the term "Wittig reaction" or "Wittig-type reaction" designates any of the broad classes of alkene-formation reactions, typically involving ylide intermediates such as may be provided by phosphonate and phosphorane reagents. Additionally, as referred to herein, unless otherwise specified, to "keto", "carbonyl", or "carboxy" or like term designate any functional group that includes a carbon-oxygen double bond (C=O).

The carbon-carbon double bond produced by the Wittig reaction then can be saturated, e.g. hydrogenated in the presence of a suitable catalyst such as PtO₂, and the ester reduced and then oxidized to provide aldehyde 7. Wittig reaction of the aldehyde moiety provides the α,β-unsaturated compound 9 which can be reduced to alcohol 9, and converted to the propargyl compound, e.g. via an epoxidized intermediate. More specifically, unsaturated alcohol 9 can be epoxidized to compound 10 suitably with an optically active oxidant and then elimination of the epihalohydrin derivative 11 in the presence of a suitable base e.g. LDA or other suitable agent to provide the propargyl compound 12. Acidic opening of the dioxolane ring provides diol 14 and esterification (e.g., sulfonate ester such as a tosylate) provides the substituted tetrahydrofuran 16. The resulting hydroxy tetrahydrofuran can be functionalized as desired, e.g. esterification of the hydroxy followed by aryl substitution and functionalization of the alkynyl group provides compound 1, particularly 2S,5S-trans-(4-fluorophenoxymethyl)-5-(4-N-hydroxyureidyl-1-butynyl)-tetrahydrofuran. See, generally, Example 7 which follows for exemplary preferred reaction procedures.

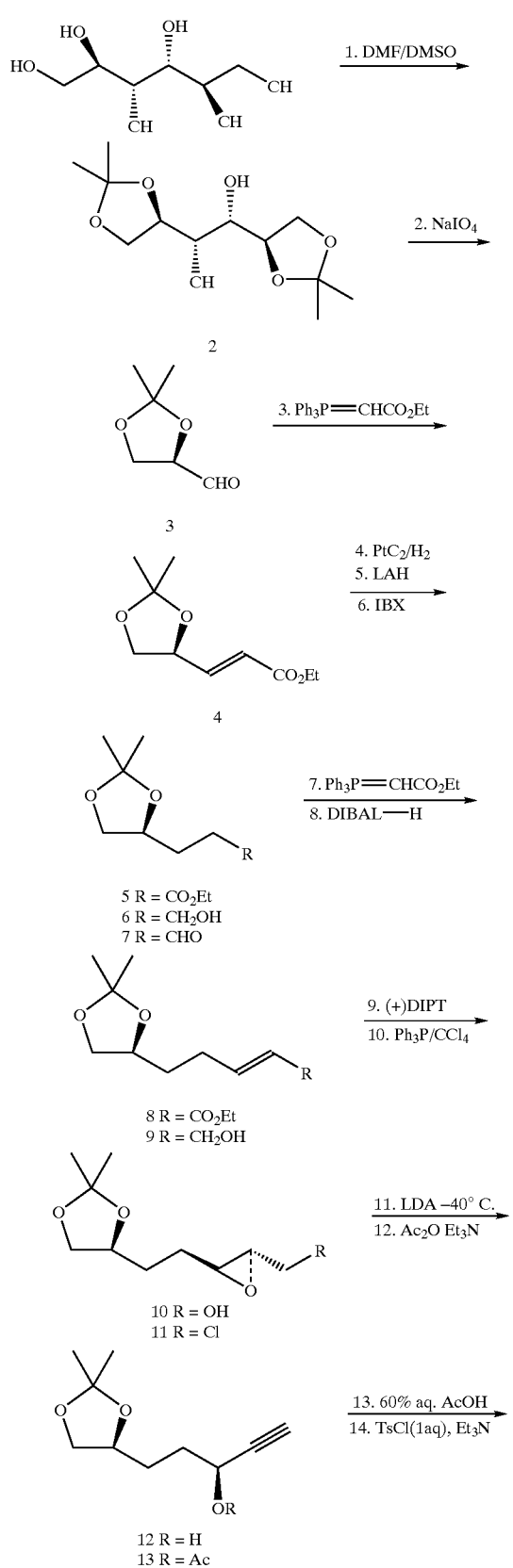

Scheme VIII

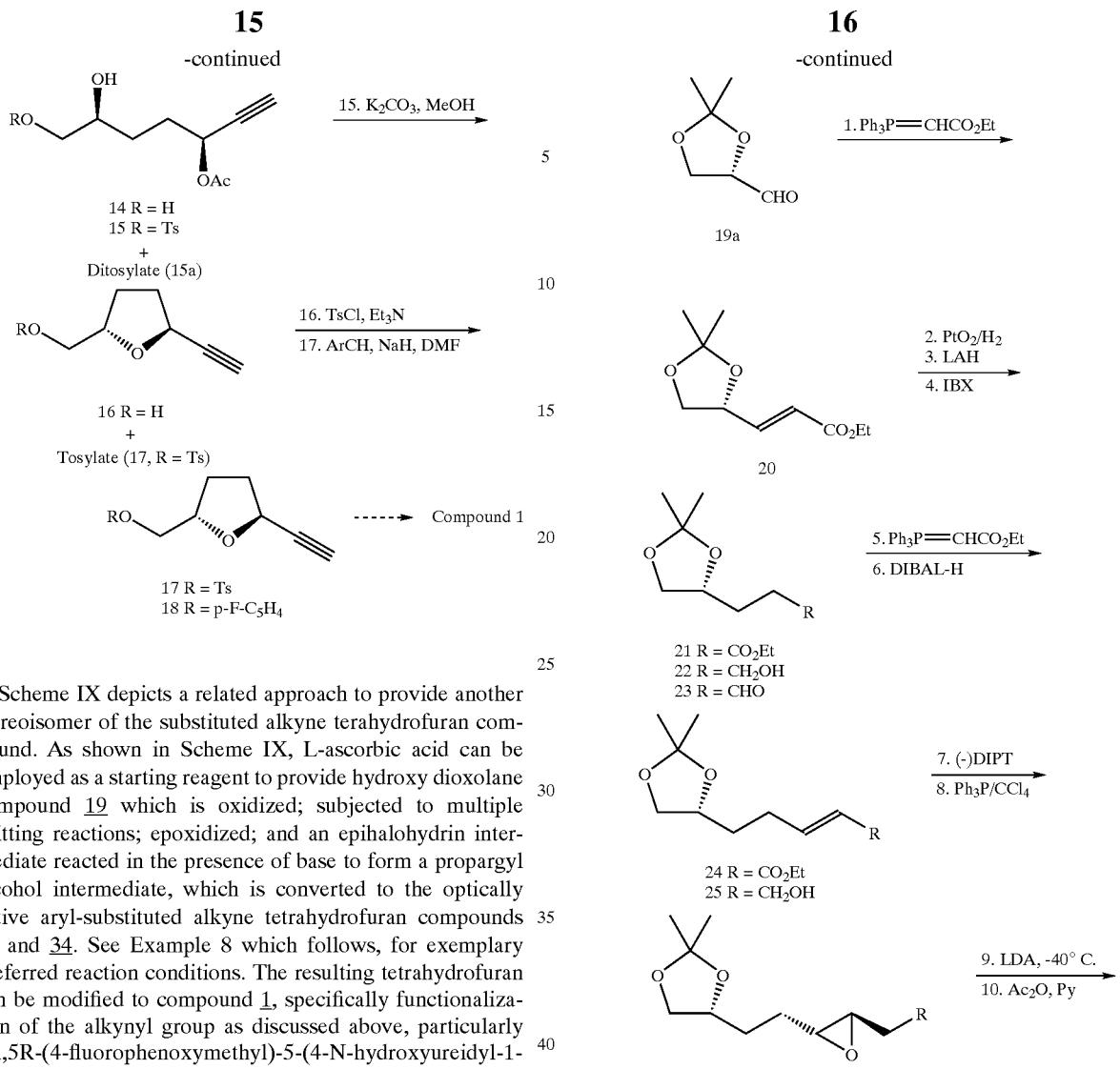

Scheme IX depicts a related approach to provide another stereoisomer of the substituted alkyne terahydrofuran compound. As shown in Scheme IX, L-ascorbic acid can be employed as a starting reagent to provide hydroxy dioxolane compound 19 which is oxidized; subjected to multiple Witting reactions; epoxidized; and an epihalohydrin intermediate reacted in the presence of base to form a propargyl alcohol intermediate, which is converted to the optically active aryl-substituted alkyne tetrahydrofuran compounds 33 and 34. See Example 8 which follows, for exemplary preferred reaction conditions. The resulting tetrahydrofuran can be modified to compound 1, specifically functionalization of the alkynyl group as discussed above, particularly 2R,5R-(4-fluorophenoxymethyl)-5-(4-N-hydroxyureidyl-1-butynyl)-tetrahydrofuran.

Scheme IX

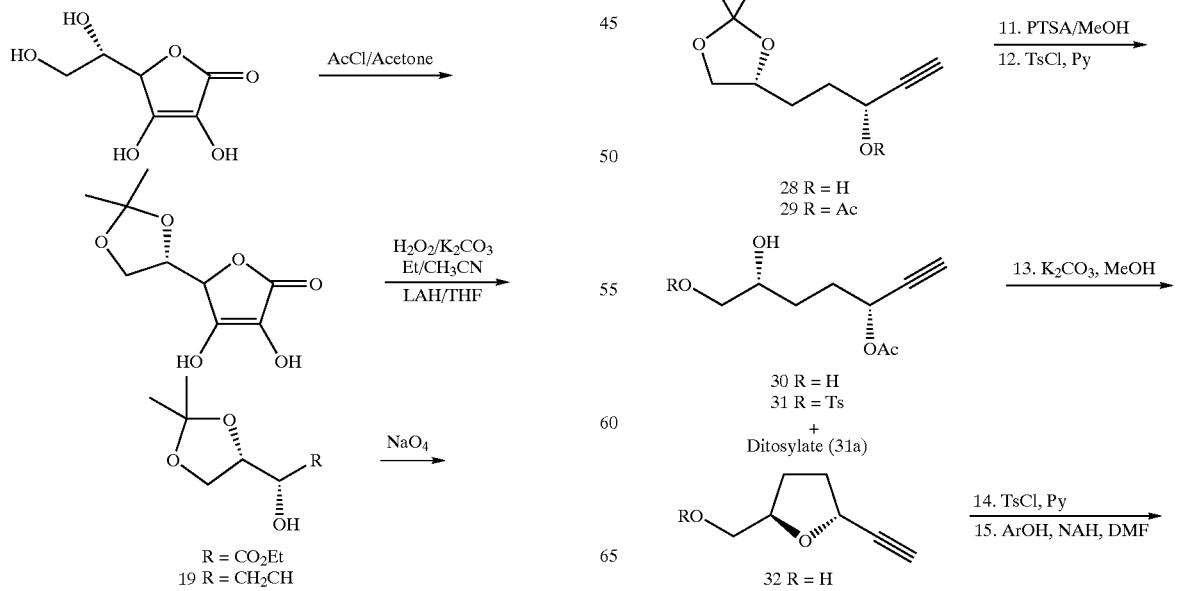

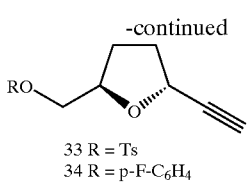

33 R = Ts
34 R = p-F-C₆H₄

---- Compound 1

It should be appreciated that the unsubstituted alkyne produced through the routes of Schemes VIII and IX above is a versatile intermediate that can be further reacted to provide a wide range of moieties, including groups that can be detected, either upon in vitro or in vivo applications. For instance, the unsubstituted alkyne can be reacted with a group to provide radiolabeled and stable isotopic moieties e.g. $^{125}$I, $^{3}$H, $^{32}$P, $^{99}$Tc, $^{14}$C, $^{13}$C, $^{15}$N or the like, which may be useful inter alia for mechanistic studies.

Scheme X below depicts another route related to Schemes VIII and LX above and employs multiple Wittig reactions to provide a further stereoisomer of compound L, specifically 2R,5S-2-(4-fluorophenoxymethyl)-5-(4-N-hydroxyureidyl-1-butynyl)-tetrahydrofuran. See Example 9 which follows for exemplary reaction conditions.

Scheme X

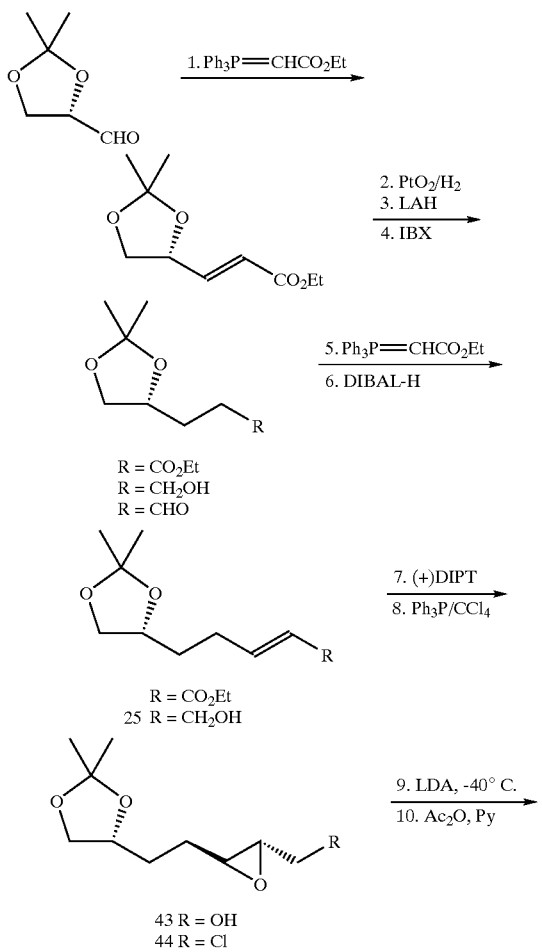

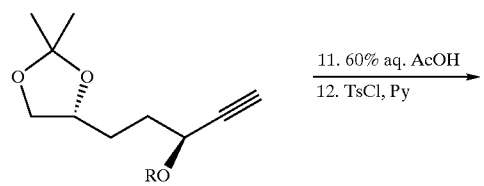

45 R = H
46 R = Ac 11. 60% aq. AcOH
12. TsCl, Py

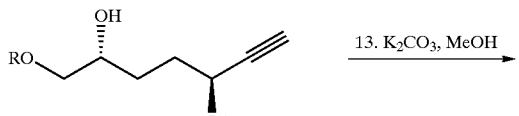

47 R = H
48 R = Ts

13. K₂CO₃, MeOH

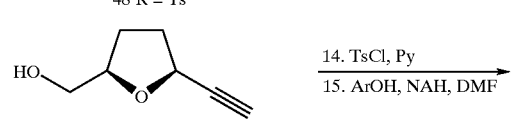

49

14. TsCl, Py
15. ArOH, NAH, DMF

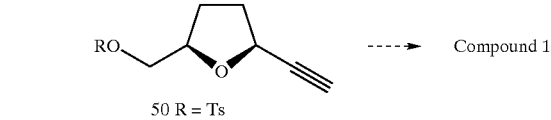

50 R = Ts
51 R = p-F-C₆H₄

---- Compound 1

Scheme XI below exemplifies further methods of the invention that utilize dioxolane intermediate 7. Rather than employing multiple Wittig reactions, a 1-alkyne is reacted with aldehyde reagent 7, the resulting dioxolane 35 esterified and the dioxolane ring opened in the presence of acid, followed by cyclization in the presence of base, suitable a relatively weak base such as K₂CO₃. The cyclization of 38 to optically active substituted tetrahydrofuran 39 can proceed with high stereoselectivity. The resulting tetrahydrofuran then can be further functionalized to provide 2-(4-fluorophenoxymethyl)-5-(4-N-hydroxyureidyl-1-butynyl)-tetrahydrofuran. See Example 10 which follows, for exemplary preferred reaction conditions.

Scheme XI

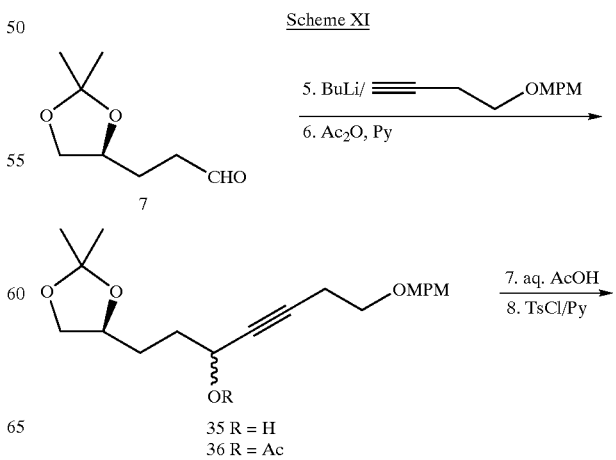

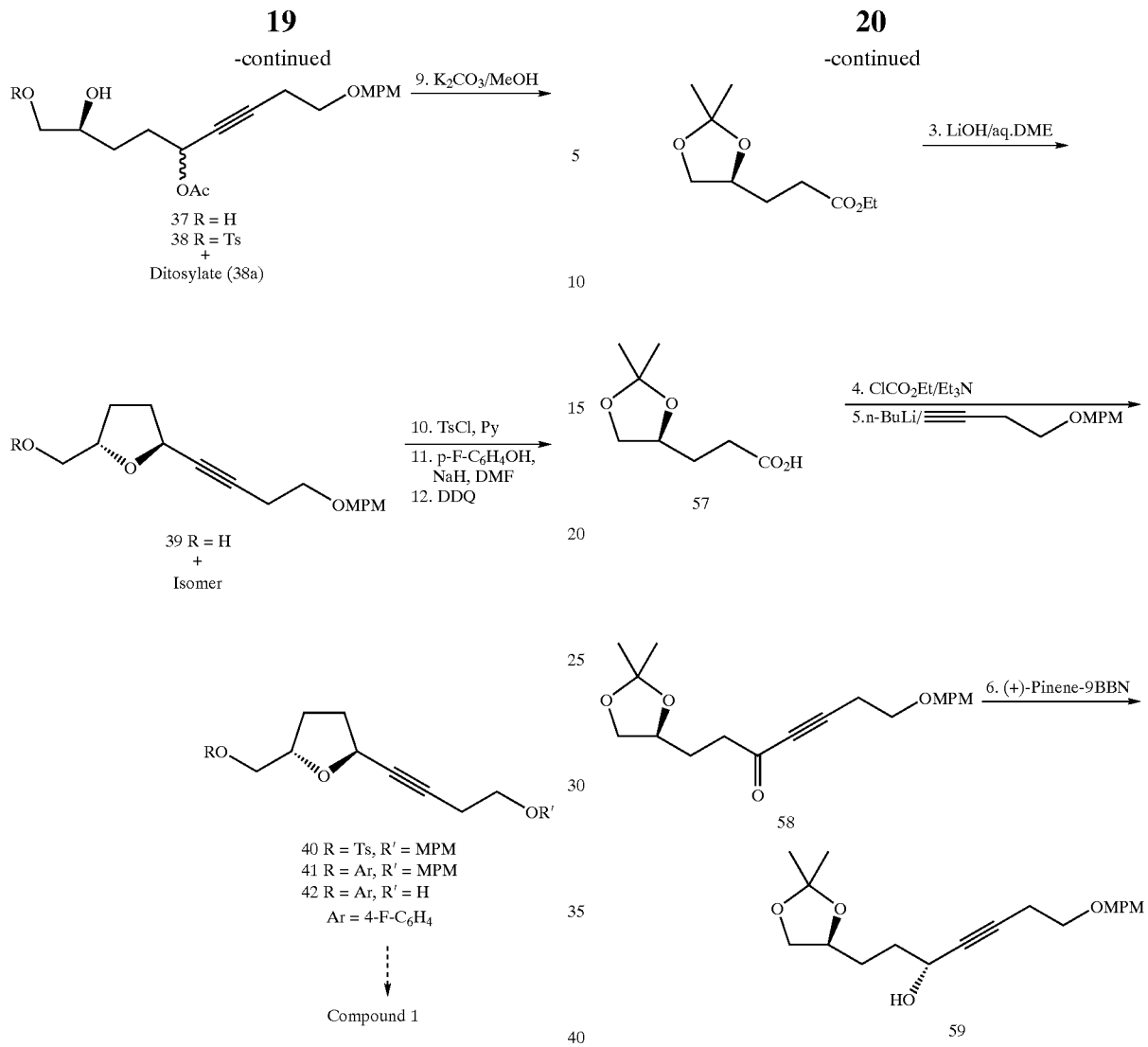

Scheme XII below depicts another convenient route to compound 1 that entails a single Wittig reaction. More particularly, the dioxolane aldehyde reagent is reacted with a Wittig reagent, the resulting alkene saturated such as by hydrogenation and the alkyl ester converted to acid 57. The acid is then reacted with a chloroformate reagent in the presence of base, and the resulting intermediate reacted with 1-(4-methoxy phenylmethylether)-butynyl in the presence of a strong base, such as an alkyl lithium e.g. butyllithium. The keto alkyne dioxolane compound 58 is then reduced asymmetrically in the presence of a suitable chiral catalyst, e.g. an optically active pinene and BBN. The resulting optically active propargyl alcohol can be reacted as outlined above to provide compound 1, particularly 2S,5S-trans-2-(4-fluorophenoxymethyl)-5-(4-N-hydroxyureidyl-1-butynyl)-tetrahydrofuran. See Example II which follows for exemplary reaction conditions.

Scheme XII

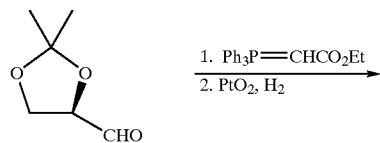

Scheme XIII below depicts a highly efficient route to 2-(4-fluorophenoxymethyl)-5-(4-N-hydroxyureidyl-1-butynyl)-tetrahydrofuran. As shown in the Scheme, butynyl reagent 52 is treated with base, preferably a strong base such as an alkyl lithium e.g. butyl lithium, and then reacted with an unsaturated anhydride 53 to provide the keto alkynyl compound 54 with terminal alkene group. The alkene group is oxidized, e.g. via ozonolysis, and the keto-epoxide compound 55 reduced and cyclized typically in the presence of a suitable reducing agent, e.g. diborane methyl sulfide. The resulting hydroxy tetrahydrofuran can be functionalized as desired, e.g. esterification of the hydroxy moiety followed by aryl substitution and functionalization of the alkynyl Croup provides 2-(4-fluorophenoxymethyl)-5-(4-N-hydroxyureidyl-1-butynyl)-tetrahydrofuran. See Example 12 which follows for exemplary preferred reaction conditions.

Scheme XIII

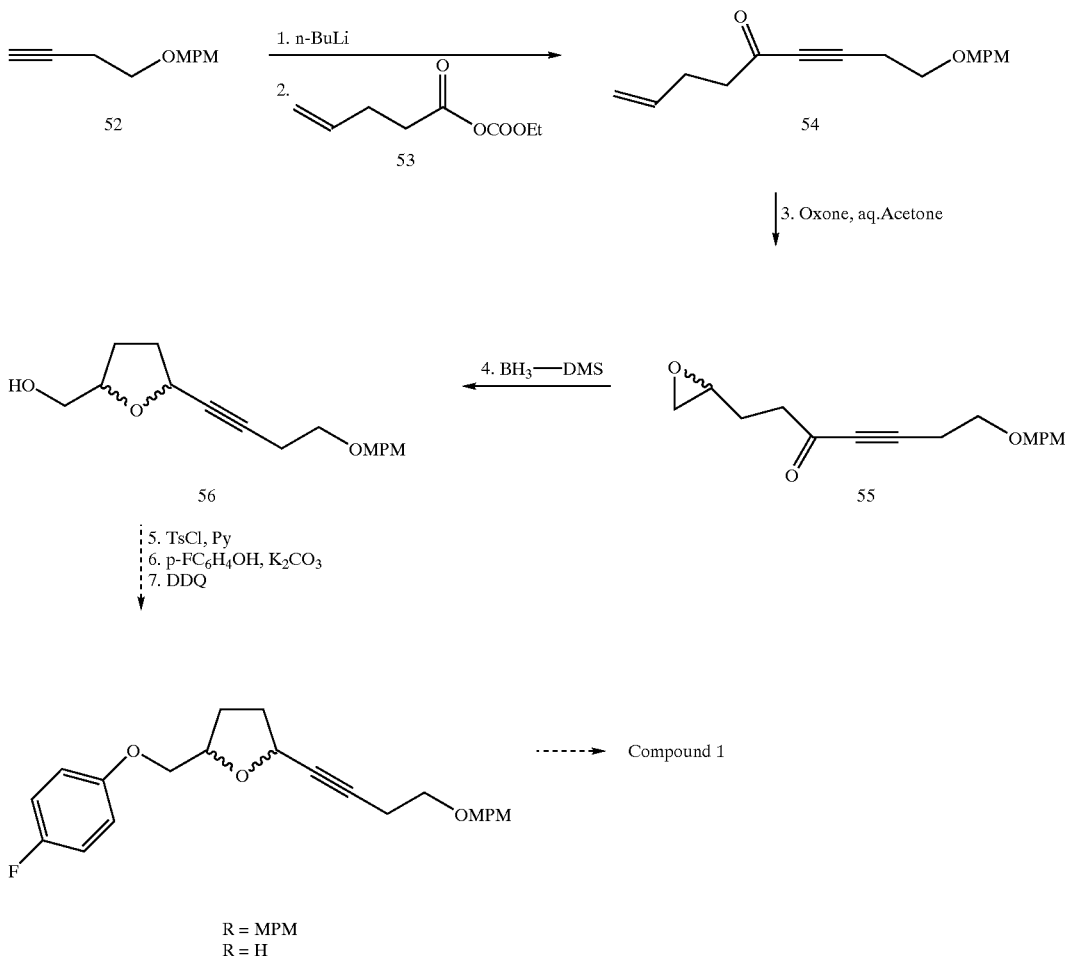

R = MPM
R = H

In another aspect of the invention, it has been found that that a lactone, particularly butyrolactone such as γ-butyrolactone ring-substituted (suitably at an α position) by an activated ester (e.g., sulfonate ester such as tosylate, mesylate, etc.) can be reacted with an aryl nucleophile to provide in good yields a methylene aryloxy group. More specifically, with reference to Scheme XIV below, compound 60 will undergo a displacement reaction with an aryl nucleophile in the presence of a hydride reagent (base), such as potassium hydride or more preferably sodium hydride to yield the tetrahydrofuran arylether 61. Preferred aryl nucleophiles include aryl compounds having one or more hydroxy ring substituents (i.e. an aryl hydroxy compound), particularly carbocyclic aryl compounds such as phenol, particularly 4-fluorophenol. See Example 13 which follows for exemplary preferred reaction conditions. It has been found that this substitution reaction proceeds without opening or other undesired attack of the lactone ring. In Scheme XIV, the substituent R is compound 60 is suitably hydrogen, alkyl e.g. $C_{1-8}$ alkyl and the like; and the substituent R' is suitably aryl as specified herein, particularly phenyl, more preferably 4-fluorophenyl. Compound 60 can be readily functionalized to provide compound 1, particularly by the procedures discussed above with respect to Schemes I and II.

SCHEME XIV

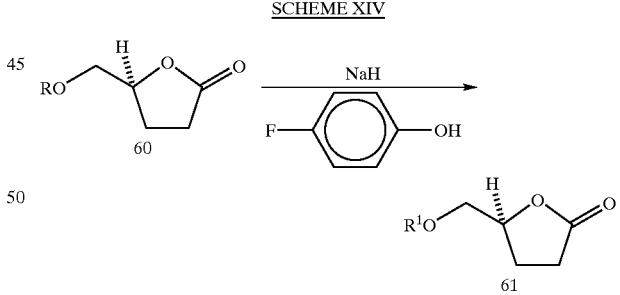

As discussed above, compound 1 will be useful for numerous therapeutic applications. The compounds can be administered to a subject, particularly a mammal such as a human, in need of treatment, by a variety of routes. For example, the compound can be administered orally, parenterally, intravenously, intradermally, subcutaneously, or topically.

The active compound may be administered to a subject as a pharmaceutically active salt, e.g. salts formed by addition of an inorganic acid such as hydrochloric acid, hydrobromic acid, phosphoric acid, etc., or an organic acid such as acetic acid, oxalic acid, tartaric acid, succinic acid, etc. Base addition salts also can be formulated if an appropriate acidic group is present on the compound. For example, suitable base addition salts include those formed by addition of metal cations such as zinc, calcium, etc., or salts formed by addition of ammonium, tetraethylammonium, etc. Suitable dosages for a given therapy can be readily determined by the medical practitioner such as by standard dosing protocols. See also U.S. Pat. No. 5,703,093.

Often, it will be preferable to use an optically active or enantiometrically enriched mixture of compound 1 for a given therapeutic application. As used herein, the term "enantiometrically enriched" typically refers to a compound mixture that is at least approximately 70 mole %, 80 mole %, 85 mole % or 90 mole % of a single stereoisomer, and preferably a compound mixture that contains approximately at least about 92 mole %, 95 mole %, 97 mole %, 98 mole %, 99 mole % or 100% of a single enantiomer of the compound.

As used herein, the term halo, halogen or the like refers to fluoro, chloro, bromo or iodo. The term alkyl typically refers an alkyl group having 1 to about 20 carbon atoms, more typically 1 to about 12 carbon atoms, still more typically 1 to about 6 or 8 carbon atoms. The term arylalkyl refers to a carbocyclic aryl such as phenyl that is substituted on an alkyl, particularly alkyl having 1 to about 6 to 8 carbons.

All documents mentioned herein are incorporated herein by reference.

The following non-limiting examples are illustrative of the invention.

EXAMPLE 1

Preparation of (2S)(5R)-2-(4-fluorophenoxymethyl)-5-(4-hydroxybutyn-1-yl)-tetrahydrofuran (Scheme II; 10)

Part 1: (S)-Glycidyl-4-fluorophenyl Ether (Scheme I; 4)

In a 100 ml two-necked round bottom flask equipped with magnetic stir bar, nitrogen inlet and a septum, was taken sodium hydride (60% dispersion in oil, 0.742 g, 0.0185 mol) and 10 mL of dry dimethyl formamide (DMF). The reaction mixture was cooled to 0° C. and 4-fluorophenol 2 (1.9 g, 0.017 mol) in dry DMF (20 mL) was introduced. The reaction mixture was stirred at room temperature for 1 hour and cooled to 0° C. (S)-Glycidyl tosylate 3 (3.52 g, 0.015 mol) in DMF (10 mL) was added, and the reaction mixture was stirred at room temperature and monitored by TLC (EtOAc-light petroleum ether 1:4, Rf=0.5). After 4 hours, the reaction mixture was quenched by addition of ice-water (1 mL) and extracted with (2×25 mL) ethyl ether. The ether layer was washed with water, brine, dried over $Na_2SO_4$ and concentrated under reduced pressure to afford (S)-glycidyl-4-fluorophenyl ether 4 crude yield 3.6 g. The crude compound was purified by distillation at 160°–170° C./9 mm, to yield 1.98 g (76%) of purified product 4, $[\alpha]_D$+4.96° (c 2.335, $CHCl_3$). $^1H$ NMR (200 MHz, $CDCl_3$): δ2.68 (dd, J=4.5, 2.2 Hz, 1H), 2.85 (t, J=4.5 Hz, 1H), 3.27 (m, 1H), 3.89 (dd, J=15.7, 6.7 Hz, 1H), 4.11 (dd, J=15.7, 4.5 Hz, 1H), 6.74–7.02 (m, 4H).

Part 2: (4S)-2-carboethoxy-(4-fluoro-phenoxy-methyl)-γ-butyrolactone (Scheme I; 5)

In a 50 ml two-necked round bottom flask equipped with magnetic stir bar, nitrogen inlet septum, sodium salt of diethyl malonate (prepared from 1.8 mL/0.0118 mol of diethyl malonate and 0.245 g/0.0106 mol of sodium) in dry THF (10 mL) was taken. The reaction mixture was cooled to 0° C. and (S)-glycidyl-4-fluorophenyl ether 4 (1.788 g, 0.0106 mol) in tetrahydrofuran (THF) (10 mL) was added. The reaction mixture was stirred at room temperature and monitored by TLC, (EtOAc-light petroleum 1:3, Rf=0.30). After 12 hours, THF was removed on rotavapor. The residue was dissolved in ethyl acetate (25 mL) and washed with water, brine, dried over $Na_2SO_4$ and concentrated on rotavapor to afford (4S)-2-carboethoxy-(4-fluoro-phenoxy-methyl)-γ-butyrolactone 5 with a crude yield of 2.816 g. That crude product was purified on silica gel column chromatography using EtOAc-light petroleum ether (1:8) to provide 2.10 g (70%) of purified product 5, m.p.69–71° C., $[\alpha]_D$+16.950° (c 1.51, $CHCl_3$). $^1H$ NMR (200 MHz, $CDCl_3$): δ1.3 (m, 3H), 2.37–2.9 (m, 2H), 3.52–3.8 (m, 1H), 3.95 4.32 (m, 4.68–4.82 (m, 1/3H), 4.82–4.98 (m, 2/3H), 6.72–7.01 (m, 4H). It is also noted that the crude product can be suitably employed directly in the decarboxylative elimination of Part 3 below.

Part 3: (4S)-4-fluorophenoxy-methyl)-γ-butyrolactone (Scheme I; 6)

(4S)-2-carboethoxy-(4-fluoro-phenoxy-methyl)-γ-butyrolactone 5 (2.1 g, 0.0074 mol) and N,N-dimethylacetamide (10 mL) were taken in a 25 mL round bottom flask equipped with a stir bar and reflux condenser. $MgCl_2.6H_2O$ (1.51 g, 0.0074 mol) was added, and the reaction mixture was heated under reflux for 4 hours and monitored by TLC (EtOAc-light petroleum 1:2, Rf=0.2). The reaction mixture then was partitioned between ethyl ether and water (50 mL each). The ether layer was separated, washed twice with water, brine, dried over $Na_2SO_4$ and concentrated on rotavapor to afford (4S)-4-fluorophenoxy-methyl)-γ-butyrolactone 6, yield 1.40 g (90%), m.p. 58–59° C., $[\alpha]_D$+23° (c 1.99, $CHCl_3$), e.e. 92%. $^1H$ NMR (200 MHz, $CDCl_3$): δ2.13–2.80 (m, 4H), 4.02 (dd, 1H, J=4.5, 9.0 Hz), 4.11 (dd, 1H, J=4.5, 9.0 Hz), 4.80 (m, 1H), 6.75=7.02 (m, 4H).

Part 4: (2S)-(4-Fluorophenoxymethyl)-5-hydroxytetrahydrofuran (Scheme I; 7)

A flame dried 100 mL two neck round bottom flask equipped with a magnetic stir bar and nitrogen inlet was charged with a solution of 3.5 g (0.0167 mol) of (4S)-4-fluorophenoxy-methyl)-γ-butyrolactone 6 in 30 mL of $CH_2Cl_2$. That solution was cooled to −78° C. and 7.34 mL (0.018 mol) diisobutylaluminum hydride (DIBAL-H; 2.5M solution in hexane) was added dropwise. The reaction mixture was stirred at −78° C. for 3 hours. The reaction mixture was quenched with methanol (5 mL) and saturated aqueous solution of potassium sodium tartrate. The organic layer was separated, dried over $Na_2SO_4$ and concentrated on rotavapor to provide (2S)-(4-fluorophenoxymethyl)5-hydroxytetrahydrofuran 7 as a solid (3.47 g). This crude lactol was used in the next reaction (Part 5) without further purification.

Part 5: (2S) (4-fluorophenoxymethyl)-5-(tert-butyldimethylsiloxy)-tetrahydrofuran) (Scheme II; 8)

A solution of 3.47 g of (2S)-(4-fluorophenoxymethyl)-5-hydroxytetrahydrofuran 7 in 30 mL of $CH_2Cl_2$ was taken in an 100 mL round bottom flask equipped with a magnetic stir bar and nitrogen inlet. That solution was cooled in an ice-water bath and 2.18 g (0.032 mol) of imidazole was added, followed by a solution of 3.6 g (0.024 mol) of tert-butyldimethylsilylchloride (TBDMSCl) in 30 mL of $CH_2Cl_2$. The reaction mixture then was stirred at room temperature for 3 hours, and the reaction then quenched with ice water, the organic layer separated, dried over $Na_2SO_4$ and concentrated under reduced pressure. The residue was purified by column chromatography using light petroleum ether:ethyl acetate (9:1) to yield (2S) (4-fluorophenoxymethyl)-5-(tert-butyldimethylsiloxy)-tetrahydrofuran 8 as an oil (5.1 g, 95%). $^1H$ NMR (200 MHz, $CDCl_3$): δ0.09 (s, 6H), 0.88 (s, 9H), 1.72–2.34 (m, 4H), 3.76=4.08 (m, 2H), 4.28–4.54 (m, 1H), 5.47. (s, 1/3H), 5.54 (d, J=4.5 Hz, 2/3H), 6.75–7.0 (m, 4H).

Part 6: (2S) (5SR) (4-fluorophenoxymethyl)-5-(1-butynyl-4-tert-butyldimethylsiloxy)-tetrahydrofuran (Scheme II; 9)

To a flame dried 100 mL two neck round bottom flack equipped with a magnetic stir bar and nitrogen inlet and septum was added a solution of 5 g (0.0154 mol) of (2S) (4-fluorophenoxymethyl)5-(tert-butyldimethylsiloxy)-tetrahydrofuran 8 in 25 mL of $CH_2Cl_2$. That solution was cooled to −78° C. and 2.82 mL (0.0184 mol) of trimethylsilylbromide (TMSBr) was added dropwise. The reaction mixture was then stirred at −78° C. for 3 hours.

In a separate flame dried 50 mL two neck round bottom flask equipped with a magnetic stir bar, nitrogen inlet and septum was added a solution of 3.4 g (0.0184 mol) of 4-tert-butyl-dimethylsiloxy-1-butyne in 30 mL of THF. That solution was cooled to −78° C. and 15.4 mL (1.5M solution in hexane; 0.023 mol) of n-BuLi was added dropwise. That reaction mixture was stirred at −78° C. for 1 hour, and then transferred via syringe to the TMSBr solution. The combined solutions were stirred at −78° C. for 2 hours, and then the reaction quenched with saturated ammonium chloride solution (20 mL) and the organic layer separated. The aqueous layer was extracted with $CH_2Cl_2$ and the combined organic layers were dried over $Na_2SO_4$ and then concentrated under reduced pressure to afford (2S) (5SR) (4-fluorophenoxymethyl)-5-(1-butynyl-4-tert-butyldimethylsiloxy)-tetrahydrofuran 9 as a thick syrup (6.0 g; 97%).

Part 7: (2S) (5RS)-2-(4-Fluorophenoxymethyl)-5-(4-hydroxybutyn-1-yl)-tetrahydrofuran (Scheme II; 10)

Without further purification, (2S) (5SR) (4-fluorophenoxymethyl)-5-(1-butynyl-4-tert-butyldimethylsiloxy)-tetrahydrofuran 9 as prepared in Part 6 above was dissolved in 25 mL of methanol in a 50 mL single neck round bottom flask. That methanol solution was cooled in an ice-water bath and 3 mL of 1% HCl solution in methanol was added. The reaction mixture was then stirred at room temperature for 3 hours, followed by neutralization with saturated aqueous sodium bicarbonate solution. After removal of methanol under reduced pressure, the resulting residue was dissolved in 100 mL of ethyl acetate. The organic layer was washed with water and brine, dried over $Na_2SO_4$ and concentrated under reduced pressure. The residue was purified by column chromatography using light petroleum ether:ethyl acetate (1:1) to provide (2S) (5RS)-2-(4-fluorophenoxymethyl)-5-(4-hydroxybutyn-1-yl)-tetrahydro furan 10 as a thick syrup (4.0 g, 96%). $^1H$ NMR (200 MHz, $CDCl_3$): 67 1.76–2.32 (m, 4H), 2.46 (dt, 2H, J=2.2, 6.7 Hz), 3.69 (t, 2H, J=6.7 Hz), 3.89 (d, 2H, J=4.5 Hz), 4.41 (m, 1H), 4.70 (m, 1H), 6.73–6.98 (m, 4H).

EXAMPLE 2

Alternate Preparation of (2S) (5RS)-2-(4-fluorophenoxymethyl)-5-(4-hydroxybutyn-1-yl)-tetrahydrofuran (Scheme III; 10)

Part 1: (2S) (5RS)-5-0-acetyl-2-(4-fluoro-phenoxymethyl) tetrahydrofuran (Scheme III; 11).

To a 25 ml round bottom flask with magnetic stir bar, (2S) (5RS)-2-(4-fluorophenoxymethyl)-5-hydroxy tetrahydrofuran 7 (1.0 g, 0.0047 mol) in $CH_2Cl_2$ (5 mL) was added. The solution was cooled in an ice-bath, pyridine (0.8 mL), acetic anhydride (0.9 mL) and DMAP (catalytic amount) were added in succession. The reaction was monitored by TLC (EtOAc-light petroleum ether 1:3, Rf=0.5). The reaction mixture was diluted with $CH_2Cl_2$ (10 mL) washed with 5% HCl, brine and dried over $Na_2SO_4$. The solvent was removed on rotavapor to give (2S) (5RS)-5-O-acetyl-2-(4-fluoro-phenoxymethyl) tetrahydrofuran 11 (1.05 g, 88%). $^1H$ NMR (200 MHz, $CDCl_3$): δ1.98, 2.05 (2s, 3H), 1.89–2.3 (m, 4H), 3.85–4.09 (m, 2 H), 4.36–4.61 (m, 1H), 6.26 (s, ½ H), 6.33 (d, J=4.5 Hz, ½ H), 6.75–7.01 (m, 4H).

Part 2: (2S) (5SR) (4-fluorophenoxymethyl)-5-(1-butynyl-4-tert-butyldimethylsiloxy)-tetrahydrofuran (Scheme III; 9).

To a flame dried 25 ml two-necked round bottom flask equipped with magnetic stir bar, nitrogen inlet and a septum, was added a solution of (2S) (5RS)-2-(4-fluorophenoxy-methyl)-5-O-acetyl tetrahydrofuran 11 (1.05 g, 0.004 mol) in $CH_2Cl_2$ (12 mL). The solution was cooled to 78° C. and TMS-Br (0.65 ml, 0.0049 mol) was added dropwise. The reaction mixture was stirred at −78° C. for 3hours (monitored by TLC, EtOAc-light petroleum 1:4, Rf=0.4). In a separate flame dried 50 mL two-necked round bottom flask equipped with magnetic stir bar, nitrogen inlet and a septum, a solution of 4-tert-butyldimethylsiloxy-1-butyne (0.913 g, 0.0049 mol) in THF (15 mL) was taken. The solution was cooled to −78° C. and n-BuLi in hexane (1.5M, 4.13 mL, 0.0062 mol) was added dropwise. The reaction mixture was stirred at −78° C. for 1 hour. This solution was transferred via cannula to the reaction mixture of step 3 at −78° C. The reaction was monitored by TLC (EtOAc-light petroleum 1:4, Rf=0.7) and completed in 2 hours. The reaction mixture was quenched with saturated ammonium chloride solution (10 mL). THF was removed under reduced pressure and extracted with $CH_2Cl_2$ (2×10 mL) dried over $Na_2SO_4$ and concentrated, to provide a crude yield of 1.7 g of (2S) (5SR) (4-fluorophenoxymethyl)-5-(1-butynyl-4-tert-butyldimethylsiloxy)-tetrahydrofuran 9.

Part 3: (2S) (5RS)-2-(4-Fluorophenoxymethyl)-5-(4-hydroxybutyn-1-yl)-tetrahydrofuran (Scheme III; 10)

The crude product 9 (1.7 g) as prepared in Part 2 above was dissolved in methanol (10 mL), and 1% HCl solution in methanol (5 mL) was added. After 3 h the reaction mixture was neutralized with saturated aqueous sodium bicarbonate. After removal of methanol on rotavapor, the residue was dissolved in ethyl acetate (15 mL). The EtOAc fraction was washed with water, brine, dried over $Na_2SO_4$ and concentrated on rotavapor. The residue afforded (2S) (5Rs)-2-(4-fluorophenoxymethyl)-5-(4-hydroxybutyn-1-yl)-tetrahydrofuran 10 as a thick syrup (0.957 g, 88%).

EXAMPLE 3

Further alternate preparation of (2S) (5RS)-2-(4-fluorophenoxymethyl)-5-(4-hydroxybutyn-1-yl)-tetrahydrofuran (Scheme IV; 10)

Part 1: (2S) (5RS)-5-bromo-2-(4-fluorophenoxymethyl)tetrahydrofuran (Scheme IV; 12)

(2S) (5RS)-5-bromo-2-(4-fluorophenoxymethyl) tetrahydrofuran was prepared from (2S) (5RS)-5-O-acetyl- 2-(4-fluorophenoxymethyl)tetrahydrofuran 11 (1.06 g, 0.00417 mol) and TMS-Br (0.65 mL, 0.0049 mol).

Part 2: (2S) (5RS)-2-(4-fluorophenoxymethyl)-5-(4-tetrahydropyranoyloxybutyn-1-yl)-tetrahydrofuran (Scheme IV; 13)

In a flame dried 50 mL two-necked RB flask equipped with a magnetic stir bar, nitrogen inlet and a septum 4-tetrahydropyranoyl-1-butyne (0.774 g, 0.005 mol) in THF (10 mL) was taken and cooled to −78° C. A solution of n-BuLi in hexane (1.5 M, 4.2 mL, 0.0063 mol) was added dropwise, and the reaction mixture was stirred at −78° C. for 1 hour. This solution was transferred via cannula to the reaction mixture of Part 1 of this example at −78° C. That reaction mixture was stirred at −78° C. for 2 h and monitored by TLC (EtOAc-light petroleum 1:4, Rf=0.7). The reaction mixture was quenched with saturated ammonium chloride solution and TDU was removed on rotavapor. The residue was partitioned between $CH_2Cl_2$ (20 mL) and water, and the organic layer was separated, washed with water, brine dried over $Na_2SO_4$ and concentrated on rotavapor to provide a crude yield of 1.73 g.

Part 3: (2S) (5RS)-2-(4-fluorophenoxymethyl)-5-(4-hydroxybutyn-1-yl)-tetrahydrofuran (Scheme IV; 10)

That crude product 13 (1.73 g) was dissolved in MeOH (10 mL) and 1% HCl in methanol (5 mL) was added. After 2.5 h, the reaction mixture was quenched by saturated aqueous $NaHCO_3$, and concentrated under reduced pressure. The residue was dissolved in EtOAc (20 mL), washed with water, brine, dried over $Na_2SO_4$ and concentrated to give (2S) (5RS)-2-(4-fluorophenoxymethyl)-5-(4-hydroxybutyn-1-yl)-tetrahydrofuran 10 (1.03 g, 93%). HPLC analysis: Column ODS; flowrate: 1.0 mL/min.; UV: 225 nm. Mobile phase 60% methanol in water. Trans:cis ratio (65:35).

EXAMPLE 4

Further Alternate Preparation of (2S)(5RS)-2-(4-fluorophenoxymethyl)-5-(4-hydroxybutyn-1-yl)-tetrahydrofuran (Scheme V: 10)

Part 1: (2S) (5RS)-5-benzenesulfonyl-2-(4-fluorophenoxymethyl)tetrahydrofuran (Scheme V; 14)

To benzenesulfinic acid sodium salt (10.0 g, 0.061 mol), 25% HCl was added dropwise with stirring until the solid dissolved. The reaction mixture was extracted (100 mL each, 3 times) with EtOAc, dried over $Na_2SO_4$ and concentrated to give benzenesulfonic acid (7.8 g, 90%). To a 100 mL round bottom with a magnetic stir bar, benzenesulfonic acid (4.61 g, 0.0324 mol), $CaCl_2$ (3.6 g, 0.0324 mol) and dry dichloromethane (30 mL) were added. The reaction mixture was cooled to 0° C. and (2S) (5RS)-2-(4-fluorophenoxymethyl)-5-hydroxy-tetrahydrofuran (4.6 g, 0.0216 mol) in dry $CH_2Cl_2$ (20 mL) was added. The reaction mixture was stirred for 3 h and monitored by TLC (EtOAc-light petroleum ether 1:4, Rf=0.25). The reaction mixture was filtered through celite and washed with $CH_2Cl_2$ (3 times). The combined organic layer was washed with saturated aqueous $Na_2CO_3$, water brine and dried over $Na_2SO_4$. Solvent was removed under reduced pressure to afford the crude (2S) (5RS)-5-benzenesulfonyl-2-(4-fluorophenoxymethyl)tetrahydrofuran 14 which was crystallized from chloroform-hexane to give pure white solid, yield 6.8 g (93%), m.p. 102° C.–104° C. $^1$H NMR (200 Mz $CDCl_3$): δ1.90–3.0 (m, 4H), 3.85–5.0 (m, 4H), 6.70–7.05 (mn, 4H), 7.45–7.72(m, 3H), 7.77–8.0 (n,2H).

Part 2: (2S) (5RS)-2-(4-fluorophenoxymethyl)-5-(4-tetrahydropyranoyl-1-butyne)-tetrahydrofuran (Scheme V; 9)

To a 250 ml two-necked RB flask equipped with magnetic stir bar, nitrogen inlet and a septum, Grignard grade magnesium (2.0 g, 0.0833 mol) was taken and the flask flame dried along with magnesium. The flask was cooled to room temperature and dry THF (5 mL) was added followed by 1,2-dibromoethane (catalytic amount) to activate the magnesium. Isopropylbromide (8.78 g, 0.0714 mol) in THY (140 mL) as added dropwise over 15 min. The reaction mixture was stirred for 1 hour. The isopropyl magnesium bromide was cannulated in a 1000 mL flame dried two-necked round bottom flask with spin-bar, nitrogen inlet and septum. 4-Tetrahydropyranoyl-1-butyne (11.0 g, 0.0714 mol) in THF (140 mL) was added. The reaction mixture was stirred for 30 min. and cooled at 0° C. Freshly prepared $ZnBr_2$ solution (1M, 43 mL, 0.0428 mol) in THF was introduced. After 45 min. at room temperature (2S) (5RS)-5-benzenesulfonyl-2-(4-fluorophenoxy-methyl)tetrahydrofuran (12.0 g, 0.0357 mol) in THF (70 mL) was added at room temperature and stirred for 3 h. (TLC, EtOAc-light petroleum 1:4, Rf=0.7). Saturated aqueous $NH_4Cl$ solution was added at 0° C. to quench the reaction. THF was removed on rotavapor and the reaction mixture was partitioned between water and EtOAc. The EtOAc layer was washed with water, brine, dried over $Na_2SO_4$ and concentrated to provide (2S) (5RS)-2-(4-fluorophenoxymethyl)-5-(4-tetrahydropyranoyl-1-butyne)-tetrahydrofuran 9, crude yield 18.9 g.

Part 3: (2S) (5RS)-2-(4-fluorophenoxy-methyl)-5-(4-hydroxybutyn-1-yl)tetrahydrofuran (Scheme V; 10)

That crude product 9 (18.9 g) was dissolved in methanol (60 mL) in 100 mL round bottom flask fitted with magnetic stirring arrangement. 1% HCl in methanol (25 mL) was introduced, and the reaction mixture was stirred at room temperature for 2 hours (TLC, EtOAc-light petroleum ether 1:1, Rf=0.4). The reaction mixture was neutralized by saturated aqueous $Na_2CO_3$ solution and then concentrated under reduced pressure. The residue was extracted with ethyl acetate, washed with water, brine, dried over $Na_2SO_4$ and concentrated on rotavapor. The residue was dried under vacuum on hot water bath to give (2S) (5RS)-2-(4-fluorophenoxy-methyl)-5-(4-hydroxybutyn-1-yl)tetrahydrofuran 10, yield 10.9 g. HPLC analysis: Column ODS; flowrate: 1.0 mL/min.; UV: 225 nm. Mobile phase 60% methanol in water. Trans:cis ratio (69:31). That crude product of 10 was crystallized (2 times) from ether-light petroleum ether by seeding to yield the pure product (3.3 g, 35%), m.p. 76° C. $[α]_D$ −34.26° (c 1.36, $CHCl_3$) HPLC purity above 95%.

EXAMPLE 5

Further Preparation of (4S)-4-fluorophenoxy-methyl)-γ-butyrolactone (Scheme VI; 6)

Part 1: Trimethylene D-mannitol (Scheme VI; 16)

D-mannitol (2.0 kg, 10.98 mol) (Scheme VII; 15) formaldehyde solution (35 % by weight, 4.4 lit, 51.2 mmol) and conc. HCl (4.0 lit.) were taken in a 10 lit. flask with mechanical stirring arrangement. The reaction mixture was kept at room temperature for 72 hours. The solid was filtered, washed with water and dried to provide 2.2 kg (91.9%) of trimethylene D-mannitol 16 m.p. 228°–230°, $[\alpha]_D$–108° (c 2.0, CHCl$_3$), TLC (silica gel), 1:2, ethyl acetate: hexane, Rf=0.4. $^1$H NMR (CDCl$_3$): δ3.4–3.75 (m, 6H), 4.18 (dd, J=4.0, 8.0 Hz), 4.59 (d, 2H, J=4.0 Hz), 4.76 (s, 2H), 5.05 (d, 2H, J=4.0 Hz).

Part 2: 1,3,4,6-Tetra-O-acetyl-2,5-O-methylene-D-mannitol (Scheme VI; 17)

Ice cold acetylating mixture (10.1 lit.) prepared from 7.0 liters of acetic anhydride, 3.0 liters of acetic acid and 0.1 liters of concentrated H$_2$SO$_4$ was taken in 20 lit. round bottom flask with mechanical stirring arrangement. Trimethylene D-mannitol 16 (2.2 kg, 10.1 mol) was slowly added in portions (45 min.–1 hour). After 3 h the reaction mixture was poured over ice-water with vigorous stirring (50–60 lit.). The solid was filtered, washed with water and dried to provide 2.8 kg (78%) of 17, m.p. 126°–128°, $[\alpha]_D$+57.8° (c 3.6, CHCl$_3$); TLC (silica gel), 2:1, ethyl acetate: hexane, Rf=0.5.

Part 3: 2,5-O-methylene-D-mannitol (Scheme VI; 18)

1,3,4,6-Tetra-O-acetyl-2,5-O-methylene-D-mannitol 17 (2.8 kg, 7.73 mol) was added to chloroform (14 lit.) in 25 lit. round bottom flask with mechanical stirring. The reaction mixture was cooled to 0° C., and 0.5% NaOMe solution (6.5 lit.) was added slowly. The reaction mixture was stirred for 3 hours. The solid was filtered and dried to provide 1.0 kg (67%) of 2,5-O-methylene-D-mannitol 18, m.p. 172°–173° C., $[\alpha]_D$520° (c 1.18, CHCl$_3$), TLC (silica gel), 1:4, methanol: chloroform, Rf=0.8. $^1$H NMR (D$_2$O): δ3.42 (m, 2H), 3.72 (m, 4H), 3.97 (m, 2H), 4.91 (s, 2H).

Part 4: 1,6-Di-O-tosyl-2,5-O-methylene-D-mannitol (Scheme VI; 19)

2,5-O-methylene-D-mannitol 18 (200 g, 1.03 mol) was dissolved in pyridine (1.2 lit.) in 3 liter two neck R B flask fitted with an addition funnel and mechanical stirring arrangement. The reaction mixture was cooled to 0° C., tosyl chloride (430.9 g, 2.26 mol) dissolved in pyridine (0.8 lit.) was added slowly, and the reaction mixture was stirred at room temperature for 12 h. Pyridine then was removed on rotavapour under vacuo. The thick slurry was poured over ice-water (10 lit.) with mechanical stirring. After 2 hours the solid was filtered, washed with water, dried (yield, 400 g crude) and crystallized from methanol to provide 260 g of product 1, m.p. 142° C., $[\alpha]_D$–23.39° (c 1.7, MeCOMe), TLC (silica gel), 4:1, ethyl acetate: hexane, Rf=0.4. $^1$H NMR (CD$_3$COCD$_3$): δ2.45 (s, 6H), 2.85 (s, 2H), 3.27 (m, 2H), 3.65 (m, 2H), 4.12 (dd, 2H, J=6.2, 10.0 Hz), 4.45 (m, 2H), 4.46 (s, 2H), 7.38, 7.63 (Abq, 8H, 3=8.0 Hz).

Part 5: 3,4-O-Ethoxymetyhlene-2,5-O-methylene-1-6-di-O-tosyl-D-mannitol (Scheme VI, 20)

2,5-O-methylene-1,6-di-O-tosyl-D-mannitol 19, (185 g, 0.368 mol) triethylorthoformate (613 mL) and PTSA (100 mg) were stirred in a 1 lit. round bottom flask fitted with mechanical stirring arrangement at room temperature. After 3 hours of stirring potassium carbonate was added to neutralize PTSA. Solid was filtered and filtrate concentrated under reduced pressure and dried under vacuo to provide 206 g (100%) of product 20, m.p. 87–88° C., $[\alpha]_D$+46.02° (c 0.93, CHCl$_3$), TLC (silica gel) 7:3 hexane: EtOAc, Rf=0.4. $^1$H NMR (CDCl$_3$): δ1.21 (t, 3H, J=7.6 Hz), 2.45 (s, 6H), 3.55 (q, 2H, J=7.6 Hz), 3.7–3.85 (m, 2H), 3.97 (t, 1H, J=8.5 Hz), 4.08–4.31 (m, 5H), 4.74 (s, 2H), 5.76 (s, 1H), 7.34, 7.77 (ABq, 8H, J=8.5 Hz).

Part 6: 3,4-O-ethoxymethylene-1,6-di-O-p-fluorophenyl-2,5-O-methylene-D-mannitol (Scheme VI: 21)

4-Fluorophenol 2 (124 g, 1.107 mol) was dissolved in CH$_3$CN (250 mL) and then KOH solution (62 g, in 45 mL, H$_2$0, 1.107 mol) was added. The reaction mixture was stirred for 15 minutes. 3,4-O-Ethoxymethylene-2,5-O-methylene-1-6-di-O-tosyl-D-mannitol 20 (206 g, 0.369 mol) (used as prepared in Part 5 above without further purification) in CH$_3$CN (400 mL) was separately taken in 1 liter two neck round bottom flask fitted with reflux condenser, guard tube and mechanical stirring arrangement. To this solution the potassium salt of 4-fluorophenol was added at room temperature. The reaction mixture was heated under reflux for 6 hours and monitored by TLC (silica gel, 3:7, ethyl acetate: hexane, Rf=0.7). The reaction mixture was cooled in ice-water and solid was filtered washed with ethyl acetate (100 mL), and the combined filtrate was concentrated under reduced pressure. The resulting residue was dissolved in ethyl acetate (800 mL) and the organic layer was washed with 2M NaOH (4×100 mL), water and brine dried over Na$_2$SO$_4$. Concentration under reduced pressure afforded 3,4-O-ethoxymethylene-1,6-di-O-p-fluorophenyl-2,5-O-methylene-D-mannitol 21 (147 g, 90.9%). $^1$H NMR (CDCl$_3$): δ1.3 (t, 3H, J=6.25 Hz), 3.70 (q, 2H, J=6.25 Hz), 4.0–4.45 (m, 7H), 4.56 (t, 1H, J=9.6 Hz), 5.19 (s, 2H), 5.97 (s, 1H), 6.89–7.10 (m, 8H).

Part 7: 1,6-Di-O-p-fluorophenyl-2,5-O-methylene-D-mannitol (Scheme VI: 22)

3,4-O-Ethoxymethylene-1,6-di-O-p-fluorophenyl-2,5-O-methylene-D-mannitol 21 (145 g 0.331 mol), tetrahydrofuran (350 mL) and 0.1% aqueous HCl (40 mL) were mixed in a 1 lit two neck round bottom flask fitted with mechanical stirring arrangement at 0° C. The reaction mixture was allowed to attain room temperature and further stirred for 6 hours and monitored by TLC (silica gel, 1:1, ethyl acetate: hexane, Rf=0.3). The reaction mixture was basified to pH 8 by saturated NaHCO$_3$ solution, and the solid was filtered and the filtrate concentrated to dryness to provide 125 kg (99%) of product 22, m.p. 126–127° C., $[\alpha]_D$–34.49° (c 1.148, MeCOMe). $^1$H NMR (CDCl$_3$): δ2.7 (s, 2H), 3.72 (m, 2H), 3.90 (m, 2H), 4.12 (m, 4H), 4.87 (s, 2H), 6.77–7.0 (m, 8H).

Part 8: 4,4'-methylenedioxy-bis[(R)ethyl, (E)-2-ene-5-p-fluorophenoxy-pentanoate] (Scheme VI: 23)

In a 250 ml two neck round bottom flask equipped with magnetic stirring arrangement and fitted with a guard tube was taken a solution of 1,6-di-O-p-fluorophenyl-2,5-O-methylene-D-mannitol 22 (10.0 g, 0.026 mol) in CH$_2$Cl$_2$ (100 ml). The solution was cooled to 0° C. and Pb(OAc)$_4$ (12.8 g, 0.0288 mol) was added in portions. After 3 hours, ethylene glycol (1 ml) was added to quench excess Pb(OAc)$_4$. The reaction mixture was filtered over celite, and the filtrate was washed successively with water and brine. The organic layer was dried over Na$_2$SO$_4$ and concentrated under reduced pressure to afford the di-aldehyde as a thick syrup. That crude dialdehyde was taken in CH$_2$Cl$_2$ (100 ml) in 250 ml two necked round bottom flask with magnetic stirring arrangement and fitted with a nitrogen inlet. Carboethoxymethylenetriphenyl phosphorane (27.3 g, 0.0785 mol) was added in portions. The reaction mixture then was stirred for 3 hours, concentrated and purified on silica gel chromatography with 85:15 hexane:ethyl acetate as the eluent. The isolated fractions on concentration under reduced pressure yielded 4,4'-methylenedioxy-bis[ethyl, (E)-2-ene-5-p-fluorophenoxypentanoate] 23 (10.0 g, 74%) as an oil. $^1$H NMR (CDCl$_3$): δ1.24–1.40 (m, 6H), 3.86–4.30 (m, 8H), 4.70 (m, 1H), 4.84 (s, 2H), 5.70 (brs, 1H), 5.9–6.32 (m, 4H), 6.76–7.02 (m, 8H).

Part 9: 4S-(4-Fluorophenoxymethyl)-γ-butyrolactone (Scheme VI: 6)

A solution of 4,4'-methylenedioxy-bis[(R)ethyl, (E)-2-ene-5-p-fluorophenoxypentanoate] 23 (10.0 g, 0.0192 mol) in methanol (10 ml) was taken in a 200 ml parr hydrogenation flask. Pd/C (500 mg) was added to that solution and the mixture shaken in a parr apparatus at 40–50 psi for 6 hour and monitored by TLC. The reaction mixture was filtered over celite and the filtrate concentrated to afford 4,4'-methylenedioxy-bis[(R) ethyl, 5-p-fluorophenoxypentanoate] as an oil (10.0 g, 100%).

A 250 ml round bottom flask equipped with magnetic stirring arrangement and fitted with a reflux condenser was then charged with 4,4'-methylenedioxy-bis [®ethyl, 5-p-fluorophenoxypentanoate] (10.0 g, 0.019 mol) in ethanol (60 ml). To that solution 10% aqueous solution H$_2$SO$_4$ (15 ml) was added. The mixture was heated under reflux for 10–12 hours and monitored by TLC, silica gel, 1:1; ethyl acetate: hexane, Rf=0.25. The reaction was cooled to 0° C. and neutralized with saturated sodium bicarbonate solution. The reaction mixture was concentrated on a rotavapour to dryness and redissolved in ethyl acetate (100 ml). The organic layer was washed with water and brine dried over Na$_2$SO$_4$ and concentrated. The residue was purified by column chromatography to afford off white crystalline solid of 4S-(4-fluorophenoxymethyl)-γ-butyrolactone 6 (7.0 g, 87%), .m.p 60–61° C., [α]$_D$+25° (c 2.18, CHCl$_3$). $^1$H NMR (CDCl$_3$): δ2.13–2.80 (m, 4H), 4.02 (dd, 1H, J=4.5, 9.0 Hz), 4.11 (dd, 1H, J=4.5, 9.0 Hz), 4.80 (m, 1H), 6.75–7.02 (m, 4H).

EXAMPLE 6

Further Alternate Preparation of (2S) (5RS)-2-(4-Fluorophenoxymethyl)-5-(4-hydroxybutyn-1-yl)-tetrahydrofuran (Scheme VII; 10)

Part 1: (±) 1,2-Epoxy-(4-fluoro)phenoxy propane (Scheme VII; 25)

p-Fluorophenol 2 (5 g, 44.6 mmol) and epichlorohydrin 24 (16.5 g, 178.4 mmol 13) were admixed in anhydrous acetone (100 ml). Anhydrous K$_2$CO$_3$ (24.0 g, 178.4 mmol) was added in 10 minutes and the reaction mixture was heated at reflux for 18 hours until the complete consumption of p-fluorophenol as monitored by TLC (4:1 hexane:ether). The reaction mixture then was filtered off, the filtrate was concentrated under vacuo to afford a light yellow oil, excess epichlorohydrin was distilled off, the residue was subjected to column chromatography on silica gel (2:8, ethyl acetate-hexane) to afford (±)-1,2-epoxy-(4-fluoro)phenoxy propane 25 in quantitative yield (8.5 g).

Part 2: (2R)-3-(4-fluoro)phenoxy-propane-1,2-diol (Scheme VII; 26)

(2R)-3-(4-fluoro)phenoxy-propane-1,2-diol 26 was prepared using Jacobsen's catalyst as generally described in E. Jacobsen, *Science*, 277:936–938 (1997). More specifically (±)-1,2-epoxy-3-(4-fluoro)phenoxy propane 25 (10 g, 59.5 mmol) and (R,R)-Jacobsen's catalyst (215 mg, 0.29 mmol) were taken in a 50 ml round bottom flask and cooled to 0° C. Water (0.6 ml, 32.7 mmol) was then added dropwise for 1 hour and stirred for 5 hours at room temperature, monitored by TLC (1:1 ethyl acetate:hexane). Ethyl acetate (50 ml) was added, followed by anhydrous Na$_2$SO$_4$ (200 mg), stirred for 10 minutes filtered, concentrated to afford dark colored residue of a mixture of 26 and 27, which on column chromatography gave isolated epoxide 27 (4.36 g, 43%, 1:9 ethyl acetate-hexane) and (2R)-3-(4-fluoro)phenoxy-propane-1,2-diol 26 (5.06 g, 46%, 1:1 ethyl acetate-hexane).

Part 3: (2S)-3-(4-fluoro)phenoxy-1-tosyloxy-propan-2-ol (Scheme VII; 28)

A mixture of(2R)-3-(4-fluoro)phenoxy-propan-1,2-diol 26 (5.0 g, 26.8 mmol) and pyridine (4.5 ml) in CH$_2$Cl$_2$ (60 ml) were cooled to 0° C., and then p-toluenesulphonyl chloride (5.0 g, 26.8 mmol) was added portionwise to the cooled mixture. The mixture was stirred at room temperature overnight (TLC 2:3, ethyl acetate-hexane). The solvent was then removed by codistillation with toluene, and the resulting residue purified by silica gel column chromatography (2:3, ethyl acetate-hexane) to afford the product 28 (7.7 g, 85%).

Part 4: (2R)-1,2-epoxy-3-(4fluoro)phenoxypropane (Scheme VII; 4)

(2R)-(4-Fluoro)phenoxy-1-tosyloxy-propan-2-ol 28 (5.0 g, 14.7 mmol) in a solvent mixture of THF and DMF (100 ml, 4:1) was cooled to 0° C. and NaH (0.75 g, 19.2 mmol) was added portionwise, followed by stirring of the reaction mixture for 1 hour at room temperature with monitoring of the reaction by TLC (20% ethyl acetate in hexane). The THF was removed and the residue was taken in ethyl ether (50 ml). That ether solution was washed successively with water (3×50 ml), brine (1×50 ml) dried (Na$_2$SO$_4$) and concentrated to afford (2R)-1,2-epoxy-3-(4-fluoro)phenoxypropane 4 as a colorless oil (2.53 g, 95%).

Part 5: (2R)-1-(4-fluoro)phenoxyhex-5-en-2-ol (Scheme VII; 29)

Magnesium (0.89 g, 36.6 mmol) and iodine (catalytic amount) were taken in a 50 ml 2-neck round bottom flask provided with a reflux condenser and a septum, under N$_2$ atmosphere. A solution of allyl bromide (3.0 g, 24.4 mmol) in 10 ml of ethyl ether was slowly added and stirred for 30 minutes at room temperature. Cuprous cyanide (22 mg) then was added, and the color of the reaction mixture became dark brown. The reaction mixture was cooled to −22° C. (CCl$_4$/dry ice bath), and (2R)-1,2-epoxy-3-(4-fluoro) phenoxypropane 4 (2.05 g, 12.2 mmol) in 25 ml of ethyl ether was added. The reaction was completed within 30 minutes, as determined by TLC (benzene). Saturated aqueous ammonium chloride (4 ml) then was added and the mixture stirred for 30 minutes. Inorganic material was filtered and washed with ethyl ether (25 ml). The ether layer was dried (sodium sulphate) concentrated to give a colorless oil of (2R)-1-(4-fluoro)phenoxyhex-5-en-2-ol 29 (2.3 g, 90%).

Part 6: (2R)-2-benzenesulfonyloxy-1-(4-fluoro)-phenoxy-5-hexane (Scheme VII; 30)

(2R)-(4-Fluoro)phenoxyhex-5-en-2-ol, 29 (7.4 g, 35.2 mmol), triethylamine (10 ml) and 4-N,N'- dimethylaminopyridine (DMAP, 0.43 g, catalytic) were dissolved in 50 ml of dry $CH_2Cl_2$ and cooled in ice bath while stirring. Benzenesulfonyl chloride (5 ml, 38.7 mmol) in $CH_2Cl_2$ (10 ml) was then added dropwise to the mixture. The reaction mixture was stirred at room temperature for 6 hours and monitored by TLC (benzene)]. Solvent then was removed and the residue was poured onto a short silica gel column and eluted with 1:4 ethyl acetate-hexane to afford (2R)-2-benzenesulfonyloxy-1-(4-fluoro)-phenoxy-5-hexane 30 as a colorless oil (11.3 g, 92%).

Part 7: (6R,2E)-ethyl-6-benzenesulfonyloxy-7-(4-fluoro)-phenoxy-hept-2-en-1-oate (Scheme VII; 31)

(2R)-2-Benzenesulfonyloxy-1-(4-fluoro)-phenoxy-5-hexane 30 (11.3 g, 32.5 mmol 19) in 30 ml of dry $CH_2Cl_2$ was cooled to −78° C. $O_3$ then was bubbled through the mixture until the blue color persisted (30 minutes). A stream of $N_2$ then was purged for 5 minutes through the mixture to remove excess of ozone. Dimethylsulfide (13.9 ml, 325 mmol) was added, and the mixture stirred for 2 hours. The reaction mixture was washed with water (2×25 ml), brine (1×30 ml) and concentrated to afford the crude product (10.8 g, 95%). (2R)-Benzenesulfonyloxy-1-(4-fluoro)-phenoxy-5-pentanal (10.5 g, 30 mmol) was added and heated at reflux for 5 hours. Ethoxycarbonylmethylene triphenylphosphorane (11.5 g, 33 mmol) was added and heated at reflux for 5 hours. Completion of the reaction was checked by TLC (1:10, EtOAc-benzene) and the solvent was removed, the residue was purified by column chromatography on silica gel (1:3, ethyl acetate-hexane) to afford (6R,2E)-ethyl-6-benzenesulfonyloxy-7-(4-fluoro)-phenoxy-hept-2-en-1-oate 31 (8.8 g, 70%) as a colorless oil.

Part 8: (6R,2E)-ethyl-6-benzenesulfonyloxy-7-(4-fluoro)-phenoxy-hept-2en-1-ol (Scheme VII; 32)

(6R,2E)-Ethyl-6-benzenesulfonyloxy-7-(4-fluoro)-phenoxy-hept-2-en-1-oate (3 g, 7.1 mmol) 31 was dissolved in 30 ml of $CH_2Cl_2$ under $N_2$ atmosphere and cooled to −78° C. DIBAL-H (14.2 ml, 14.2 mmol, 1M solution in toluene) was added dropwise over 5 minutes and the solution was stirred at −78° C. for 45 minutes. At reaction completion as monitored by TLC (2:5, ethyl acetate-hexane), saturated aqueous ammonium chloride solution (3 ml) was added and the mixture stirred for another 30 minutes. The reaction mixture then was filtered through a celite pad the filtrate was dried over anhydrous $Na_2SO_4$ and concentrated, the residue was filtered through a short silica gel pad and concentrated to obtain (6R,2E)-ethyl-6-benzenesulfonyloxy-7-(4-fluoro)-phenoxy-hept-2-en-1-ol 32 as a solid (2.2 g, 82% yield).

Part 9: (2S,3S,6R)-6-benzenesulfonyloxy-2,3-epoxy-7-(4-fluoro)-phenoxy-7-heptan-1-ol (Scheme VII; 33)

Powdered molecular sieves 4 Å (3 g) were activated under $N_2$ atmosphere in a 25 ml 2 necked round bottom flask. $CH_2Cl_2$ (15 ml) was added followed by titanium tetraisopropoxide (1.62 ml, 5.47 mmol), (+)-diisopropyltartrate (1.07 ml, 6.56 mmol) and the mixture was cooled to −20° C. with stirring. After 5 minutes cumene-hydroperoxide (2.1 ml, 10.94 mmol, 80% solution in cumene) was added dropwise. The mixture was stirred for 15 minutes at −20° C. (6R,2E)-benzenesulfonyloxy-7-(4-fluoro)-phenoxy-hept-2-en-1-ol 32 (2.0 g, 5.47 mmol) in 10 ml of $CH_2Cl_2$ was then added and the reaction mixture was stirred for 2.5 hours at −20° C. The reaction mixture was checked for the completion by TLC (1:1, ethyl acetate-hexane), 1 ml of 10% aqueous tartaric acid solution was added at −20° C. and the reaction mixture was warmed to room temperature in 30 minutes. The reaction mixture was filtered through a celite pad dried over $Na_2SO_4$, concentrated and the residue was subjected to column chromatography on silica gel (1:1, ethyl acetate-hexane) to afford (2S,3S,6R)-6-benzenesulfonyloxy-2,3-epoxy-7-(4fluoro)-phenoxy-7-heptan-1-ol 33 (2.4 g, 98% yield) as a solid.

Part 10: (2S,3S,6R)-6-benzenesulfonyloxy-1-chloro-2,3-epoxy-7-(4-fluoro)-phenoxy-heptane (Scheme VII; 34)

(2S,3S,6R)-6-Benzenesulfonyloxy-2,3-epoxy-7-(4-fluoro)-phenoxy-7-heptan-1-ol (2.25 g, 5.7 mmol) 33 and triphenylphosphine (1.5 g, 5.7 mmol) were dissolved in solvent mixture of $CHCl_3$ and $CCl_4$ (40 ml, 1:1) and $NaHCO_3$ (0.3 g) was added. The reaction mixture was refluxed for 3 hours and monitored by TLC (2:5, ethyl acetate-hexane). Solvent was removed, the residue was purified by column chromatography on silica gel (1:4, ethyl acetate-hexane) to afford (2S,3S,6R)-6-benzenesulfonyloxy-1-chloro-2,3-epoxy-7-(4-fluoro)-phenoxy-heptane 34 (1.5 g, 64% yield) as a solid.

Part 11: (2S,5S)-5-ethynyl-2-(4-fluoro)-phenoxymethyl-tetrahydrofuran (Scheme VII; 35)

n-BuLi (7.2 ml, 7.2 mmol) was added to a solution of freshly distilled diisopropylamine (1.12 ml, 8.6 mmol) in 6 ml of dry THF at −40° C. and stirred for 15 minutes. A solution of (2S,3S,6R)-6-benzenesulfonyloxy-1-chloro-2,3-epoxy-7-(4-fluoro)-phenoxy-heptane 34 (1.0 g, 2.42 mmol) was added in 8 ml of dry THF. The reaction mixture was stirred at −40° C. for 1 hour and then at room temperature for 1 hour. When TLC showed complete consumption of starting material the reaction was quenched at 40° C. with aqueous ammonium chloride (1 ml), THF was removed under vacuo, the residue was taken in ethyl acetate, filtered, dried over $Na_2SO_4$ and concentrated. Crude product was subjected to column chromatography on silica gel (1:9, ethyl acetate-hexane) to afford (2S,5S)-5-ethynyl-2-(4-fluoro)-phenoxymethyl-tetrahydrofuran 35 (0.32 g, 60% yield).

Part 12: Preparation of (2S,5S)-5-(2'-hydroxyethyl)-ethynyl-2-(4-fluoro)-phenoxymethyltetrahydrofuran (Scheme VII; 10)

To a solution of (2S,5S)-5-ethynyl-2-(4-fluoro)-phenoxymethyl-tetrahydrofuran 35 (0.8 g, 3.6 mmol) in 15 ml of dry THF at -78° C., n-BuLi (5 ml, 1M solution in hexane), stirred for 15 minutes. Freshly distilled $BF_3Et_2O$ (1.4 ml, 11 mmol) was added followed by ethyleneoxide (excess, THF solution). The reaction mixture was allowed to stir at −78° C. until completion (30 minutes). Saturated aqueous ammonium chloride solution (1 ml) was added at −78° C. stirred for 5 minutes, warmed to room temperature, THF was removed, residue was extracted with ether (2×20 ml), combined organic layer was dried over $Na_2SO_4$, concentrated to afford a residue. That residue was purified by column chromatography on silica gel (2:5, ethyl acetate-hexane) to afford (2S,5S)-5-(2'-hydroxyethyl)-ethynyl-2-(4-fluoro)-phenoxymethyltetrahydrofuran 10 (0.87 g, 90% yield) as a white solid. That product 10 was found to be identical (NMR, optical rotation, TLC) with samples prepared by Example 1 above.

EXAMPLE 7

Further Alternate Preparation of (2S) (5RS)-2-(4-Fluorophenoxymethyl)-5-(4-hydroxybutyn-1-yl)-tetrahydrofuran (Scheme VII; 10)

References in this Example 7 to compound numerals (generally underlined) designate the compounds depicted structurally in Scheme VIII above.

Part 1: 1,2:5,6-Di-O-isopropylidene-(D)-mannitol (Scheme VII; 2)

A solution of D-mannitol 1 (100 g, 0.549 mol) in a mixture of DMSO (160 mL, distilled and stored over molecular sieves) and dimethoxy propane (149 mL, 1.209 mol), at room temperature, was treated with p-toluene sulfonic acid (PTSA; 0.5 g) and stirred for 18 h. The reaction mixture was treated with Et$_3$N (3 mL), to quench PTSA, and water (500 mL) and extracted with hexanes (3×200 mL) to remove the tri acetonide (5–7 g). The reaction mixture was then extracted with EtOAc (4×500 mL) and washed with NaCl solution. Evaporation of the solvent gave pure 1,2:5,6-di-O-isopropylidene-(D)-mannitol 2 (95 g) in 66% yield as a solid, m.p. 118–120° C. (lit. m.p. 120–122° C. (ref Organic Synthesis 1995, 72, 6)).

Part 2: Ethyl (2E,4S)-4,5-isopropylidenedioxy-2-pentenoate (Scheme VIII; 4):

A solution of 1,2:5,6- di-O-isopropylidene-(D)-mannitol 2 (100 g, 0.38 mol) in CH$_2$Cl$_2$ (1000 mL) containing saturated NaHCO$_3$ solution (40 mL) was cooled to 0° C., treated with NaIO$_4$ (123 g, 0.57 mol) and allowed to stir at 0° C. to 20° C. After 2 to 3 h 3 (TLC analysis), solid Na$_2$SO$_4$.(35 g) was added and the reaction mixture was stirred further for 15 min. The reaction mixture was filtered and concentrated (below 25° C. bath temperature) to half the volume.

The above solution of (R)-glyceraldehyde 3 in CH$_2$Cl$_2$ (500 ML) was cooled to below 10° C. and treated with (carbethoxymethylene) triphenyl phosphorane (132 g, 0.38 mol) in portions. After stirring at room temperature for 3–4 h, the solvent was evaporated, the residue treated with hexane (500 mL) and the solution decanted through silica gel. The residue was further treated with 10% EtOAc in hexane (4×500 mL) and decanted through silica gel. Evaporation of solvent afforded ethyl (2E,4S)-4,5-isopropylidenedioxy-2-pentenoate 4 (105 g) in 73 % yield as a colorless liquid. $^1$HNMR (CDCl$_3$, 200 MHz): δ1.2 (t, 3H, J 7.1 Hz, CH$_3$), 1.3, 1.35 (2s, 6H, CH$_3$), 3.48 (dd, 1H, J 6.1 Hz, H-5), 4.05 (q, 2H, J 7.1 Hz, OCH$_2$), 4.25 (dd, 1H, J 8.0 Hz, H-5a), 5.3–5.40 (m, 1H, H-4), 5.72 (dd, 1H, J 2.3, 11.0 Hz, H-2), 6.72 (dd, 1H, J6.1, 12.2 Hz, H-3).

Part 3: Ethyl (4S)-4,5-isopropylidenedioxy-1-pentanoate (Scheme VIII; 5)

A solution of ethyl (2E,4S)-4,5-isopropylidenedioxy-2-pentenoate 4 (90 g, 0.45 mol) in EtOAc (100 mL) was treated with PtO$_2$ (0.225 g) and subjected to hydrogenation till there was no further consumption of hydrogen (3–4 h). At the end of reaction, the reaction mixture was filtered and the solvent evaporated to afford ethyl (4S)-4,5-isopropylidenedioxy-1-pentanoate 5 (90 g) in 99% yield as a colorless liquid. [α]$_D$+4.99 (c 2.2, CHCl$_3$); $^1$HNMR (CDCl$_3$, 200 MHz): δ1.28 (t, 3H, J 7.1 Hz, CH$_3$), 1.30, 1.45 (2s, 6H), 1.8–1.95 (m, 2H, H-3), 2.38–2.5 (m, 2H, H-2), 3.52 (dd, 1H, J 7.1 Hz, H-5), 4.0–4.2 (m, 4H, H-4,5a,—OCH$_2$)

Part 4: (2S)1,2-Isopropylidenedioxy-5-pentanol (Scheme VIII; 6)

A suspension of LAH (16.9 g, 0.44 mol) in THF (300 mL) was cooled to 0° C. and treated dropwise with a solution of ethyl (4S)-4,5-isopropylidenedioxy-1-pentanoate 5 (90 g, 0.44 mol) in THF (200 mL). The reaction mixture was then allowed to stir at room temperature for 10–12 h and treated with a saturated solution of Na$_2$SO$_4$ (38 mL) at 0° C. for an additional 30 min. period, it was filtered through celite and washed with EtOAc (3×200 mL). The combined organic layers were washed with saturated NaCl solution and evaporated in vacuo to provide (2S)-1,2-isopropylidenedioxy-5-pentanol 6 (65.5 g) in 92% yield as a colorless liquid. [α]$_D$+14.18 (c 2.2 CHCl$_3$). $^1$HNMR (CDCl$_3$, 200 MHz): δ1.3, 1.4 (2s, 6H), 1.6–1.8 (m, 5H, H-3,4,OH), 3.5 (t,1H, J 8.3 Hz ,H-1), 3.6–3.7 (m, 2H, H-5), 4.0–4.18 (m, 2H, H-1a,2); $^{13}$CNMR (CDCl$_3$, 50 MHz): δ25.5, 26.7, 28.9, 30.0, 62.2, 69.3, 76.3, 108.8; MS: 145 (M$^+$-15); HRMS: Calculated for C$_7$H$_{13}$O$_3$ (M$_+$-15): 145.086469: Observed: 145.086081.

Part 5: (4S)-4,5-Isopropylidenedioxy-1-pentanal (Scheme VIII; 7):

A stirred solution of (2S)-1,2-isopropylidenedioxy-5-pentanol 6 (20 g, 0.125 mol) in DMSO (60 mL) was cooled to 0° C., treated with IBX (38.5 g, 0.137 mol) in portions while maintaining the temperature below 0° C. and allowed to stir at room temperature for 4 h. The reaction mixture was treated with saturated NaHCO$_3$ solution (25 mL), filtered through celite and washed with EtOAc (3×150 mL). The layers were separated and the organic layer was washed with water, brine and dried (Na$_2$SO$_4$). Evaporation of solvent furnished (4S)-4,5-isopropylidenedioxy-1-pentanal 7 (16.1 g) in 81% yield as a dark yellow liquid. [α]$_D$+3.8 (c 1.0, CHCl$_3$); $^1$HNMR (CDCl$_3$, 200 MHz): δ1.3, 1.35 (2s, 6H, CH$_3$), 1.6–2.1 (m, 4H, H-2,3), 2.6 (t, 2H, J$_{2,3}$6.2 Hz, H-2), 3.5 (t, 2H, J$_{4,5}$6.2 Hz, 6.2 Hz, H-5), 3.98–4.2 (m, 2H, H-4,5a), 9.8 (s, 1H, CHO).

Part 6: Ethyl (2E,6S)-6,7-isopropylidenedioxy hept-2-enoate (Scheme VIII; 8):

A solution of (4S)-4,5-isopropylidenedioxy-1-pentanal 7 (24 g, 0.15 mol) in benzene (250 mL) was treated with (carbethoxymethylene) triphenyl phosphorane (57.8 g, 0.166 mmol) and heated at reflux for 6 h. Solvent was evaporated, the residue was treated with hexane (500 mL) and decanted through silica gel. Further, the residue was treated with 10% EtOAc in hexane (3×500 mL) and the solution filtered through silica gel. Evaporation of the combined solvents afforded ethyl (2E,6S)-6,7-isopropylidenedioxy hept-2-enoate 8 (26 g) in 76% yield as a pale yellow liquid. [α]$_D$+6.9 (c 1.0, CHCl$_3$); $^1$HNMR (CDCl$_3$, 200 MHz): δ1.28 (t, 3H, J 6.75 Hz, CH$_3$), 1.32, 1.38 (2s, 6H), 1.6–1.8 (m, 2H, H-5), 2.2–2.45 (m, 2H, H-4), 3.5 (t, 1H, J 6.75 Hz, H-7), 3.95–4.25 (m, 4H, H-6,7a,OCH$_2$), 5.8 (d, 1H, J 15.75 Hz, H-2), 6.82–7.02 (dt, 1H J 7.8, 15.75 Hz, H-3); MS: 213 (M$^+$-15).

Part 7: (2E,6S)-6,7-Isopropylidenedioxy hept-2-ene-1-ol (Scheme VIII; 9)

A stirred solution of ethyl (2E,6S)-6,7-isopropylidenedioxy hept-2-enoate 8 (15 g, 65.7 mmol) in dry CH$_2$Cl$_2$ (80 mL) was cooled to -20° C. (CCl$_4$+dry ice bath) and treated drop wise with a solution of DIBAL-H (66 mL, 134 mmol; 2N solution in hexane). After stirring for 2 h, the reaction mixture was warmed to 0° C., treated with a saturated solution of Na—K tartarate (20 mL) drop wise and stirred for an additional 45 min. The organic layer was separated and the aqueous layer extracted with CH$_2$Cl$_2$ (100 mL). The combined organic layers were washed with brine, dried (Na7SO$_4$) and evaporated in vacuo to provide (2E, 6S)-6,7-isopropylidenedioxy hept-2-ene-1-ol 9 (10.8 g) in 88% yield a colorless liquid. [α]$_D$+12.83 (c 2.17, CHCl$_3$); $^1$HNMR (CDCl$_3$, 200 MHz): δ1.35, 1.40 (2s, 6H), 1.4–1.8

(m, 2H, H-5), 2.05–2.3 ( m, 2H, H-4), 3.5 (t, 1H, J 7.95 Hz, H-7), 3.95–4.2 (m, 4H, H-1,6,7a), 5.65–5.72 (m, 2H, H-2,3); $^{13}$CNMR (CDCl$_3$, 50 MHz): δ25.60, 26.81, 28.26, 32.96, 63.20, 69.19, 75.38, 108.63, 129.68, 131.47; MS: 175 (M$^+$–15); HRMS: Calculated for C$_9$H$_{15}$O$_3$ (M$^+$–15): 171.102120; Observed: 171.102318.

Part 8: (2S,3S,6S)-2,3-Epoxy-6,7-isopropylidenedioxy heptan-1-ol (Scheme VIII; 10)

Method A (Stoichiometric)—To a stirred and cooled (–20° C.) suspension of molecular sieves (4A, 4 g), in CH$_2$Cl$_2$ (15 mL) under N$_2$ atmosphere, (+) Diisopropyl L-tartarate (18.1 g, 77.4 mmol) in CH$_2$Cl$_2$ (20 mL), Titanium(IV) isopropoxide (19.1 mL, 64.54 mmol) and cumene hydroperoxide (19.6 mL, 103 mmol; 80% solution in cumene) were added sequentially. After 20 min. the resulting mixture was treated with a solution of (2E,6S)-6,7-isopropylidenedioxy hept-2-ene-1-ol 9 (12 g, 64.5 mmol) in CH$_2$Cl$_2$ (30 mL) drop wise and stirred further for 3 h at the same temperature. The reaction mixture was quenched with 10% NaOH solution saturated with NaCl (20 mL) and filtered through celite. Evaporation of solvent and purification of residue by column chromatography (Si-gel, 1:1.5 EtOAc-hexane) furnished (2S,3S,6S)-2,3-epoxy-6,7-isopropylidenedioxy heptan-1-ol 10 (7.5 g) in 57% yield as a colorless liquid. [α]$_D$–15.06(c 3.0, CHCl$_3$); $^1$HNMR (CDCl$_3$, 200 MHz): δ1.35, 1.4 (2s, 6H, CH$_3$), 1.45–1.85 (m, 5H, H-4,5,—OH), 2.85–3.05 (m, 2H, H-2,3), 3.5 (t, 1H, J 6.5 Hz, H-7), 3.65 (dd, 1H, J 4.08, 12.2 Hz, H-1), 3.9 (dd, 1H, J 3.06, 12.2 Hz, H-1a), 3.98–4.2 (m,2H, H-6,7a); $^{13}$CNMR (CDCl$_3$, 50 MHz): δ25.33, 26.31, 27.33, 29.87, 55.34, 58.41, 61.83, 69.12, 75.13, 100.84.

Method B (Catalytic—10 mol %)—A stirred mixture of (+) diisopropyl L-tartarate (1.5 g, 6.45 mmol) and molecular sieves (4A, 4 g) in CH$_2$Cl$_2$ (30 mL) was cooled to –20° C. under N$_2$ atmosphere and treated with titanium(IV) isopropoxide (1.59 mL, 5.37 mmol). After 20 min. cumene hydroperoxide (16.3 mL, 86.0 mmol) was added followed by addition of a solution of (2E,6S)-6,7-isopropylidenedioxy hept-2-ene-1-ol 9 (10.0 g, 53.7 mmol) in CH$_2$Cl$_2$ (25 mL) drop wise. The reaction was conducted out for 12 h at –20° C. and worked up as already described above to give (2S,3S,6S)-2,3-epoxy-6,7-isopropylidenedioxy heptan-1-ol 10 (6.2 g) in 58% yield as a liquid, whose spectral data was comparable with that of the above compound.

Part 8: (2S,3S,6S)-1-Chloro-2,3-epoxy-6,7-isopropylidenedioxy heptane (Scheme VIII; 11):

A stirred mixture of (2S,3S,6S)-2,3-epoxy-6,7-isopropylidenedioxy heptan-1-ol 10 (6.0 g, 29.7 mmol), Ph$_3$P (9.69 g, 35.6mmol) and NaHCO$_3$ (0.8 g) in CCl$_4$ (30 mL) was heated at reflux for 3 h. The solvent was evaporated and the residue obtained on chromatographic purification (Si-gel, 15% EtOAc-hexane) gave (2S,3S,6S)-1-chloro-2,3-epoxy-6,7-isopropylidenedioxy heptane 11 (6.2 g) in 95% yield as a colorless liquid. [α]$_D$–33.19(c 3.0, CHCl$_3$); $^1$HNMR (CDCl$_3$, 200 MHz): δ1.35, 1.4 (2s, 6H, CH$_3$), 1.6–1.82 (m, 4H, H-4,5), 2.85–3.05 (m, 2H, H-2,3), 3.35–3.7 (m, 3H, H-1,7), 3.2–3.98 (m, 2H, H-6,7a); $^{13}$CNMR (CDCl$_3$, 50 MHz): δ25.5, 26.6, 26.8, 27.5, 29.5, 44.4, 57.1, 58.3, 69.1, 75.0, 108.8.

Part 9: (3S,6S)-3-Hydroxy-6,7-isopropylidenedioxy-hept-1-yne (Scheme VIII; 12):

To freshly prepared LDA [prepared from diisopropylamine (14.9 mL, 114.5 mmol) and n-BuLi (70 mL, 109 mmol; 1.5 N hexane solution)] in THF (100 mL), (2S,3S,6S)-1-chloro-2,3-epoxy-6,7-isopropylidenedioxy heptane 11 (6.0 g, 27.2 mmol) in THF (20 mL) was added at –40° C. (CH$_3$CN+dry ice bath). After 3 h, the reaction was quenched with aq. NH$_4$Cl solution. The aqueous layer separated and extracted with EtOAc. Combined organic layers were dried (Na$_2$SO$_4$), evaporated and the residue purified by column chromatography (Si-gel, 30% EtOAc-hexane) to furnish (3S,6S)-3-hydroxy-6,7-isopropylidenedioxy-hept-1-yne 12 ( 3.9 g) in 94% yield as a yellow liquid. [α]$_D$+2.59 (c 1.54, CHCl$_3$); $^1$HNMR (CDCl$_3$, 200 MHz): δ1.35, 1.4 (2s, 6H) 1.6–198 (m, 4H, H-4,5), 2.4 (d, 1H, J 1.86 Hz, H-1), 3.5 (t, 1H, J 6.9 Hz, H-7), 3.98–4.2 (m, 2H, H-6,7a), 4.4 (m, 1H, H-3); $^{13}$CNMR (CDCl$_3$, 50 MHz): δ25.62, 26.84, 29.09, 33.85, 61.83, 69.24, 72.92, 75.55, 84.66, 109.01; MS: 169 (M$^+$–15); HRMS: Calculated for C$_9$H$_{13}$O$_3$ (M$^+$–15): 169.086469: Observed: 169.086063.

Part 10: (3S,6S)-3-Acetoxy-6,7-isopropylidenedioxy-hept-1-yne (Scheme I; 13)

A solution of(3S,6S)-3-hydroxy-6,7-isopropylidenedioxy-hept-1-yne 12 (3.9 g, 25.65 mmol) and Et$_3$N (10 mL, 76.9 mmol) in CH$_2$Cl$_2$ (40 mL) containing DMAP (catalytic) at 0° C. was treated with Ac$_2$O (3.65 mL, 38.48 mmol) and stirred at room temperature for 30 min. The reaction mixture was treated with saturated aqueous NaHCO$_3$ solution (20 mL) for 30 min. and the organic layer was separated. It was washed with water (3×20 mL), brine (25 mL) and dried (Na$_2$SO$_4$). Evaporation of solvent and purification of residue by column chromatography (Si-gel, 20% EtOAc-hexane) gave (3S,6S)-3-acetoxy-6,7-isopropylidenedioxy-hept-1-yne 13 (4.15 g) in 83 % yield as a pale yellow liquid. [α]$_D$–2.55 (c 1.96, CHCl$_3$); $^1$HNMR (CDCl$_3$, 200 MHz): δ1.25,1.35 (2s, 6H), 1.5–1.9 (3, 4H, H-4,5),2.02 (s, 3H, —OCH$_3$),2.35 (d, 1H, J 2.3 Hz, H-1), 3.45 (t, 1H, J 6.5 Hz, H-7), 3.9–4.1 (m, 2H, H-6,7a), 5.25–5.4 (m, 1H, H-3); $^{13}$CNMR (CDCl$_3$, 50 MHz): δ20.54, 25.58, 26.89, 29.71, 30).88, 63.88, 69.12, 73.81, 75.99, 80.80, 108.93, 169.87.

Part11: (3S,6S)-3-Acetoxy-6,7-dihydroxy-hept-1-yne (Scheme VII; 14)

A mixture of (3S,6S)-3-acetoxy-6,7-isopropylidenedioxy-hept-1-yne 13 (4.1 g) in 60% aqueous. AcOH (20 mL) was stirred at room temperature for 12 h. The reaction mixture was neutralised with saturated NaHCO$_3$ solution and extracted with EtOAc (3×50 mL). The combined organic layers were evaporated and the residue purified by filtration through a small pad of silica gel with 1:1 EtOAc-hexane to afford (3S,6S)-3-acetoxy-6,7-dihydroxy-hept-1-yne 14 (3.1 in 92% yield as a pale yellow liquid. [α]$_D$–49.6 (c 0.5, CHCl$_3$); $^1$HNMR (CDCl$_3$, 200 MHz): δ1.5–1.65 (m, 2H, H-4), 1.75–2.10 (m, 2H, H-5), 2.10 (s, 3H, —OAc), 2.45 (d, 1H, J 2.7 Hz, H-1), 3.38–3.5 (m, 1H, H-7), 3.55–3.78 (m, 2H, H-6,7a), 5.38 (dt, 1H, J 2.7, 5.0 Hz, H-3); $^{13}$CNMR (CDCl$_3$, 50 MHz): δ20.87, 28.17, 30.73, 63.57, 66.55, 71.52, 73.91, 80.86, 170.04.

Part 12: (3S,6S)-3-Acetoxy-6-hydroxy-7-p-toluene sulfonyloxy-hept-1-yne (Scheme VIII; L) 15)

A solution of(3S,6S)-3-acetoxy-6,7-dihydroxy-hept-1-yne 14 (4.3 g, 23.1 mmol) in CH$_2$Cl$_2$ (50 mL) containing pyridine (3.7 mL, 46.2 mmol) was cooled to 0° C. and treated with p-toluene sulfonyl chloride (4.4 g, 23.1 mmol) and stirred at room temperature for 5 h. The reaction mixture was diluted with CH$_2$Cl$_2$ (25 mL) and washed with aqueous CuSO$_4$ solution (2×25 mL) followed by water (2×25 n mL). Organic layer was dried (Na$_2$SO$_4$), evaporated and purified by chromatography (Si-gel, 15% EtOAc-hexane); first eluted was (3S,6S)-3-acetoxy-6,7-di-p-toluene sulfonyloxy-hept-1-yne 15a (1.14 g) in 10% yield as a yellow syrup. $^1$HNMR (CDCl$_3$, 200 MHz): δ1.48–1.8 (m, 4H, H-3,4), 2.0 (s, 3H, OAc), 2.31 (d, 1H, J 2.5 Hz, H-7) 2.4 (s, 3H, Ar—CH$_3$), 3.94 (d, 2H, J 4.5 Hz, H-1), 4.5–4.64 (m, 1H, H-2), 5.06–5.18 (m, 1H, H-5), 7.20–7.3, 7.56–7.7 (m, 4H each, Ar—H).

The second eluted was (3S,6S)-3-acetoxy-6-hydroxy-7-p-toluene sulfonyloxy-hept-1-yne 15 (3.77 g) as a yellow syrup. [α]$_D$–28.10 (c 2.0, CHCl$_3$); $^1$HNMR (CDCl$_3$, 200 MHz): δ1.5–1.65 (m, 2H, H-4), 1.7–2.08 (m, 2H, H-5), 2.10 (s, 3H, OAc), 2.43 (d, 1H, J 1.86 Hz, H-1) 2.55 (s, 3H, Ar—CH$_3$), 2.60 (br.s, 1H, OH), 3.8–4.05 (m, 3H, H-6,7,7a), 5.35 (dt, 1H, J 1.3, 6.9 Hz, H-3), 7.35, 7.8 (2d, 4H, J 7.9 Hz, Ar—H); EIMS m/z (relative intensity): 281 (M+1, 16), 155 (60), 136 (95), 109 (55), 91 (100).

Part 13: (2S,5S)-5-Ethynyl-2-(hydroxymethyl)-tetrahydrofuran (Scheme VIII; 16)

A solution of (3S,6S)-3-acetoxy-6-hydroxy-7-p-toluene sulfonyloxy-hept-1-yne 15 (3.67 g, 10.79 mmol) in MeOH (50 mL) at room temperature, was treated with K$_2$CO$_3$ (3.2 g, 23.7 mmol) and stirred for 3 h. It was further treated with NH$_4$Cl solution, evaporated MeOH and residue extracted with EtOAc (3×50 mL). Organic layer was washed with water (2×25 mL), brine (25 mL), dried (Na$_2$SO$_4$), and evaporated. The residue obtained was purified by column chromatography (Si-gel, 20% EtOAc-hexane) to afford (2S,5S)-5-ethynyl-2-(hydroxymethyl)-tetrahydrofuran 16 (1.35 g) in 90% yield as a colorless liquid. [α]$_D$–15.07 (c 1.26, CHCl$_3$); $^1$HNMR (CDCl$_3$, 200 MHz): δ1.9–2.38 (m, 4H, H-3,4), 2.45 (d, 1H, J 2.1 Hz, H-7), 3.55 (dd, 1H, J 6.3, 12.75 Hz, H-1), 3.72 (dd, 1H, J 3.8, 12.75 Hz, H-1a), 4.0–4.18 (m, 1H, H-2), 4.55–4.65 (m, 1H, H-5); $^{13}$CNMR (CDCl$_3$, 50 MHz): δ26.6, 29.64, 64.62, 68.33, 73.11, 80.7, 83.92.

Part 14: (2S,5S)-5-Ethynyl-2-(p-toluene sulfonyloxymethyl)-tetrahydrofuran (Scheme VIII; E17):

Procedure A: A solution of (2S,5S)-5-ethynyl-2-(hydroxymethyl)-tetrahydrofuran 16 (1.3 g, 10.2 mmol), Et$_3$N (6.7 mL, 51.5 mmol) in CH$_2$Cl$_2$ (25 mL) containing DMAP (10 mg) was treated with p-TsCl (2.39 g, 12.2 mmol) and stirred at room temperature for 4 h. Evaporation of solvent and purification of residue by column chromatography (Si-gel, 20% EtOAc-hexane) gave (2S,5S)-5-ethynyl-2-(p-toluene sulfonyloxymethyl)-tetrahydrofuran 17 (2.23 g) in 82% yield as a yellow syrup. [α]$_D$–30.86(c 1.38, CHCl$_3$); $^1$HNMR (CDCl$_3$, 200 MHz): δ1.8–2.25 (m, 4H, H-3,4), 2.35 (d, 1H, J 2.2 Hz, H-7), 2.45 (s, 3H, Ar—CH$_3$), 3.95–4.20 (m, 3H, H-2,1,1a), 4.55–4.60 (m, 1H, H-5), 7.32, 7.8 (2d, 4H, J9.0 Hz, Ar—H).

Procedure B: A solution of (3S,6S)-3-acetoxy-6,7-dihydroxy-hept-1-yne 14 (3.5 g, 18.81 mmol) in CH$_2$Cl$_2$ (50 mL) containing Et$_3$N (5.8 mL, 41.39 mmol) was cooled to 0° C. and treated with p-toluene sulfonyl chloride (4.3 g, 22.5 mmol) and stirred at room temperature for 8 hours. Evaporated the solvent and the residue was purified by column chromatography (Si-gel, 15% EtOAc-hexane) to give a mixture of compounds 15 and 17 (6.7 g).

The above mixture was treated with K$_2$CO$_3$ (6.4 g, 46.7 mmol) and stirred for 4 h. The reaction mixture was further treated with NH$_4$Cl solution, evaporated MeOH and residue extracted with EtOAc (3×50 mL). Organic layer was washed with water (2×25 mL), brine (25 mL), dried (Na$_2$SO$_4$), and evaporated. The residue obtained was purified by column chromatography (Si-gel, 15% EtOAc-hexane), first to afford (2S,5S)-5-ethynyl-2-(p-toluene sulfonyloxymethyl)-tetrahydrofuran 17 (1.5 g) as a yellow syrup.

The second eluted was (2S,5S)-5-ethynyl-2-(hydroxymethyl)-tetrahydrofuran 16 (1.61 g) as a liquid. Compound 16 (1.61 g, 12.77 mmol), was further tosylated with p-TsCl (2.65 g, 14 mmol) and Et$_3$N (4.1 mL, 31.9 mmol), as described in procedure A of this example to afford 17 (3.34 g) in 88% yield as a yellow syrup.

Part 15: (2S,5S)-5-Ethynyl-2-(4-fluorophenoxymethyl)-tetrahydrofuran (Scheme VIII; 18)

To a stirred suspension of NaH (0.57 g, 23.86 mmol) in DMF (5 mL), a solution of (2S,5S)-5-ethynyl-2-(p-toluene sulfonyloxymethyl)-tetrahydrofuran 17 (3.34 g, 11.92 mmol) in DMF (5 mL) was added, followed by the addition of 4fluoro phenol (1.74 g, 15.5 mmol) in DMF (5 mL) and heating at 80° C. for 2 hours. The reaction mixture was cooled to room temperature and treated with NH$_4$Cl solution (20 mL). It was extracted with ether (3×40 mL) and organic layer was washed with water (2×25 ML), brine (25 mL) and dried (Na$_2$SO$_4$). Evaporation of solvent and purification of residue by column chromatography (Si-gel, 2% EtOAc-hexane) afforded (2S,5S)-5-ethynyl-2-(4-fluorophenoxymethyl)-tetrahydrofuran 18 (1.55 g) in 59.6% yield as a colorless liquid, whose spectral data was comparable with the reported reference values. [α]$_D$–15.07(c 1.26, CHCl$_3$); $^1$HNMR (CDCl$_3$, 200 MHz): δ2.0–2.35 (m, 4H, H-3,4'), 2.45 (d, 1H, J 2.2 Hz, H-7), 3.95 (dd, 1H, J 4.5, 9.0 Hz, H-1), 4.12 (dd, 1H, J 4.54, 9.0 Hz, H-1a), 4.35 (quin, 1H, H-2), 4.65 (m, 1H, H-5), 6.85–7.05 (m, 4H, Ar—H); $^{13}$CNMR (CDCl$_3$, 50 MHz): δ28.24, 33.1, 68.45, 72.9, 79.9, 83.8, 71.28, 115.43, 115.52, 115.68, 115.89, 154.91, 159.66; MS: m/z 220 (M+); HRMS: Calculated for C$_{13}$H$_{13}$O$_2$ (M+): 220.089958; Observed; 220.089905.

EXAMPLE 8

Synthesis of (2R,5R)-5-Ethynyl-2-(hydroxymethyl)-tetrahydrofuran from L-Glyceraldehyde References in this Example 8 to compound numerals (generally underlined) designate the compounds depicted structurally in Scheme IX above.

Part 1: Ethyl (2E,4R)-4,5-isopropylidenedioxy-2-pentenoate (Scheme IX; 20)

A solution of (2S,3R)-1,2-O-isopropylidene-butane-1,2,3,4-tetrol 19 (11.0 g, 68.1 mmol) in CH$_2$Cl$_2$ (120 mL) containing saturated NaHCO$_3$ solution (4.5 mL) was cooled to 0° C., treated with NaIO$_4$ (29.1 g, 136.3 mmol) and allowed to stir at 0° C. to 200° C. After 2 to 3 h (TLC analysis), solid Na$_2$SO$_4$ (6 g) was added and the reaction mixture was stirred further for 15 min. The reaction mixture was filtered and solvent evaporated (below 25° C. bath temperature) to give (S)-glyceraldehyde 19a (8.7 g) in 98% yield as a colorless liquid. Compound 19 was prepared by procedures described in *J. Am. Chem. Soc.*, 102, 6304 (1980); and *J. Org. Chem.*, 53, 2598 (1988).

A solution of (S)-glyceraldehyde 19a (15 g, 115.4 mmol) in MeOH (200 mL) was cooled to 0°–10° C. (ice-salt bath) and treated with (carbethoxymethylene) triphenyl phosphorane (48.1 g, 138.4 mmol) in portions. After stirring at room temperature for 9 h, the solvent was evaporated, the residue obtained on purification by column chromatography (Si-gel, 10% EtOAc-Hexane) gave ethyl (2E,4R)-4,5-isopropylidenedioxy-2-pentenoate 20 (23 g) in 99% yield as a pale yellow liquid. $[\alpha]_D$-116.3(c 0.71, CHCl$_3$); $^1$HNMR (CDCl$_3$, 200 MHz): δ1.2 (t, 3H, J 6.8 Hz, CH$_3$), 1.3, 1.35 (2s, 6H, CH$_3$), 3.5 (dd, 1H, J 5.9 Hz, H-5), 4.07 (q, 2H, J 6.8 Hz, —OCH$_2$), 4.27 (dd, 1H, J 5.9 Hz, H-5a), 5.32–5.43 (m, 1H, H-4), 5.72 (dd, 1H, J 2.2, 11.3 Hz, H-2), 6.27 (dd, 1H, J 5.4, 11.3 Hz, H-3); $^{13}$CNMR (CDCl$_3$, 50 MHz): δ13.0, 25.2, 26.3, 60.1, 69.21, 73.3, 109.4, 120.5, 149.1, 165.3; EIMS m/z (relative intensity): 185 (M$^+$-15, 15), 173 (6), 149 (23), 125 (20), 97 (45), 43 (100); HRMS: Calculated for C$_9$H$_{13}$O$_4$ (M$^+$-15): 145.08469; Observed: 145.087162.

Part 2: Ethyl (4R)-4,5-isopropylidenedioxy-1-pentanoate (Scheme IX; 21)

A solution of ethyl (2E,4R)-4,5-isopropylidenedioxy-2-pentenoate 20 (23 g, 115 mmol) in EtOAc (50 mL) was treated with PtO$_2$ (0.100 g, mmol) and hydrogenated till there was no additional consumption of hydrogen (3–4 h). At the end of reaction, the reaction mixture was filtered and concentrated to afford ethyl (4R)-4,5-isopropylidenedioxy-1-pentanoate 21 (23 g) in 99% yield as a colorless liquid. $[\alpha]_D$-4.0(c 2.0, CHCl$_3$); $^1$HNMR (CDCl$_3$, 200 MHz): δ1.25 (t, 3H, J6.8 Hz, CH$_3$), 1.29, 1.32 (2s, 6H, CH$_3$), 1.75–1.89 (m, 2H, H-3), 2.3–2.45 (m, 2H, H-2), 3.5 (t, 1H, J 6.5 HZ, H-5), 3.92–4.15 (m, 4H, H-4,5a, —OCH$_2$); $^{13}$CNMR (CDCl$_3$, 50 MHz): δ14.0, 25.4, 26.8, 28.6, 30.2, 60.1, 68.8, 74.7, 108.7, 172.6. EIMS m/z (relative intensity): 203 (M$^+$+1, 23), 173 (16.4), 143 (13.4), 101 (100), 43 (97); HRMS: Calculated for C$_8$H$_{13}$O$_4$ (M$^+$-29): 173.0813 84; Observed: 1 173.081619.

Part 3: (2R)-1,2-Isopropylidenedioxy-5-pentanol (Scheme IX; 22)

A suspension of LAH (4.93 g, 130.4 mmol) in THF (50 mL) was cooled to 0° C. and treated drop wise with a solution of ethyl (4R)-4,5-isopropylidenedioxy-1-pentanoate 21 (22 g, 108.9 mmol) in THF (75 mL). The reaction mixture was warmed to room temperature, then allowed to stir for 3 h and treated with a saturated solution of Na$_2$SO$_4$ (15 mL). After stirring for additional 30 min., it was filtered through celite and washed with EtOAc (3×75 mL). The combined organic layers were washed with NaCl solution and evaporated to provide the (2R)-1,2-isopropylidenedioxy-5-pentanol 22 (17 g) in 97% yield as a colorless liquid. $[\alpha]_D$-10.3(c 0.75, CHCl$_3$); $^1$HNMR (CDCl$_3$, 200 MHz): δ1.35, 1.4 (2s, 6H), 1.6–1.75 (m, 4H, H-3,4), 1.92 (br.s, 1H, OH), 3.5 (t, 1H, J 6.1 Hz, H-1), 3.6–3.72 (m, 2H, H-5), 3.98–4.16 (m, 2H, H-1a,2); $^{13}$CNMR (CDCl$_3$, 50 MHz): δ25.6, 26.8, 29.0, 30.1, 62.4, 69.4, 75.9, 108.8; EIMS m/z (relative intensity): 145 (M$^+$-15, 13.4), 85 (32), 72 (18), 57 (13.4), 43 (100); HRMS: Calculated for C$_7$H$_{13}$O$_3$(M$^+$-15): 145.086468; Observed: 145.087162.

Part 4: (4R)-4,5-Isopropylidenedioxy-1-pentanal (Scheme IX; 23)

Method A: A stirred solution of (2R)-1,2-isopropylidenedioxy-5-pentanol 22 (17 g, 106.3 mol) in CH$_2$Cl$_2$ (200 mL) was treated with PDC (59.9 g, 159.3 mmol) in portions and allowed stir at 40° C. for 5 h. The reaction mixture was diluted with ether (4×300 mL) and decanted through a small pad of silica gel. Evaporation of solvent afforded (4R)4,5-isopropylidenedioxy-1-pentanal 23 (15 g) in 89% yield as a pale yellow liquid.

Method B: A stirred solution of(2R)-1,2-isopropylidenedioxy-5-pentanol 22 (0.800 g, 5.0 mmol) in DMSO (5 mL) was cooled to 0° C., treated with IBX (1.47 g, 5.26 mmol) in portions while maintaining the temperature below 0° C. and stirred at room temperature for 4 h. The reaction mixture was treated with saturated NaHCO$_3$ solution, filtered through celite and washed with EtOAc (3×30 mL). Two layers were separated and organic layer was washed with water, brine and dried (Na$_2$SO$_4$). Evaporation of solvent gave (4R)-4,5-isopropylidenedioxy-1-pentanal 23 (16.2 g) in 78% yield as a yellow liquid. $[\alpha]_D$+0.3(c 2.0, CHCl$_3$).

Part 5: Ethyl (2E,6R)-6,7-isopropylidenedioxy hept-2-enoate (Scheme IX; 24)

A solution of (4R)-4,5-isopropylidenedioxy-1-pentanal 23 (15 g, 94.9 mmol) in benzene ( 200 mL) was treated with (carbethoxymethylene) triphenyl phosphorane (39.6 g, 113.8 mmol) and heated at reflux for 6 h. Solvent was evaporated and the residue purified by column chromatography (Si-gel, 10% EtOAc-hexane) to afford ethyl (2E,6R)-6,7-isopropylidenedioxy hept-2-enoate 24 (14 g) in 65% yield as a pale yellow liquid. $[\alpha]_D$-5.4(c 1.2, CHCl$_3$); $^1$HNMR (CDCl$_3$, 200 MHz): δ1.3 (t, 3H, J 6.8 Hz,CH$_3$), 1.34, 1.4 (2s, 6H), 1.61–1.7 (m, 2H, H-6), 2.2–2.42 (m, 2H, H-4), 3.5 (t, 1H, J 6.8 Hz, H-7a), 3.99–4.26 (m, 4H, H-6,7,—OCH$_2$), 5.82 (td,1H, J 2.25, 15.75 Hz, H-2), 6.94 (dt, 1H, J 6.8, 15.75 Hz, H-3); $^{13}$CNMR (CDCl$_3$, 50 MHz): δ14.0, 25.4, 26.7, 28.2, 31.9, 60.0, 69.0, 74.9, 108.7, 121.7, 147.7, 166.3; EIMS m/z(relative intensity): 213 (M$^+$-15, 9), 95 (40.2), 67 (25.3), 55 (53.7), 41 (100); HRMS: Calculated for C11H$_{17}$O$_4$ (M$^+$-15): 213.112684; observed: 213.112732.

Part 6: (2E,6R)-6,7-Isopropylidenedioxy hept-2-ene-1-ol (Scheme IX; 25)

A stirred solution of ethyl (2E,6R)-6,7-isopropylidenedioxy hept-2-enoate 24 (13.87 g, 60.8 mmol) in dry CH$_2$Cl$_2$ (60 mL) was cooled to −20° C. (CCl$_4$+dry ice bath) and treated with a solution of DIBAL-H (17.27 g, 121.6 g, mmol; 2.5M solution in hexane) drop wise. After stirring for 2 h, the reaction mixture was warmed to 0° C., treated drop wise with MeOH (10 mL) to obtain a gelatin cake. The mixture was diluted with CH$_2$Cl$_2$ (100 mL) and stirred for 15 min. A solution of Na—K tartarate (90 mL) was added drop wise and stirred for an additional 45 min. Reaction mixture was filtered through celite and washed with CH$_2$Cl$_2$ (2×50 mL). The organic layer was washed with water (2×100 mL), brine (50 mL), dried (Na$_2$SO$_4$) and evaporated to give (2E,6R)-6,7-isopropylidenedioxy hept-2-ene-1-ol 25 (11 g) in 98.2% yield as a colorless liquid. $[\alpha]_D$-13.2 (c 2.5, CHCl$_3$); $^1$HNMR (CDCl$_3$, 200 MHz): δ1.16,1.2 (2s, 6H, CH$_3$), 1.46–1.74 (m, 2H, H-5), 1.79–198 (m, 1H, —OH), 2.02–2.19 (m, 2H, H-4), 3.36–3.78(m, 3H, H-6,7), 4.02–4.12 (m, 2H, H-1), 5.61–5.71 (m, 2H, H-2,3); $^{13}$CNMR (CDCl$_3$, 50 MHz): δ25.3, 26.5, 28.0, 32.7, 62.8, 68.9, 75.1, 108.3, 129.8 (2C); EIMS m/z (relative intensity): 171 (M$^+$-15, 35.8), 93 (22.3), 67 (37.3), 55 (26.8), 43 (100); HRMS: Calculated for C9H15O3 (M+-15): 171.102120; observed: 171.102195.

Part 7: (2R,3R,6R)-2,3-Epoxy-6,7-isopropylidenedioxy heptan-1-ol (Scheme IX; 26)

To a stirred and cooled (−20° C.) suspension of molecular sieves (4 A, 1.25 g) in CH$_2$Cl$_2$ (10 mL) under N$_2$ atmosphere, (−)-diisopropyl D-tartarate (7.6 g, 32.4 mmol), titanium(IV) isopropoxide (7.68 g, 27.02 mmol) and cumene hydroperoxide (8.22 g, 54 mmol) were added sequentially. After 20 min., the resulting mixture was treated drop wise addition of a solution of (2E,6R)-6,7-isopropylidenedioxy hept-2-ene-1-ol 25 (5 g, 26.88 mmol) in $CH_2Cl_2$ (15 mL) and stirred for additional 3 h. The reaction mixture was quenched with 10% NaOH solution saturated with NaCl (15 mL) and filtered through celite. Evaporation of solvent and purification of residue by column chromatography (Si-gel, 1:1 EtOAc-hexane) gave (2R,3R,6R)-2,3-epoxy-6,7-isopropylidenedioxy heptan-1-ol 26 (4.15 g) in 76.4% yield as a colorless liquid. $[\alpha]_D$+24.3(c 0.3, $CHCl_3$); $^1$HNMR ($CDCl_3$, 200 MHz): δ1.32, 1.38 (2s, 6H, $CH_3$), 1.58–1.78 (m, 4H, H-4,5), 2.8–3.01 (m, 2H, H-2,3), 3.5 (t, 1H, J 6.1 Hz, H-7), 3.6 (dd, 1H, J 4.7, 11.75 Hz, H-1), 3.85 (dd, 1H, J 3.29, 11.75, H-1a), 3.98–4.2 (m, 2H, H-6,7'); $^{13}$CNMR ($CDCl_3$, 50 MHz): δ25.5, 26.8, 27.6, 29.6,–55.3, 58.3, 61.6, 69.1, 75.1, 108.8; EIMS M/Z (relative intensity): 188 ($M^+$–15, 14.9), 144 (85), 101 (47.7), 83 (95), 43 (100); HRMS: Calculated for $C_9H_{15}O_4$ (M–15): 187.097034; Observed: 187.096634.

Part 8: (2R,3R,6R)-1-Chloro-2,3-epoxy-6,7-isopropylidenedioxy heptane (Scheme IX; 27)

A stirred mixture of (2R,3R,6R)-2,3-epoxy-6,7-isopropylidenedioxy heptan-1-ol 26 (3.8 g, 18.8 mmol), $Ph_3P$ (7.4 g, 28.3 mmol) and $NaHCO_3$ (0.6 g) in $CC_4$ (50 mL) was heated at reflux for 3 h. The solvent was evaporated and residue obtained purified by column chromatography (Si-gel, 20% EtOAc-hexane) to give (2R,3R,6R)-1-chloro-2,3-epoxy-6,7-isopropylidenedioxy heptane 27 (2.8 g) in 67.8% yield as a colorless liquid. $[\alpha]_D$+8.16(c 0.7, $CHCl_3$); $^1$HNMR ($CDCl_3$, 200 MHz): δ1.31, 1.36 (2s, 6H, $CH_3$), 1.63–1.72 (m, 4H, H-4,5), 2.8–2.9 (m, 1H, H-2), 2.91–3.02 (m, 1H, H-3), 3.32–3.68 (m, 3H, H-1,7), 3,95–4.19 (m, 2H, H-6,7a); $^{13}$CNMR ($CDCl_3$, 50 MHz): δ25.6, 26.9, 27.6, 29.6, 44.5, 57.0, 58.3, 69.2, 75.1, 108.9; EIMS m/z (relative intensity): 205 ($M^+$–15, 35.8), 145 (23), 83 (61), 72 (98), 43 (100); HRMS: Calculated for $C_9H_{14}ClO_3$ ($M^+$–15): 205.063147; Observed: 205.062719.

Part 9: (3R,6R)-3-Hydroxy-6,7-isopropylidenedioxy-hept-1-yne (Scheme IX; 28)

To freshly prepared LDA [prepared from diisopropyl amine (4.6 g, 45.45 mmol) and n-BuLi (2.91 g, 45.54 mmol; 1.4N hexane solution)] in THF (10 mL),a solution of (2R,3R,6R)-1-chloro-2,3-epoxy-6,7-isopropylidenedioxy heptane 27 (2.5 g, 11.36 mmol) in THF (20 mL) was added at –40° C. ($CH_3CN$+dry ice bath). After 3 h, the reaction was quenched with aq. $NH_4Cl$ solution and diluted with $CH_2Cl_2$ (50 mL). The organic layer was separated, washed with water (3×20 mL), brine (200 mL) and dried ($Na_2SO_4$), evaporated and residue purified by column chromatography (Si-gel, 15% EtOAc-hexane) to furnish (3R,6R)-3-hydroxy-6,7-isopropylidenedioxy-hept-1-yne 28 ( 2.0 g) in 95.2% yield as a pale yellow liquid. $[\alpha]_D$–3.02(c 2.2, $CHCl_3$); $^1$HNMR ($CDCl_3$, 200 MHz): δ1.32, 1.39 (2s, 6H, $CH_3$), 1.64–1.94 (m, 4H, H-4,5), 2.19–2.21 (br.s, 1H, OH), 2.39 (d, 1H, J 2.3 Hz, H-1), 3.5 (t, 1H, J 5.7 Hz, H-7), 3.96–4.16 (m, 2H, H-6,7a), 4.34–4.45 (m, 1H, H-3); $^{13}$CNMR ($CDCl_3$, 50 MHz): δ25.4, 26.6, 28.8, 33.5, 61.3, 69.0, 72.7, 75.3, 84.7, 108.7; EIMS m/z (relative intensity): 169 ($M^+$–15, 22.3), 109 (20.8), 81 (37.3), 55 (35.8), 43 (100); HRMS: Calculated for $C_9H_{13}O_3$ (M–15): 169.086469; Observed: 169.086140.

Part 10: (3R,6R)-3-Acetoxy-6,7-isopropylidenedioxy-hept-1-yne (Scheme IX; 29)

A solution of hydroxy-6,7-isopropylidenedioxy-hept-1-yne 28 (1.8 g, 9.8 mmol) and pyridine (3.1 g, 39.2 mmol) in $CH_2Cl_2$ (15 mL) containing DMAP (catalytic) at 0° C. was treated with $Ac_2O$ (1.2 g, 11.7 mmol) and stirred at room temperature for 30 min. After completion, the reaction was diluted with $CH_2Cl_2$ (50 mL), sequentially washed with $CuSO_4$ solution (3×20 mL), saturated aq. $NaHCO_3$ solution (20 mL), water ( 20 mL), brine (20 mL) and dried. Evaporation of solvent and purification of residue by column chromatography (Si-gel, 10% EtOAc-hexane) gave (3R,6R)-3-acetoxy-6,7-isopropylidenedioxy-hept-1-yne 29 (2.15 g) in 97.2% yield as a yellow liquid. $[\alpha]_D$+37.5(c 2.1, $CHCl_3$); $^1$HNMR ($CDCl_3$, 200 MHz): δ1.3, 1.39 (2s, 6H, $CH_3$), 1.64–2.0 (m, 2H, H-4,5), 2.06 (s, 3H, $CH_3$), 2.4 (d, 1H, J 2.0 Hz, H-1), 3.5 (t, 1H, J 5.7 4.13 (m, 2H, H-6,7a), 5.31–5.41 (m, 1H, H-3); $^{13}$CNMR ($CDCl_3$, 50 MHz): δ20.8, 25.5, 26.8, 28.8, 30.7, 63.3,69.1, 73.7, 75.1, 80.7, 108.9, 169.6; EIMS m/z (relative intensity): 211 ($M^+$–15, 29.8), 169 (11.9), 91 (22.3), 72 (23), 43 (100); HRMS: Calculated for $C_{11}H_{15}O_4$ ($M^+$–15): 211.097034; Observed; 211.095947.

Part 11: (3R,6R)-3-Acetoxy-6,7-dihydroxy-hept-1-yne (Scheme IX; 30)

A solution of (3R,6R3-acetoxy-6,7-isopropylidenedioxy-hept-1-yne 29 (2 g, 8.8 mmol) in MeOH (150 mL) containing catalytic amount of PTSA was stirred at 0° C. for 8 h. The reaction mixture was neutralised with saturated sat. $NaHCO_3$ solution, evaporated to remove MeOH and extracted with EtOAc (3×50 mL). Organic layer were evaporated and the residue filtered through a small pad of silica gel with 1:1 EtOAc-hexane to afford (3R,6R)-3-acetoxy-6,7-dihydroxy-hept-1-yne 30 (1.2 g) in 72.9% yield as a colorless syrup. $[\alpha]_D$+83.2 (c 1.2, $CHCl_3$); $^1$HNMR ($CDCl_3$, 200 MHz): δ1.5–1.7 (m, 2H, H4), 1.75–2.05 (m, 2H, H-5), 2.14 (s, 3H, —OAc), 2.45 (d, 2H, H-1), 2.57 (br.s, 1H, OH), 3.35–3.5 (m, H, H-7), 3.57–3.8 (m, 2H, H-6,7a), 5.32–5.47 (m, 1H, H-3); CIMS m/z (relative intensity): 187 (M+1, 74.6), 127 (59.7), 109 (35.8), 81 (56.7), 43 (100); HRMS Calculated for $C_9H_{15}O_4$ ( M+1): 187.097034; Observed: 187.096547.

Part 12. (3R,6R)-3-Acetoxy-6-hydroxy-7-p-toluene sulfonyloxy-hept-1-yne (Scheme IX; 31)

A solution of (3R,6R)-3-acetoxy-6,7-dihydroxy-hept-1-yne 30 (1.1 g, 5.9 mmol) in $CH_2Cl_2$ (20 mL) containing pyridine (0.934 g, 11.82 mmol) was cooled to 0° C., treated with p-TsCl (1.12 g, 5.91 mmol) and stirred at room temperature for 8 h. The reaction mixture was diluted with $CH_2Cl_2$ and washed sequentially with water (20 mL), $CuSO_4$ solution (3×20 mL) and water (20 mL). Organic layer was dried ($Na_2SO_4$), evaporated and residue obtained was purified by column chromatography (Si-gel, 10% EtOAc-Hexane); first eluted was (3R,6R)-3-acetoxy-6,7-di-p-toluene sulfonyloxy-hept-1-yne 31a (0.23 g) in 8% yield as a yellow syrup. $^1$HNMR ($CDCl_3$, 200 MHz): δ1.5–1.85 (m, 4H, H-3,4), 2.05 (s, 3H, OAc), 2.41–2.52 (m, 7H, H-7, Ar—$CH_3$), 4.0 (d, 2H, J4.8 Hz, H-1), 4.58–4.62 (m, 1H, H-2), 5.12–5.26 (m,1H, H-5), 7.28–7.44, 7.64–7.81 (m, 4H each, Ar—H).

Second eluted was (3R,6R)-3-acetoxy-6-hydroxy-7-p-toluene sulfonyloxy-hept-1-yne 31 (1.1 g) in 55% yield as a yellow syrup. $[\alpha]_D$+28.1 (c 1.0, $CHCl_3$); $^1$HNMR ($CDCl_3$, 200 MHz): δ1.35–1.68 (m, 3H, H-4,—OH), 1.68–2.0 (m, 2H, H-5), 2.08 (s, 3H, $CH_3$), 2.4 (d, 1H, J 2.4 Hz, H-1), 2.46 (s, 3H, Ar—$CH_3$), 3.79–4.06 (m, 3H, H-6,7), 5.35 (td,1H, J 4.8, 7.2 Hz, H-3),7.36 (d, 2H, J 7.2 Hz, Ar—H), 7.8 (d, 2H, J 7.2 Hz, Ar—H). FABMS m/z (relative intensity): 341(M+

1, 13.8), 281(50), 155(54.1), 133(52.7), 109(100). HRMS: Calculated for $C_{16}H_{21}O_6S$ (M+1):341.105885; Observed:341.104916.

Part 13: (2R,SR)-5-Ethynyl-2-(hydroxymethyl)-tetrahydrofuran (Scheme IX; 32)

To a solution of (3R,6R)-3-acetoxy-6-hydroxy-7-p-toluene sulfonyloxy-hept-1-yne 31 (0.6 g, 1.76 mmol) in MeOH (10 mL) at room temperature, $K_2CO_3$ (0.536 g, 3.88 mmol) was added and the mixture was stirred for 2 h. It was treated with $NH_4Cl$ solution, evaporated MeOH and the residue extracted with EtOAc (3×20 mL). Organic layer was washed with water (10 mL), brine (10 mL), dried ($Na_2SO_4$) evaporated. The residue obtained was purified by column chromatography (Si-gel, 20% EtOAc-hexane) to furnish (2R,5R)-5-ethynyl-2-(hydroxymethyl)-tetrahydrofuran 32 (0.22 g) in 99% yield as a colorless liquid. $[\alpha]_D$+20.0 (c 1.0, $CHCl_3$); $^1$HNMR ($CDCl_3$, 200 MHz): δ1.89–2.38 (m, 4H, H-3,4), 2.4 (br.s, 1H, OH), 2.46 (d, 1H, J 2.2 Hz, H-7), 3.55 (dd, 1H, J 4.5, 11.25 Hz, H-1), 3.72 (dd, 1H, J 4.0, 11.25 Hz, H-1a), 4.0–4.15 (m, 1H, H-2), 4.52–4.66 (m,1H, H-5); $^{13}$CNMR ($CDCl_3$, 50 MHz): δ26.6, 29.6, 33.6, 64.6, 68.3, 73.0, 80.7; EIMS m/z (relative intensity): 125 (M$^+$–1, 8), 95 (74.6), 67 (100), 53 (40), 41 (80); HRMS: Calculated for $C_7H_9O_2$ (M–1): 125.060255; Observed: 125.060322.

Part 14: (2R,5R)-5-Ethynyl-2-(p-toluene sulfonyloxymethyl)-tetrahydrofuran (Scheme IX; 33)

A solution of alcohol (2R,5R)-5-ethynyl-2-(hydroxymethyl)-tetrahydrofuran 32 (0.22 g, 1.75 mmol) in pyridine (0.6 mL) was treated with p-TsCl (0.354 g, 1.86 mmol) and the mixture stirred at room temperature for 3 h. The reaction mixture was diluted with $CH_2Cl_2$ (20 mL) and washed sequentially with water (10 mL), $CuSO_4$ solution (2×10 mL), brine (10 mL) and dried ($Na_2SO_4$). Evaporation of solvent and purification of residue by column chromatography (Si-gel, 15% EtOAc-hexane) gave (2R,5R)-5-ethynyl-2-(p-toluene sulfonyloxymethyl)-tetrahydrofuran 33 (0.33 g) in 63.9% yield as a yellow syrup. $[\alpha]_D$+10.0 (c 0.54, $CHCl_3$); $^1$HNMR ($CDCl_3$, 200 MHz): δ1.84–2.11 (m, 4H, H-3,4) 2.32 (d, 1H, J 2.1 Hz, H-7), 2.45 (s, 3H, $CH_3$), 3.92–4.2 (m, 3H, H-2,1,1a), 4.48–4.58 (m, 1H, H-5), 7.34 (d, 2H, J 7.6 Hz, Ar—H), 7.8 (d, 2H, J 7.6 Hz, Ar—H); CIMS m/z (relative intensity): 281(M+1, 100), 109(49.2), 117(31.3), 81(7.0), 43(100); HRMS: Calculated for $C_{14}H_{17}O_4S$ (M+1):281.084756; Observed: 281.083610.

Part 15: (2R,5R)-5-Ethynyl-2-(4-fluoro phenoxymethyl)-tetrahydrofuran (Scheme IX; 34)

To a stirred suspension of NaH (0.032 g, 1.33 mmol) in DMF (3 mL), a solution of (2R,5R)-5-ethynyl-2-(p-toluene sulfonyloxy methyl)-tetrahydrofuran 33 (0.33 g, 1.1 mmol) in DMF (3 mL) was added and heated at 80° C. for 5 h. The reaction mixture was cooled to room temperature and treated with $NH_4Cl$ solution. It was extracted with ether (2×10 mL) and the organic layer was washed with water (2×10 mL), brine (10 mL) and dried ($Na_2SO_4$). Evaporation of solvent and purification of residue by column chromatography (Si-gel, 7% EtOAc-hexane) afforded (2R,5R)-5-ethynyl-2-(4-fluoro phenoxy methyl)-tetrahydrofuran 34 (0.21 g) in 85.7% yield as a colorless liquid, whose spectral data is accordance with the reported reference values. $[\alpha]_D$+16.0 (c 1.0, $CHCl_3$); $^1$HNMR ($CDCl_3$, 200 MHz): δ1.88–2.32 (m, 4H, H-3,4), 2.41 (d, 1H, J 2.3 Hz, H-7), 3.9 (dd, 1H, J 4.6, 9.1 Hz, H-1), 4.06 (dd, 1H, J 5.9, 9.1 Hz, H-1a), 4.22–4.36 (m, 1H, H-2), 4.58–4.69 (m, 1H, H-5), 6.75–7.02 (m, 4H, Ar—H); $^{13}$CNMR ($CDCl_3$, 50 MHz): δ28.2, 33.1, 68.5, 71.2, 72.9, 76.3, 83.7, 115.4, 115.6, 115.8, 115.9, 154.9, 159.6; EIMS m/z (relative intensity): 220 (M+, 10.4), 125 (14.9), 95 (94), 67 (100), 41 (59.7); HRMS: Calculated for $C_{13}H_{13}O_2F$ (M+): 220.089958; Observed: 220.089497.

EXAMPLE 9

Preparation of (2R,5S)-5-Ethynyl-2-(hydroxymethyl)-tetrahydrofuran

References in this Example 9 to compound numerals (generally underlined) designate the compounds depicted structurally in Scheme X above.

Part 1: (2S,3S,6R)-2,3-Epoxy-6,7-isopropylidenedioxy heptan-1-ol (Scheme X; 43)

To a stirred and cooled (–20° C.) suspension of molecular sieves (4 A, 0.55 g) in $CH_2Cl_2$ (10 mL) under $N_2$ atmosphere, (+)-diisopropyl D-tartarate (4.0 g, 17.41 mmol), titanium(IV) isopropoxide (4.12 g, 14.51 mmol) and cumene hydroperoxide (4.4 g, 29.0 mmol) were added sequentially. After 20 min., the resulting mixture was treated drop wise addition of a solution of (2E,6R)-6,7-isopropylidenedioxy hept-2-ene-1-ol 25 (2.7 g, 14.51 mmol) in $CH_2Cl_2$ (10 mL) and stirred for additional 3 h. The reaction mixture was quenched with 10% NaOH solution saturated with NaCl (15 mL) and filtered through celite. Evaporation of solvent and purification of residue by column chromatography (Si-gel, 1:1 EtOAc-hexane) gave (2R,3R,6R)-2,3-epoxy-6,7-isopropylidenedioxy heptan-1-ol 43 (2.1 g) in 72.4% yield as a colorless liquid. $[\alpha]_D$–26.9(c 1.1, $CHCl_3$); $^1$HNMR ($CDCl_3$, 200 MHz): δ1.32, 1.38 (2s, 6H, $CH_3$), 1.58–1.79 (m, 4H, H4,5), 2.3–2.52 (br.s 1H, OH). 2.84–3.0 (m, 2H, H-2,3), 3.5 (t, 1H, J 6.1 Hz, H-7), 3.6 (dd, 1H, J 4.5, 12.0 Hz, H-1), 3.85 (dd, 1H, J 3.3, 11.2 Hz, H-1a), 3.98–4.2 (m, 2H, H-6,7').

Part 2: (2S,3S,6R)-1-Chloro-2,3-epoxy-6,7-isopropylidenedioxy heptane (Scheme X; 44)

A stirred mixture of (2S,3S,6R)-2,3-epoxy-6,7-isopropylidenedioxy heptan-1-ol 43 (1.9 g, 9.4 mmol), $Ph_3P$ (3.7 g, 14.1 mmol) and $NaHCO_3$ (0.3 g) in $CCl_{14}$ (25 mL) was heated at reflux for 3 h. The solvent was evaporated and residue obtained purified by column chromatography (Si-gel, 20% EtOAc-hexane) to give (2S,3S,6R)-1-chloro-2,3-epoxy-6,7-isopropylidenedioxy heptane 44 (1.5 g) in 75% yield as a colorless liquid. $[\alpha]_D$+12.9 (c 1.2, $CHCl_3$); $^1$HNMR ($CDCl_3$, 200 MHz): δ1.32, 1.39 (2s, 6H, $CH_3$), 1.58–1.72 (m, 4H, H-4,5), 2.8–2.9 (m, 1H, H-2), 2.91–3.02 (m, 1H, H-3), 3.32–3.68 (m, 3H, H-1.7), 3.94–4.16 (m, 2H, H-6,7a).

Part 3: (3S,6R)-3-Hydroxy-6,7-isopropylidenedioxy-hept-1-yne (Scheme X; 45)

To freshly prepared LDA [prepared from diisopropyl amine (2.3 g, 23.6 mmol) and n-BuLi (15.7 mL, 23.6 mmol; 1.5N hexane solution)] in THF (6 mL), a solution of (2S,3S,6R)-1-chloro-2,3-epoxy-6,7-isopropylidenedioxy heptane 44 (1.5 g, 5.9 mmol) in THF (10 mL) was added at –40° C. ($CH_3CN$+dry ice bath). After 3 h, the reaction was quenched with aq. $NH_4Cl$ solution and diluted with $CH_2Cl_2$ (25 mL). The organic layer was separated, washed with water (3×15 mL), brine (100 mL) and dried ($Na_2SO4$), evaporated and residue purified by column chromatography (Si-gel, 15% EtOAc-hexane) to furnish (3S,6R)-3-hydroxy- 6,7-isopropylidenedioxy-hept-1-yne 45 (1.0 g) in 83% yield as a pale yellow liquid. [α]$_D$–21.0 (c 1.0, CHCl$_3$); $^1$HNMR (CDCl$_3$, 200 MHz): δ1.34, 1.4 (2s, 6H, CH$_3$), 1.64–1.9 (m, 4H, H-4,5), 2.49 (d, 1H, J 2.3 Hz, H-1), 2.55–2.7 (br.s, 1H, OH), 3.52 (t, 1H, J 5.8 Hz, H-7), 3.98–4.16 (m, 2H, H-6,7a), 4.35–4.49 (m, 1H, H-3).

Part 4: (3S,6R)-3-Acetoxy-6,7-isopropylidenedioxy-hept-1-yne (Scheme X; 46)

A solution of (3S,6R)-3-hydroxy-6,7-isopropylidenedioxy-hept-1-yne 45 (1.0 g, 5.43 mmol) and Et$_3$N (2.74 g, 27.15 mmol) in CH$_2$Cl$_2$ (10 mL) containing DMAP (catalytic) at 0° C. was treated with Ac$_2$O (0.665 g, 6.52 mmol) and stirred at room temperature for 30 min. After completion, the reaction was diluted with CH$_2$Cl$_2$ (25 mL), washed with water (2×20 mL), brine (20 mL) and dried. Evaporation of solvent and purification of residue by column chromatography (Si-gel, 10% EtOAc-hexane) gave (3S,6R)-3-acetoxy-6,7-isopropylidenedioxy-hept-1-yne 46 (1.1 g) in 91% yield as a yellow liquid. [α]$_D$–56.5 (c 1.0, CHCl$_3$); $^1$HNMR (CDCl$_3$, 200 MHz): δ1.32, 1.39 (2s, 6H, CH$_3$), 1.46–2.01 (m, 2H, H-4,5), 2.08 (s, 3H, CH$_3$), 2.41 (d, 1H, J 2.3 Hz, H-1), 3.5 (t, 1H, J 6.9 Hz, H-7), 3.98–4.14 (m, 2H, H-6,7a), 5.31–5.42 (m, 1H, H-3).

Part 5: (3S,6R)-3-Acetoxy-6,7-dihydroxy-hept-1-yne (Scheme X; 47)

A solution of (3S,6R)-3-acetoxy-6,7-isopropylidenedioxy-hept-1-yne 46 (1.1 g, 4.86 mmol) in 60% aqueous AcOH (10 mL) was stirred at room temperature for 12 h. The reaction mixture was neutralised with saturated sat. NaHCO$_3$ solution and extracted with EtOAc (3×50 mL). Organic layer was dried (Na$_2$SO$_4$), evaporated and the residue filtered through a small pad of silica gel with 1:1 EtOAc-hexane to afford (3S,6R)-3-acetoxy-6,7-dihydroxy-hept-1-yne 47 (0.6 g) in 66.6% yield as a colorless syrup. [α]$_D$–46.3 (c 1.0, CHCl$_3$); HNMR (CDCl$_3$, 200 MHz): δ1.45–1.7 (m, 2H, H-4), 1.75–2.05 (m, 2H, H-5), 2.09 (s, 3H, —OAc), 2.4 (br.s, 2H, H-1, OH), 3.32–3.5 (m, 2H, H-7), 3.52–3.8 (m, 2H, H-6,7a), 5.3–5.44 (m, 1H, H-3).

Part 6: (3S,6R)-3-Acetoxy-6-hydroxy-7-p-toluene sulfonyloxy-hept-1-yne (Scheme X; 48)

A solution of (3S,6R)-3-acetoxy-6,7-dihydroxy-hept-1-yne 47 (0.6 g, 3.22 mmol) and Et$_3$N (0.975 g, 9.66 mmol) in CH$_2$Cl$_2$ (10 mL) was cooled to 0° C., treated with p-TsCl (0.737 g, 3.87 mmol) and stirred at room temperature for 10 hours. The reaction mixture was diluted with CH$_2$Cl$_2$ (20 mL) and washed with water (2×15 mL) and brine (20 mL). Organic layer was dried (Na$_2$SO$_4$), evaporated and residue obtained was purified by column chromatography (Si-gel, 10% EtOAc-Hexane) to afford (3S,6R)-3-acetoxy-6-hydroxy-7-p-toluene sulfonyloxy-hept-1-yne 48 (0.94 g) in 89% yield as a colorless syrup. [α]$_D$–37.2 (c 1.3, CHCl$_3$); $^1$HNMR (CDCl$_3$, 200 MHz): δ1.51–2.0 (m, 5H, H-4, 5,—H), 2.08 (s, 3H, CH$_3$), 2.4 (d, 1H, J 2.3 Hz, H-1), 2.48 (s, 3H, Ar—CH$_3$), 3.8–4.06 (m, 3H, H-6,7), 5.35 (td,1H, J 4.8, 7.2 Hz, H-3), 7.36 (d, 2H, J 7.9 Hz, Ar—H), 7.8 (d, 2H, J 7.9 Hz, Ar—H).

Part 7: (2R,5S)-5-Ethynyl-2-(hydroxymethyl)-tetrahydrofuran (Scheme X; 49)

To a solution of (3S,6R)-3-acetoxy-6-hydroxy-7-p-toluene sulfonyloxy-hept-1-yne 48 (0.9 g, 2.64 mmol) in MeOH (15 mL) at room temperature, K$_2$CO$_3$ (0.805 g, 5.83 mmol) was added and the mixture was stirred for 2 h. It was treated with NH$_4$Cl solution, evaporated MeOH and the residue extracted with EtOAc (3×20 mL). Organic layer was washed with water (10 mL), brine (10 mL), dried (Na2SO$_4$) evaporated. The residue obtained was purified by column chromatography (Si-gel, 20% EtOAc-hexane) to furnish (2R,5S5-ethynyl-2(hydroxymethyl)-tetrahydrofuran 49 (0.4 g) in 95% yield as a colorless liquid. [α]$_D$–10.5 (c 1.0, CHCl$_3$); $^1$HNMR (CDCl$_3$, 200 MHz): δ1.50–2.3 (m, 4H, H-3,4), 2.4 (br.s, 1H, OH), 2.42 (d, 1H, J 2.2 Hz, H-7), 3.5 (dd, 1H, J 4.5, 11.3 Hz, H-1), 3.75 (dd, 1H, J 3.3, 11.35 Hz, H-1a), 4.164.34 (m, 1H, H-2), 4.6–4.74 (m,1H, H-5).

Part 8: (2R,5S)-5-Ethynyl-2-(-toluene sulfonyloxymethyl)-tetrahydrofuran (Scheme X; 50)

A solution of alcohol(2R,5)-5-ethynyl-2-(hydroxymethyl)-tetrahydrofuran 49 (0.33 g, 2.6 mmol) and Et$_3$N (0.263 g, 7.8 mmol) in CH$_2$Cl$_2$ (10 mL) containing DMAP (catalytic ) was treated with p-TsCl (0.499 g, 2.6 mmol) at 0° C. and the mixture stirred at room temperature for 3 hours. The reaction mixture was diluted with CH$_2$Cl$_2$ (20 mL) and washed sequentially with water (2×10 mL), brine (10 mL) and dried Na$_2$SO$_4$) Evaporation of solvent and purification of residue by column chromatography (Si-gel, 15% EtOAc-hexane) gave (2R,5S)-5-ethynyl-2-(p-toluene sulfonyloxy methyl)-tetrahydrofuran 50 (0.4 g) in 55% yield as a colorless syrup. [α]$_D$–7.0(c 1.0, CHCl$_3$); $^1$HNMR (CDCl$_3$, 200 MHz): δ1.64–2.0 (m, 4H, H-3,4) 2.22 (d, 1H, J2.1 Hz, H-2.35 (s, 3H, CH$_3$), 3.72–4.05 (m, 3H, H-2,1,1a), 4.28–4.48 (m, 1H, H-5), 7.34 (d, 2H, J 7.6 Hz, Ar—H), 7.8 (d, 2H, J 7.6 Hz, Ar—H).

Part 9: (2R,5S)-5-Ethynyl-2-(4-fluoro phenoxymethyl)-tetrahydrofuran (Scheme X; 51)

To a stirred suspension of NaH (0.041 g, 1.71 mmol) in DMF (3 mL), a solution of (2R,5S)-5-ethynyl-2-(p-toluene sulfonyloxy methyl)-tetrahydrofuran 50 (0.32 g, 1.1 mmol) in DMF (3 mL) was added and heated at 80° C. for 3 h. The reaction mixture was cooled to room temperature and treated with NH$_4$Cl solution. It was extracted with hexane (2×10 mL) and the organic layer was washed with water (2×10 mL), brine (10 mL) and dried (Na$_2$SO$_4$). Evaporation of solvent and purification of residue by column chromatography (Si-gel, 7% EtOAc-hexane) afforded (2R,5S)-5-ethynyl-2-(4-fluoro phenoxy methyl)-tetrahydrofuran 51 (0.19 g) in 76% yield as a colorless liquid,[α]$_D$–21.5 (c 1.1, CHCl$_3$); (CDCl$_3$, 200 MHz): δ1.8–2.34 (m, 4H, H-3,4), 2.38 (d, 1H, J 2.3 Hz, H-7), 3.81–4.0 (m, 2H, H-1,1a), 4.36–4.51 (m, 1H, H-2), 4.64–4.78 (m, 2H, H-5), 6.75–7.02 (m, 4H, Ar—H).

EXAMPLE 10

Preparation of (2S,5R)-5-Ethynyl-2-(hydroxymethyl)-tetrahydrofuran from homopropargyl alcohol References in this Example 10 to compound numerals (generally underlined) designate the compounds depicted structurally in Scheme XI above.

Part 1: (2S,5RS)-5-Hydroxy-1,2-isopropylidenedioxy-9-p-methoxyphenyl methyl-non-6-yn-9-ol (Scheme XI; 35)

A stirred solution of 1-p-methoxy phenyl methyl but-3-yn-1-ol (1.0 g, 5.3 mmol) in THF (5 mL) at −78° C. was treated with n-BuLi (3.8 mL, 3.8 mmol; 1.5 N hexane solution). After 30 min, a solution of (4S)-4,5-isopropylidenedioxy-1-pentanal 7 (0.6 g, 3.8 mmol) in THF (5 mL) was added dropwise and stirred for 1 hour at the same temperature. The reaction mixture was warmed to room temperature, quenched with aqueous $NH_4Cl$ solution. Aqueous layer was separated and back extracted with EtOAc. Combined organic layers were dried ($Na_2SO_4$), evaporated and residue purified by column chromatography (Si-gel, EtOAc-hexane) to furnish (2S,5RS)-5-hydroxy-1,2-isopropylidenedioxy-9-p-methoxyphenyl methyl-non-6-yn-9-ol 35 (0.75 g) in 57% yield as a pale yellow syrup. $[\alpha]_D$+11.0 (C 1.0, $CHCl_3$); $^1$HNMR ($CDCl_3$, 200 MHz): δ1.35, 1.4 (2s, 6H) 1.64–1.85 (m, 5H, H-3,4,—OH), 2.5 (dt, 1H, J 2.1, 8.6 Hz, H-8), 3.45–3.58 (m, 3H, H-1,9), 3.8 (s, 3H, —$OCH_3$), 3.96–4.15 (m, 2H, H-1a,2), 4.32–4.42 (m, 1H, H-5), 4.46 (S,2H, H-10), 6.85, 7.22 (2d, 2H each, J 7.5 Hz, Ar—H); FABMS m/z (relative intensity): 348(12.3), 347 (39.7), 289(26.1), 189(100); HRMS: Calculated for $C_{20}H_{27}O_5$ ($M^+$-1): 347.185849; Observed: 347.185567.

Part 2: (2S,5RS)-5-Acetoxy-1,2-isopropylidenedioxy-9-p-methoxy phenyl methyl-non-6-yn-9-ol (Scheme XI; L36)

A solution of (2S,5RS)-5-hydroxy-1,2-isopropylidenedioxy-9-p-methoxyphenyl methyl-non-6-yn-9-ol 35 (0.7 g, 2.01 mmol) and pyridine (0.7 mL, 8.04 mmol) in $CH_2Cl_2$ (10 mL) containing DMAP (catalytic) at 0° C. was treated with $Ac_2O$ (0.23 mL, 2.4 mmol) and stirred at ambient temperature for 30 min. The reaction mixture was diluted with $CH_2Cl_2$ (50 mL), washed sequentially with $CuSO_4$ solution (3×20 mL), $NaHCO_3$ solution (20 mL), water (20 mL), brine (20 mL) and dried ($Na_2SO_4$). Evaporation of solvent and purification of residue by column chromatography (Si-gel, EtOAc-hexane) gave (2S,5RS)-5-acetoxy-1,2-isopropylidenedioxy-9-p-methoxy phenyl methyl-non-6yn-9-ol 36 (0.684 g) in 87% yield as a pale yellow s00000yrup. $[\alpha]_D$9.5 (c 1.0, $CHCl_3$) $^1$HNMR ($CDCl_3$, 200 MHz): δ1.36,1.42 (2s, 6H), 1.6–2.0 ( m, 4H, H-3,4), 2.1 (s, 3H, OAc), 2.45–2.56 (dt, 1H, J 2.17, 8.2 Hz, H-8), 3.45–3.60 (m, 3H, H-1,9), 3.82 (s, 3H, —$OCH_3$), 3.96–4.14 (m, 2H, H-1a,2), 4.48 (s, 2H, —$OCH_2$), 5.32–5.45 ( m, 1H, H-5), 6.86, 7.25 (2d, 2H each, J 7.6 Hz, Ar—H); FABMS m/z (relative intensity): 413(M+23, 4), 391(6), 337(19), 253(10), 143(100).

Part 3: (2S,5RS)-5-Acetoxy-1,2-dihydroxy-9-p-methoxy phenyl methyl-non-6-yn-9-ol (Scheme XI; 37)

A mixture of (2S,5RS)-5-acetoxy-1,2-isopropylidenedioxy-9-p-methoxy phenyl methyl-non-6-yn-9-ol 36 (0.8 g) in 60% aqueous AcOH (8 mL) was stirred at room temperature for 12 h. The reaction mixture was neutralised with saturated $NaHCO_3$ solution and extracted with EtOAc (3×50 mL). Organic layer was evaporated and residue was purified by filtration through a small pad of silica gel with 1:1 EtOAc-hexane to afford (2S,5RS)-5-acetoxy-1,2-dihydroxy-9-p-methoxy phenyl methyl-non-6-yn-9-ol 37 (0.6 g) in 83.5% yield as a syrup. $[\alpha]_D$6.5 (c 1.0, $CHCl_3$); $^1$HNMR ($CDCl_3$, 200 MHz): δ1.46–1.65 (m, 2H, H-4), 1.69–2.0 (m, 2H, H-3), 2.09 (s, 3H, OAc), 2.02–2.26 (br.s, 2H, —OH), 2.5 (t, 2H, H-8), 3.3–3.46 (m, 1H, H-1), 3.46–3.78 ( m, 4H, H-1,2,9), 3.8 (s, 1H, —$OCH_3$), 4.45 (s, 2H, —$OCH_2$), 5.3–5.42 (m, 1H, H-5), 6.82, 7.2 (d, 4H, J7.2 Hz, Ar—H); FABMS m/z (relative intensity): 335(M-15, 12.5), 215(5.5), 183(27.7), 154(64.3), 107(100). HRMS: Calculated for $C_{18}H_{23}O_6$ ($M^+$-15): 335.149464; Observed: 335.149249.

Part 4: (2S,5RS)-5-Acetoxy-2-hydroxy-9-p-methoxy phenyl methyl-2-p-toluene sulfonyloxy-non-6-yn-9-ol (Scheme XI; 38)

A solution of (2S,5RS)-5-acetoxy-1,2-dihydroxy-9-p-methoxy phenyl methyl-non-6-yn-9-ol 37 (0.6 g, 1.71 mmol) in $CH_2Cl_2$ (20 mL) containing pyridine (0.27 g, 3.42 mmol) was cooled to 0° C. and treated with p-TsCl (0.327 g, 1.71 mmol) and stirred at room temperature for 4 h. The reaction mixture was diluted with $CH_2Cl_2$ (15 mL), washed with water (2×20 mL), $NaHCO_3$ solution (2×20 mL), water (20 mL), brine (20 mL), dried ($Na_2SO_4$) and evaporated. Purification of the residue obtained by column chromatography (Si-gel, 10% EtOAC-Hexane) gave (2S,5RS)-5-acetoxy-2-hydroxy-9-p-methoxy phenyl methyl-2-p-toluene sulfonyloxy-non-6-yn-9-ol 38 (0.8 g) in 92.5% yield as a yellow syrup. $^1$HNMR ($CDCl_3$, 200 MHz): δ1.52–1.98 (m, 4H, H-3,4), 1.98 (s, 3H, OAc), 2.41–2.56 (m, 5H, H-8, Ar—$CH_3$), 3.34–3.72 m, 2H, H-9), 3.8 (s, 3H, —$OCH_3$), 3.94–4.2 (m, 2H, H-1,2), 4.45 (s, 2H, —$OCH_2$), 4.56–4.72 (m, 1H, H-5), 5.26–5.4 (m, 1H, H-1a), 6.82, 7.21 (2d, 2H each, J 7.9 Hz, Ar—H), 7.26–7.3 (m, 2H, Ar—H), 7.62–7.82 (m, 2H, Ar—H).

Part 5: (2S,5RS)-2-(Hydroxymethyl)-5-(1-p-methoxyphenylmethyleneoxy-but-3-yn-4-yl)-tetrahydrofuran (Scheme )XI; 39)

To a solution of (2S,5RS)-5-acetoxy-2-hydroxy-9-p-methoxy phenyl methyl-2-p-toluene sulfonyloxy-non-6-yn-9-ol 38 (0.8 g, 1.58 mmol) in MeOH (15 mL) at room temperature, $K_2CO_3$ (0.482 g, 3.49 mmol) was added and stirred for 4 h. It was treated with $NH_4Cl$ solution, evaporated MeOH and residue extracted with EtOAc (3×30 mL). Organic layer were washed with water (2×30 mL), brine (20 mL), dried (Na2SO4) and evaporated. The residue obtained was purified by column chromatography (Si-gel, 15% EtOAc-hexane) to afford (2S,5RS)-2-(hydroxymethyl)-5-(1-p-methoxyphenylmethylen oxy-but-3-yn-4-yl)-tetrahydrofuran 39 (0.45 g) in 97.8% yield as a yellow syrup. $^1$HNMR ($CDCl_3$, 200 MHz): δ1.85–2.12 (m, 4H, H-3,4), 2.4–2.54 (m, 2H, H-8), 3 3.59 (m, 2H, H-9), 3.68 (dd, 2H, J 2.38, 11.9 Hz, H-1), 3.8 (s, 3H, $OCH_3$), 4.1–4.26 (m, 1H, H-2), 4.44 (s, 2H, —$OCH_2$), 4.58–4.70 (m, 1H, H-5), 6.81, 7.2 (2d, 2Ar—H).

Part 6: (2S,5RS)-5-(1-p-Methoxyphenylmethylenoxy-but-3-yn-4-yl)-2-(p-toluenesulfonyloxymethyl)-tetrahydrofuran (Scheme XI; 40)

A solution of (2S,5RS)-2-(hydroxymethyl)-5-(1-p-methoxyphenylmethylenoxy-but-3-yn-4-yl)-tetrahydrofuran 39 (0.45 g, 1.55 mmol), pyridine (0.25 mL, 3.1 mmol) in $CH_2Cl_2$ (10 mL) was treated with p-TsCl (0.325 g, 1.70 mmol) and stirred at room temperature for 4 h. Reaction mixture was diluted with $CH_2Cl_2$ (20 mL) and washed sequentially with $CuSO_4$ solution (3×20 mL), $NaHCO_3$ solution (20 mL), water (20 mL), brine (20 mL) and dried ($Na_2SO_4$). Evaporation of solvent and purification of residue by column chromatography (Si-gel, 10% EtOAc-hexane) gave (2S,5RS)-5-(1-p-methoxyphenylmethylenoxy-but-3-yn-4-yl)-2-(p-toluenesulfonyloxymethyl)-tetrahydro furan 40 (0.45 g) in 65.3% yield as a yellow syrup. $^1$HNMR ($CDCl_3$, 200 MHz): δ1.74-2.21 (m, 4H, H-3,4), 2.39–2.49 (m, 2H, H-8), 2.5 (s, 3H, Ar—$CH_3$), 3.5 (t, 2H, J 8.1 Hz, H-9), 4.44 (s, 2H, —$OCH_2$), 4.5–4.6 (m, 1H, H-2), 6.82 (d, 2H, J 7.9 Hz, Ar—H), 7.16–7.38 (m, 4H, Ar—H), 7.79 (d, 2H, J 7.9 Hz, Ar—H).

Part 7: (2S,5RS)-2-(p-Fluorophenoxymethyl)-5-(1-p-methoxyphenylmethylenoxy-but-3-yn-4-yl)-tetrahydrofuran (Scheme XI; 41)

To a stirred suspension of NaH (25.9 g, 1.08 mmol) in DMF (3 mL), a solution of (2S,5RS)-5-(1-p-methoxyphenylmethylenoxy-but-3-yn-4-yl)-2-(p-toluenesulfonyloxymethyl)-tetrahydrofuran 40 (0.4 g, 0.9 mmol) in DMF (3 mL) was added, followed by the addition of 4-fluoro phenol (0.121 g, 1.08 mmol) in DMF (2 mL) and heated at 80° C. for 2 h. The reaction mixture was cooled to room temperature and treated with NH$_4$Cl solution (5 mL). It was extracted with ether (3×15 mL) and organic layer was washed with water (3×15 mL), brine (15 mL) and dried (Na$_2$SO$_4$). Evaporation of solvent and purification of residue by column chromatography (Si-gel, 6% EtOAc-hexane) afforded (2S,5RS)-2-(p-fluorophenoxymethyl)-5-(1-p-methoxyphenylmethylenoxy-but-3-yn-4-yl)-tetrahydrofuran 41 (0.325 g) in 93.9% yield as a colorless syrup. $^1$HNMR (CDCl$_3$, 200 MHz): δ1.82–2.29 (m, 4H, H-3,4), 2.42–2.58 (m, 2H, H-8), 3.45–3.59 (m, 2H, H-9), 3.81 (s, 3H, —OCH$_3$), 3.85–3.96 (m, 2H, H-1), 4.0–4.14 (m, 1H, H-2), 4.66–4.76 (m, 1H, H-5), 6.76–7.0 (m, 6H, Ar—H), 7.18–7.3 (m, 2H, Ar—H); FABMS m/z (relative intensity): 384(18), 383(69), 369(10), 313(20), 121(100); HRMS: Calculated for C$_{23}$H$_{24}$O$_4$F (M$^+$-1): 383.165863; Observed: 383.164866.

Part 8: (2S,5RS)-2-(p-Fluorophenoxymethyl)-5-(1-hydroxy-but-3-yn-4-yl)-tetrahydrofuran (Scheme XI; 42)

A mixture of (2S,5RS)-2-(p-fluorophenoxy methyl)-5-(1-p-methoxyphenylmethylenoxy-but-3-yn-4-yl)-tetrahydrofuran 41 (0.3 g, 0.78 mmol) and DDQ (0.212 g, 0.937 mmol) in aqueous CH$_2$Cl$_2$ (20 mL; 1:19) was stirred at room temperature for 5 h. The reaction mixture was treated with saturated NaHCO$_3$ solution (10 mL) and diluted with CH$_2$Cl$_2$ (40 mL). Organic layer was separated and washed with water (3×30 mL), brine (20 mL) and dried (Na$_2$SO$_4$). Evaporation of solvent afforded (2S,5RS)-2-(p-fluorophenoxymethyl)-5-(1-hydroxy-but-3-yn-4-yl)-tetrahydrofuran 42 (0.140 g) in 67.9% yield as a liquid, whose spectral data was comparable with the reported (Org Process & Development, 3,73–76, 1999) values. $^1$H NMR (CDCl$_3$, 200 MHz): δ1.8–2.34 (m, 5H, H-6.7,—OH), 2.4–2.52 (m, 2H, H-2), 3.6–3.75 (m, 2H, H-1), 3.84–4.0 (m, 2H, H-9), 4.16–4.5 (m, 1H, H-5), 4.5–4.75 (m, 1H, H-8), 6.72–7.0(m, 4H, Ar—H).

EXAMPLE 11

Asymmetric Reduction

References in this Example 11 to compound numerals (generally underlined) designate the compounds depicted structurally in Scheme XII above.

Part 1: (4S)-4,5-Isopropylidenedioxy-1-pentanoic acid (Scheme XII; 57)

A solution of ethyl (4S)-4,5-isopropylidenedioxy-1-pentanoate (5; 5 g, 24.7 mmol) in DME (30 mL) was cooled to 0° C. and treated with a solution of LiOH (60 mL; 1N solution in water) and allowed to stir at room temperature for 3 hours. The reaction mixture was quenched with AcOH (till neutral to pH) and extracted with EtOAc (3×75 mL). Organic layer was dried over (Na$_2$SO$_4$) and evaporation of solvent gave (4S)-4,5-isopropylidenedioxy-1-pentanoic acid 57 (4.1 g) in 95% yield as a colorless liquid. $^1$HNMR (CDCl$_3$, 200 MHz): δ1.3, 1.35 (2s, 6H, CH$_3$), 1.8–1.95 (m, 2H, H-3), 2.4–2.6 (m, 2H, H-2), 3.55 (t, 1H, J 6.1 Hz, H-5), 3.8–4.2 (m, 2H, H-4,5a).

Part 2: 1,2-Isopropylidenedioxy-9-p-methoxy phenyl methyl--5-oxo-non-6-yn-9-ol (Scheme XII; 59)

A. Preparation of mixed anhydride (Scheme XII; 58): A stirred and cooled (−10° C. to 0° C.) solution of(4S)-4,5-isopropylidenedioxy-1-pentanoic acid 57 (1 g, 5.74 mmol) and freshly distilled Et$_3$N (0.58 g, 5.7 mmol) in dry ether (5 mL), was treated with ethyl chloro formate (0.62 g, 5.7 mmol). The reaction mixture was allowed to reach room temperature and stirred for 3 h. The reaction mixture was filtered and washed with ether. Organic layer was washed with saturated NaHCO$_3$ solution (25 mL), water (25 mL), brine (20 mL) and dried (Na$_2$SO$_4$). Evaporation of solvent under vacuum at room temperature afforded mixed anhydride 58 (1 g) in 71% yield as a colorless syrup.

B. 1,2-Isopropylidenedioxy-9-p-methoxy phenyl methyl--5-oxo-non-6-yn-9-ol (Scheme XII; 59): A stirred solution of 1-p-methoxy phenyl methyl-but-3-yne-1-ol (0.5 g, 2.03 mmol) in dry THF (5 mL) was cooled to -78° C. and treated with n-BuLi (1.35 mL, 2.03 mmol; 1.5 N hexane solution) dropwise. After 30 min., a solution of anhydride 58 (0.5 g, 2.03 mmol) in THF (5 mL) was added and stirred at the same temperature for 2 hours. The reaction mixture was quenched with aqueous NH$_4$Cl solution (10 mL) and extracted with EtOAc (2×25 mL). Organic layer was washed with brine (25 mL), dried (Na$_2$SO$_4$), evaporated and purified the residue by column chromatography (Si-gel, 8:1 Hexane-EtOAc) to afford 1,2-isopropylidenedioxy-9-p-methoxy phenyl methyl--5-oxo-non-6-yn-9-ol 59 (0.095 g) in 13.5% yield as a colorless syrup. $^1$HNMR (CDCl$_3$, 200 MHz): δ1.32, 1.4 (2s, 6H, CH$_3$), 1.75–2.2 (m, 2H, H-3), 2.6–2.8 (m, 4H, H-4,8), 3.45–3.7 (m, 3H, H-1,9), 3.8 (s, 3H, —OMe), 3.8–4.15 (m, 2H, H-1a,2), 4.5 (s, 2H, —OCH$_2$), 6.85, 7.25 (2d, 2H each, J 9.3 Hz, Ar—H).

Part 3: (2S,5RS)-5-Hydroxy-1,2-isopropylidenedioxy-9-p-methoxyphenyl methyl-non-6-yn-9-ol (Scheme XII; 60): A solution of 9-BBN (0.087 g, 0.72 mmol) in dry THF (5 mL) under N$_2$ atmosphere was treated with cc-pinene (0.1 18 g, 0.86 mmol; technical grade) and heated at reflux for 2.5 h. The reaction mixture was cooled to room temperature and a solution of 1,2-isopropylidenedioxy-9-p-methoxy phenyl methyl--5-oxo-non-6-yn-9-ol 59 (0.25 g, 0.712 mmol) in THF (5 mL) was added and allowed to stir for 82 h. The reaction mixture was treated with propanaldehyde (0.5 mL), stirred for 15 min. and solvent was evaporated at room temperature. The residue was dissolved in dry ether (10 mL), cooled to 0° C. and treated with ethanolamine (0.097 g, 1.5 mmol) and stirred for 15 min. It was filtered and washed with ether (5 mL). The ethereal layer was washed with brine (20 mL), dried (Na$_2$SO$_4$) and evaporated. The residue obtained was purified by column chromatography (Si-gel, 1:4 EtOAc-hexane) to afford (2S,5RS)-5-hydroxy-1,2-isopropylidenedioxy-9-p-methoxyphenyl methyl-non-6-yn-9-ol 60 (0.098 g) in 40% yield as a colorless syrup. Compound 60 prepared by the present approach is identical to compound 35 prepared in Scheme IX by TLC analysis as well as $^1$HNMR data.

EXAMPLE 12

Keto-epoxide Cyclisation

References in this Example 12 to compound numerals (generally underlined) designate the compounds depicted structurally in Scheme XII above.

Part 1: Non-8-ene-1-p-methoxy phenyl methyl--5-oxo-3-yn-1-ol (Scheme XIII; 54)

A. Mixed anhydride (Scheme XIII; 53): A stirred and cooled (−10° C. to 0° C.) solution of pent-4-enoic acid (0.5 g, 5 mmol) and freshly distilled Et$_3$N (0.505 g, 5 mmol) in dry ether (5 mL), was treated with ethyl chloro formate (0.542 g, 5 mmol). The reaction mixture was allowed to reach room temperature and stirred for 3 h. The reaction mixture was filtered and washed with ether. Organic layer was washed with saturated NaHCO$_3$ solution (25 mL), water (25 mL), brine (20 mL) and dried (Na$_2$SO$_4$). Evaporation of solvent under vacuum at room temperature afforded mixed anhydride 53 (0.79 g) in 91.8% yield as a colorless syrup.

B. Non-8-ene-1-p-methoxy phenyl methyl-5-oxo-3-yn-1-ol (Scheme XIII; 54): A stirred solution of 1-p-methoxy phenyl methyl-but-3-yn-1-ol (52; 1.12 g, 5.91 mmol) in dry THF (5 mL) was cooled to −78° C. and treated with n-BuLi (4 mL, 5.91 mmol; 1.5 N hexane solution) dropwise. After 30 min., a solution of anhydride 53 (0.78 g, 4.54 mmol) in THF (5 mL) was added and stirred at the same temperature for 2 hours. The reaction mixture was quenched with aq. NH$_4$Cl solution (10 mL) and extracted with EtOAc (2×25 mL). Organic layer was washed with brine (25 mL), dried (Na$_2$SO$_4$), evaporated and purified the residue by column chromatography (Si-gel, 8:1 Hexane-EtOAc) to afford non-8-ene-1-p-methoxy phenyl methyl-5-oxo-3-yn-1-ol (54; 0.35 g) in 27% yield as a colorless syrup. $^1$HNMR (CDCl$_3$, 200 MHz): δ2.32–2.46 (m, 2H, H-7), 2.56–2.69 (m, 4H, H-6,2), 3.59 (t, 2H, J 8.37 Hz, H-1), 3.8 (s, 3H, —OMe), 4.47 (s, 2H, —OCH$_2$), 4.95–5.11 (m, 2H, H-9), 5.67–5.9 (m, 1H, H-8), 6.84, 7.22 (2d, 2H each, J 9.3 Hz, Ar—H).

Part 2: 1,2-Epoxy-9-p-methoxy phenyl methyl--5-oxo-non-6-yn-9-ol (Scheme XIII; 55)

A solution of non-8-ene-1-p-methoxy phenyl methyl-5-oxo-3-yn-1-ol 54 (0.2 g, 0.73 mmol) in acetone (5 mL) was sequentially treated with solid NaHCO$_3$ (0.306 g, 3.65 mmol), water (5 mL) followed by a solution of oxone (0.448 g, 073 mmol) in aqueous. 4×10$^{-4}$ M EDTA disodium solution (10 mL) dropwise at 0° C. and stirred at room temperature for 4 h. The reaction mixture was filtered and washed with EtOAc (10 mL). The aqueous layer was extracted with EtOAc (2×10 mL) and combined organic layers were washed with brine (20 mL) and dried (Na$_2$SO$_4$). Evaporation of solvent and purification of residue by column chromatography (Si-gel, 15% EtOAc in hexane) gave 1,2-epoxy-9-p-methoxy phenyl methyl-5-oxo-non-6-yn-9-ol 55 (0.1 g) in 48% yield as a colorless syrup. $^1$HNMR (CDCl$_3$, 200 MHz): δ1.62–1.82 (m, 1H, H-3), 1.9–2.1 (m, 1H, H-3'),2.41–2.57 (m, 1H, H-1), 2.57–2.74 (m, 5H, H-1',4,8), 2.85–2.96 (m, 1H, H-2), 3.58 (t, 2H, J 8.13 Hz, H-9), 3.8 (s, 3H, —OMe), 4.45 (s, 2H, —OCH$_2$), 6.84, 7.22 (2d, 2H each, J 9.3 Hz, Ar—H).

Part 3: (2S,5RS)-2-(Hydroxymethyl)-5-(1-p-methoxyphenylmethylenoxy-but-3-yn-4-yl)-tetrahydrofuran (Scheme XIII; 56)

To a stirred and cooled −78° C. solution of 1,2-epoxy-9-p-methoxy phenyl methyl-5-oxo-non-6-yn-9-ol 55 (0.075 g. 0.26 mmol) in CH$_2$Cl$_2$ (52 mL; 0.005M solution), a solution of BH$_3$-DMS (0.25 mL, 0.26 mmol; 1 M solution in CH$_2$Cl$_2$) was added dropwise. After 3 hours, the reaction mixture was quenched with aq. NH$_4$Cl solution (10 mL) at 0° C. and extracted with EtOAc (2×10 mL). Organic layer was washed with water (2×10 mL), brine (10 mL) and dried (Na$_2$SO$_4$). Evaporation of solvent and purification of residue by column chromatography (Si-gel, 25% EtOAc in hexane) gave racemic 2-(Hydroxymethyl)-5-(1-p-methoxyphenylmethylenoxy-but-3-yn-4-yl)-tetrahydrofuran 56 (0.025 g) in 34% yield as a colorless syrup. The compound 56 thus obtained by this approach is comparable to compound 39 (Scheme IX) by TLC analysis as well as $^1$HNMR data.

EXAMPLE 13

5-methyl Substitution of γ-butyrolactone

Sodium hydride (60%, 192 g) is taken in a 3-neck round-bottom flask fitted with a mechanical stirrer and addition funnel. Dry n-hexane (1.0 L) is added and the mixture stirred for 15 minutes. The stirring is then stopped and the sodium hydride allowed to settle. After 15 minutes, n-hexane is decanted out. Dimethyl formamide (DMF) (2.0L) is charged to the flask. 4-fluorophenol (500 g) dissolved in DMF (2.0L) is added to the mixture over 0.5 hours, maintaining the temperature between 10–15° C. Tetrabutylammonium iodide (20 g) is added to the mixture maintaining temperature at 10–15° C. 5-hydroxymethyl-γ-butyrolactone (compound 60 in Scheme XIV where R is hydrogen) dissolved in DMF (3.0L) is added slowly over 1.5 hours while maintaining the temperature between 10–15° C. The reaction mixture is heated at 60–65° C. and temperature maintained for 1.0 hours. Thin layer chromatography can be checked to ensure disappearance of starting material. The reaction mixture is quenched with saturated NH$_4$Cl solution (500 ml), followed by acidification with 18% HCl (500 ml) and then stirred for 0.5 hours at room temperature. Water (12.0L) is added to the reaction mixture and the product (compound 61 in Scheme XIV above where R' is para-fluorophenyl) extracted into ethyl acetate (5.0L). The ethyl acetate layer is separated and washed with brine solution (2×2.0L) and then dried over sodium sulfate (250 g) and concentrated under reduced pressure. The resulting crude product can be chromatographed over silica gel using 10% ethyl acetate:n-hexane as eluent.

The invention has been described in detail including preferred embodiments thereof. However, it will be understood that those skilled in the art, upon consideration of this disclosure, may make modifications and improvements thereon without departing from the spirit and scope of the invention as set forth in the following claims.

What is claimed is:

1. A method for preparing a 4-fluorophenoxymethyl γ-butyrolactone, comprising:
   a) reacting mannitol with an aldehyde compound to form a trialkylene mannitol;
   b) hydrolyzing the trialkylene mannitol to provide a 2,5-O-alkylene-mannitol; and
   c) functionalizing secondary hydroxy groups of the 2,5-O-alkylene-mannitol to provide a fused ring cyclic ether comprising a first cyclic ether fused to a second cyclic ether;
   d) reacting the fused ring cyclic ether with 4-fluorophenol to form a bis-4-fluorophenylether; and
   e) cleaving the bis-4-fluorophenylether to form a 4-fluorophenoxymethyl γ-butyrolactone.

2. The method of claim 1 wherein primary hydroxy-substituted carbons of the fused ring cyclic ether are activated prior to reaction with 4-fluorophenol.

3. The method of claim 1 wherein the fused ring cyclic ether is cleaved to an acyclic ether prior to forming the 4-fluorophenoxymethyl γ-butyrolactone.

4. The method of claim 3 wherein the acyclic ether is of the following formula:

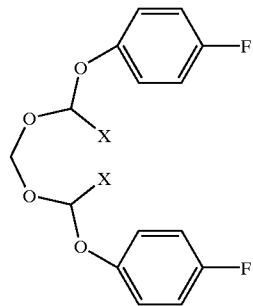

wherein each X is the same or different α, β-unsaturated electron-withdrawing group.

5. The method of claim 1 wherein an enantiomeric excess of a stereoisomer of the γ-butyrolactone moiety is formed.

6. The method of claim 1 wherein cleavage of the bis-4-fluorophenylether produces two molar equivalents of the 4-fluorophenoxymethyl γ-butyrolactone.

7. A method for preparing 4-fluorophenoxymethyl-(alkynyl)-tetrahydrofuran, comprising:
   treating with base a compound comprising a substituted alkyl group to form a 4-fluorophenoxymethyl-(alkynyl)-tetrahydrofuran,
   wherein the substituted alkyl group has 6 or more carbon atoms, the 2,3-positions of alkyl group forming an epoxide ring, the 1-position of the alkyl group substituted with a first leaving group, and the 6-position of the alkyl group substituted with a second leaving group.

8. The method of claim 7 wherein the substituted alkyl compound is treated with a molar excess of base.

9. The method of claim 7 wherein the substituted alkyl compound is treated with about a three molar excess of base.

10. The method of claim 7 wherein the base is an alkyllithium reagent, an amide salt or a hydride.

11. The method of claim 7 wherein the first and second leaving groups are each independently a halogen, a sulfonic alkyl ester, a sulfonic aryl ester or a sulfonic arylalkyl ester.

12. The method of claim 7 wherein one or both of the epoxide carbons are optically active.

13. The method of claim 7 wherein the formed 4-fluorophenoxymethyl-(alkynyl)-tetrahydrofuran is optically active.

14. The method of claim 7 wherein both of the epoxide carbons are optically active.

15. The method of claim 7 wherein the two carbons adjacent to the ring oxygen of the formed 4-fluorophenoxymethyl-(alkynyl)-tetrahydrofuran are each optically active.

16. The method of claim 7 wherein the 4-fluorophenoxymethyl-(alkynyl)-tetrahydrofuran is formed from the substituted alkyl compound without isolation of intermediate compounds.

17. The method of claim 7 wherein the 4-fluorophenoxymethyl-(alkynyl)-tetrahydrofuran is formed from the substituted alkyl compound in a single reaction step.

18. The method of claim 7 wherein the tetrahydrofuran is of the following structure:

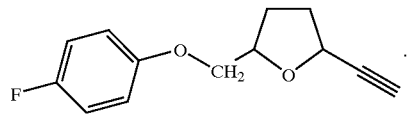

* * * * *